United States Patent
Minter et al.

(10) Patent No.: US 9,884,902 B2
(45) Date of Patent: Feb. 6, 2018

(54) CTLA-4 VARIANTS

(71) Applicants: MedImmune, LLC, Gaithersburg, MD (US); MedImmune Limited, Cambridge (GB)

(72) Inventors: Ralph Minter, Cambirdge (GB); Julie Douthwaite, Cambridge (GB); Jacques Moisan, North Potomac, MD (US); Michael Bowen, Gaithersburg, MD (US); Steven Rust, Cambridge (GB); Cyril Privezentzev, Sawston (GB)

(73) Assignee: MedImmune Limited, Cambridge (GB)

( * ) Notice: Subject to any disclaimer, the term of this patent is extended or adjusted under 35 U.S.C. 154(b) by 292 days.

(21) Appl. No.: 14/399,685

(22) PCT Filed: Mar. 11, 2013

(86) PCT No.: PCT/US2013/030179
§ 371 (c)(1),
(2) Date: Jun. 9, 2015

(87) PCT Pub. No.: WO2013/169338
PCT Pub. Date: Nov. 14, 2013

(65) Prior Publication Data
US 2015/0104450 A1   Apr. 16, 2015

Related U.S. Application Data

(60) Provisional application No. 61/645,686, filed on May 11, 2012.

(51) Int. Cl.
*A61K 38/00* (2006.01)
*C07K 14/705* (2006.01)

(52) U.S. Cl.
CPC ........ *C07K 14/70521* (2013.01); *A61K 38/00* (2013.01); *C07K 2319/30* (2013.01)

(58) Field of Classification Search
CPC .......... C07K 14/70521; C07K 2319/30; A61K 38/00
USPC ............. 424/134.1; 541/1.1; 530/350, 387.3
See application file for complete search history.

(56) References Cited

U.S. PATENT DOCUMENTS

| | | | |
|---|---|---|---|
| 8,642,557 B2 * | 2/2014 | Akamatsu | A61K 47/48246 514/21.2 |
| 9,587,007 B2 * | 3/2017 | Akamatsu | C07K 14/70521 |
| 2011/0130546 A1 | 2/2011 | Karrer et al. | |
| 2011/0287032 A1 | 11/2011 | Lazar et al. | |
| 2011/0305712 A1 | 12/2011 | Akamatsu et al. | |
| 2012/0052065 A1 | 1/2012 | Peach et al. | |

FOREIGN PATENT DOCUMENTS

| WO | WO 01/92337 A2 | 12/2001 |
|---|---|---|
| WO | WO 2008/047150 A2 | 4/2008 |
| WO | WO 2009/058564 A2 | 5/2009 |

OTHER PUBLICATIONS

Ibragimova and Eade (Biophysical Journal, Oct. 1999, vol. 77, pp. 2191-2198).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987)).*
Lin et al Biochemistry USA vol. 14:1559-1563 (1975)).*
NCIMB website search (p. 1; Mar. 13, 2017; accession No. 41948).*
International Search Report dated Jul. 22, 2013, in corresponding International Application No. PCT/US13/30179.
International Preliminary Report on Patentability dated Nov. 11, 2014, in corresponding International Application No. PCT/US13/30179.
Morton, Phillip A., et al., "Differential Effects of CTLA-4 Substitutions on the Binding of Human CD80 (B7-1) and CD86 (B7-2)," *The Journal of Immunology*, 156:1047-1054 (1996).
Stamper, Carin C., et al., "Crystal Structure of the B7-1/CTLA-4 Comlex that Inhibits Human Immune Responses," *Nature* 410:608-611 (2001).
Van Den Beucken, T., et al., "Building Novel Binding Ligands to B7.1 and B7.2 Based on Human Antibody Single Variable Light Chain Domains," *Journal of Molecular Biology*, 301:591-601 (2001).

* cited by examiner

*Primary Examiner* — Lynn A Bristol

(57) ABSTRACT

Variants of cytotoxic T-lymphocyte antigen 4 (CTLA-4) with high affinity, potency and stability. Formulations of CTLA-4 variants at high concentration for subcutaneous or intravenous administration, e.g. at monthly or less frequent dosage intervals. Use of CTLA-4 variants for treating rheumatoid arthritis and other inflammatory disorders. Fusion of CTLA-4 with IgG Fc having improved stability and longer in vivo half-life.

15 Claims, 7 Drawing Sheets

Figure 1

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| M | H | V | A | Q | P | A | V | V | L | A | S | S | R | G | $R_{16}$ | A | S | F | V |
| 21 | 22 | 23 | 24 | 25 | 26 | 27 | 28 | 29 | 30 | 31 | 32 | 33 | 34 | 35 | 36 | 37 | 38 | 39 | 40 |
| C | E | Y | $R_{24}$ | N | F | $R_{27}$ | K | A | T | E | V | R | V | T | V | L | R | Q | A |
| 41 | 42 | 43 | 44 | 45 | 46 | 47 | 48 | 49 | 50 | 51 | 52 | 53 | 54 | 55 | 56 | 57 | 58 | 59 | 60 |
| D | S | Q | V | T | E | V | C | A | A | T | Y | M | $R_{54}$ | G | $R_{56}$ | E | $R_{58}$ | $R_{59}$ | $R_{60}$ |
| 61 | 62 | 63 | 64 | 65 | 66 | 67 | 68 | 69 | 70 | 71 | 72 | 73 | 74 | 75 | 76 | 77 | 78 | 79 | 80 |
| $R_{61}$ | D | $R_{63}$ | $R_{64}$ | $R_{65}$ | C | T | G | T | $R_{70}$ | S | G | N | Q | V | N | L | T | I | $R_{80}$ |
| 81 | 82 | 83 | 84 | 85 | 86 | 87 | 88 | 89 | 90 | 91 | 92 | 93 | 94 | 95 | 96 | 97 | 98 | 99 | 100 |
| G | L | R | A | $R_{85}$ | L | T | G | L | Y | H | C | $R_{93}$ | V | E | L | M | Y | P | P |
| 101 | 102 | 103 | 104 | 105 | 106 | 107 | 108 | 109 | 110 | 111 | 112 | 113 | 114 | 115 | 116 | 117 | 118 | 119 | 120 |
| P | Y | Y | L | G | I | G | N | G | T | Q | I | Y | V | I | D | P | E | P | C |
| 121 | 122 | 123 | 124 | | | | | | | | | | | | | | | | |
| P | D | S | D | | | | | | | | | | | | | | | | |

```
                            SEQUENCE LISTING

<160> NUMBER OF SEQ ID NOS: 72

<210> SEQ ID NO 1
<211> LENGTH: 274
<212> TYPE: PRT
<213> ORGANISM: Artificial sequence
<220> FEATURE:
<223> OTHER INFORMATION: Synthetic sequence: Human CD80 flag his 10

<400> SEQUENCE: 1

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Asp Pro Ala Phe Leu Tyr Lys Val Val Gly Ala Ala Asp Tyr
                245                 250                 255

Lys Asp Asp Asp Asp Lys Ala Ala His His His His His His His His
            260                 265                 270

His His

<210> SEQ ID NO 2
<211> LENGTH: 277
<212> TYPE: PRT
<213> ORGANISM: Artificial sequence
<220> FEATURE:
<223> OTHER INFORMATION: Synthetic sequence: Mouse CD80 flag his 10
```

-continued

<400> SEQUENCE: 2

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Lys Pro Pro Glu Asp
225                 230                 235                 240

Pro Pro Asp Ser Lys Tyr Pro Ala Phe Leu Tyr Lys Val Val Gly Ala
                245                 250                 255

Ala Asp Tyr Lys Asp Asp Asp Lys Ala Ala His His His His His
            260                 265                 270

His His His His His
        275

<210> SEQ ID NO 3
<211> LENGTH: 274
<212> TYPE: PRT
<213> ORGANISM: Artificial sequence
<220> FEATURE:
<223> OTHER INFORMATION: Synthetic sequence: Cynomolgus CD80 flag his 10

<400> SEQUENCE: 3

Met Gly His Thr Trp Arg Gln Gly Ile Ser Pro Ser Lys Cys Pro Tyr
1               5                   10                  15

Leu Lys Phe Phe Gln Leu Leu Val Leu Ala Cys Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Met Val Leu Thr Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Met Leu Ser Val Lys Ala Asp Phe Pro Thr
    130                 135                 140

Pro Ser Ile Thr Asp Phe Glu Ile Pro Pro Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Ser Thr Thr Val Ser Gln Asp
            180                 185                 190

Pro Glu Thr Glu Leu Tyr Thr Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Pro Lys Gln Glu His Phe Pro
225                 230                 235                 240

Asp Asn Asp Pro Ala Phe Leu Tyr Lys Val Val Gly Ala Ala Asp Tyr
                245                 250                 255

Lys Asp Asp Asp Asp Lys Ala Ala His His His His His His His His
            260                 265                 270

His His

<210> SEQ ID NO 4
<211> LENGTH: 271
<212> TYPE: PRT
<213> ORGANISM: Artificial sequence
<220> FEATURE:
<223> OTHER INFORMATION: Synthetic sequence: Human CD86 flag his 10

<400> SEQUENCE: 4

Met Gly Leu Ser Asn Ile Leu Phe Val Met Ala Phe Leu Leu Ser Gly
1               5                   10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Gln Ser Leu Ser Glu Leu Val
        35                  40                  45

Val Phe Trp Gln Asp Gln Glu Asn Leu Val Leu Asn Glu Val Tyr Leu
    50                  55                  60

Gly Lys Glu Lys Phe Asp Ser Val His Ser Lys Tyr Met Gly Arg Thr
65                  70                  75                  80

Ser Phe Asp Ser Asp Ser Trp Thr Leu Arg Leu His Asn Leu Gln Ile
                85                  90                  95

Lys Asp Lys Gly Leu Tyr Gln Cys Ile Ile His His Lys Lys Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
    130                 135                 140

Val Tyr Ile Asn Leu Thr Cys Ser Ser Ile His Gly Tyr Pro Glu Pro

```
                145                 150                 155                 160
Lys Lys Met Ser Val Leu Leu Arg Thr Lys Asn Ser Thr Ile Glu Tyr
                    165                 170                 175
Asp Gly Ile Met Gln Lys Ser Gln Asp Asn Val Thr Glu Leu Tyr Asp
                180                 185                 190
Val Ser Ile Ser Leu Ser Val Ser Phe Pro Asp Val Thr Ser Asn Met
                195                 200                 205
Thr Ile Phe Cys Ile Leu Glu Thr Asp Lys Thr Arg Leu Leu Ser Ser
            210                 215                 220
Pro Phe Ser Ile Glu Leu Glu Asp Pro Gln Pro Pro Pro Asp His Asp
225                 230                 235                 240
Pro Ala Phe Leu Tyr Lys Val Val Gly Ala Ala Asp Tyr Lys Asp Asp
                    245                 250                 255
Asp Asp Lys Ala Ala His His His His His His His His His
                260                 265                 270

<210> SEQ ID NO 5
<211> LENGTH: 277
<212> TYPE: PRT
<213> ORGANISM: Artificial sequence
<220> FEATURE:
<223> OTHER INFORMATION: Synthetic sequence: Mouse CD86 flag his 10

<400> SEQUENCE: 5

Met Asp Pro Arg Cys Thr Met Gly Leu Ala Ile Leu Ile Phe Val Thr
1               5                   10                  15
Val Leu Leu Ile Ser Asp Ala Val Ser Val Glu Thr Gln Ala Tyr Phe
                20                  25                  30
Asn Gly Thr Ala Tyr Leu Pro Cys Pro Phe Thr Lys Ala Gln Asn Ile
            35                  40                  45
Ser Leu Ser Glu Leu Val Val Phe Trp Gln Asp Gln Gln Lys Leu Val
        50                  55                  60
Leu Tyr Glu His Tyr Leu Gly Thr Glu Lys Leu Asp Ser Val Asn Ala
65                  70                  75                  80
Lys Tyr Leu Gly Arg Thr Ser Phe Asp Arg Asn Asn Trp Thr Leu Arg
                85                  90                  95
Leu His Asn Val Gln Ile Lys Asp Met Gly Ser Tyr Asp Cys Phe Ile
                100                 105                 110
Gln Lys Lys Pro Pro Thr Gly Ser Ile Ile Leu Gln Gln Thr Leu Thr
            115                 120                 125
Glu Leu Ser Val Ile Ala Asn Phe Ser Glu Pro Glu Ile Lys Leu Ala
        130                 135                 140
Gln Asn Val Thr Gly Asn Ser Gly Ile Asn Leu Thr Cys Thr Ser Lys
145                 150                 155                 160
Gln Gly His Pro Lys Pro Lys Lys Met Tyr Phe Leu Ile Thr Asn Ser
                165                 170                 175
Thr Asn Glu Tyr Gly Asp Asn Met Gln Ile Ser Gln Asp Asn Val Thr
                180                 185                 190
Glu Leu Phe Ser Ile Ser Asn Ser Leu Ser Leu Ser Phe Pro Asp Gly
            195                 200                 205
Val Trp His Met Thr Val Val Cys Val Leu Glu Thr Glu Ser Met Lys
        210                 215                 220
Ile Ser Ser Lys Pro Leu Asn Phe Thr Gln Glu Phe Pro Ser Pro Gln
225                 230                 235                 240
Thr Tyr Trp Lys Glu Tyr Pro Ala Phe Leu Tyr Lys Val Val Gly Ala
```

245                 250                 255

Ala Asp Tyr Lys Asp Asp Asp Lys Ala Ala His His His His
              260                 265                 270

His His His His His
        275

<210> SEQ ID NO 6
<211> LENGTH: 271
<212> TYPE: PRT
<213> ORGANISM: Artificial sequence
<220> FEATURE:
<223> OTHER INFORMATION: Synthetic sequence: Cynomolgus CD86 flag his 10

<400> SEQUENCE: 6

Met Gly Leu Ser Asn Thr Leu Phe Val Met Ala Phe Leu Leu Ser Gly
1               5                   10                  15

Ala Ala Pro Leu Lys Ile Gln Ala Tyr Phe Asn Glu Thr Ala Asp Leu
            20                  25                  30

Pro Cys Gln Phe Ala Asn Ser Gln Asn Arg Ser Leu Ser Glu Leu Val
        35                  40                  45

Val Phe Trp Gln Asn Gln Glu Asn Leu Val Leu Asn Glu Val Tyr Leu
    50                  55                  60

Gly Lys Glu Lys Phe Asp Ser Val His Ser Lys Tyr Met Gly Arg Thr
65                  70                  75                  80

Ser Phe Asp Pro Glu Ser Trp Thr Leu Arg Leu His Asn Leu Gln Ile
                85                  90                  95

Lys Asp Lys Gly Leu Tyr Gln Cys Ile Ile His His Lys Arg Pro Thr
            100                 105                 110

Gly Met Ile Arg Ile His Gln Met Asn Ser Glu Leu Ser Val Leu Ala
        115                 120                 125

Asn Phe Ser Gln Pro Glu Ile Val Pro Ile Ser Asn Ile Thr Glu Asn
    130                 135                 140

Met Tyr Ile Asn Leu Thr Cys Ser Ser Ile His Gly Tyr Pro Glu Pro
145                 150                 155                 160

Glu Lys Met Ser Val Leu Leu Arg Thr Lys Asn Ser Thr Ile Glu Tyr
                165                 170                 175

Asp Gly Val Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
        195                 200                 205

Thr Ile Phe Cys Val Leu Glu Thr Asp Lys Thr Gln Leu Leu Ser Ser
    210                 215                 220

Pro Phe Ser Ile Glu Leu Glu Asp Pro Gln Pro Pro Asp His Asp
225                 230                 235                 240

Pro Ala Phe Leu Tyr Lys Val Val Gly Ala Ala Asp Tyr Lys Asp Asp
                245                 250                 255

Asp Asp Lys Ala Ala His His His His His His His His His His
            260                 265                 270

<210> SEQ ID NO 7
<211> LENGTH: 357
<212> TYPE: PRT
<213> ORGANISM: Artificial sequence
<220> FEATURE:
<223> OTHER INFORMATION: Synthetic sequence: CTLA4 Fc variant-1 [Wild
      type CTLA-4 IgG1 Fc (modified hinge)]

<400> SEQUENCE: 7

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355
```

<210> SEQ ID NO 8
<211> LENGTH: 357
<212> TYPE: PRT
<213> ORGANISM: Artificial sequence
<220> FEATURE:
<223> OTHER INFORMATION: Synthetic sequence: CTLA4 Fc variant-2 [Wild type CTLA-4 IgG1 Fc (modified hinge) with YTE]

<400> SEQUENCE: 8

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Tyr Ile Thr Arg Glu Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355
```

<210> SEQ ID NO 9
<211> LENGTH: 357
<212> TYPE: PRT
<213> ORGANISM: Artificial sequence
<220> FEATURE:
<223> OTHER INFORMATION: Synthetic sequence: CTLA4 Fc variant-3 [Wild type CTLA-4 IgG1 Fc with TM and YTE]

<400> SEQUENCE: 9

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Val Glu Pro Lys
        115                 120                 125

Ser Cys Asp Lys Thr His Thr Cys Pro Pro Cys Pro Ala Pro Glu Phe
    130                 135                 140

Glu Gly Gly Pro Ser Val Phe Leu Phe Pro Pro Lys Pro Lys Asp Thr
145                 150                 155                 160

Leu Tyr Ile Thr Arg Glu Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Ser Ile Glu Lys Thr Ile Ser Lys Ala Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355
```

<210> SEQ ID NO 10
<211> LENGTH: 354
<212> TYPE: PRT
<213> ORGANISM: Artificial sequence
<220> FEATURE:
<223> OTHER INFORMATION: Synthetic sequence: CTLA4 Fc variant-4 [Wild type CTLA-4 IgG4 Fc with YTE and hinge Proline]

<400> SEQUENCE: 10

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Val Glu Ser Lys
        115                 120                 125

Tyr Gly Pro Pro Cys Pro Pro Cys Pro Ala Pro Glu Phe Leu Gly Gly
    130                 135                 140

Pro Ser Val Phe Leu Phe Pro Pro Lys Pro Lys Asp Thr Leu Tyr Ile
145                 150                 155                 160

Thr Arg Glu Pro Glu Val Thr Cys Val Val Val Asp Val Ser Gln Glu
                165                 170                 175

Asp Pro Glu Val Gln Phe Asn Trp Tyr Val Asp Gly Val Glu Val His
            180                 185                 190

Asn Ala Lys Thr Lys Pro Arg Glu Glu Gln Phe Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Gly Leu Pro Ser Ser Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Gln Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Arg Leu Thr Val Asp
305                 310                 315                 320

Lys Ser Arg Trp Gln Glu Gly Asn Val Phe Ser Cys Ser Val Met His
                325                 330                 335

Glu Ala Leu His Asn His Tyr Thr Gln Lys Ser Leu Ser Leu Ser Leu
            340                 345                 350

Gly Lys

<210> SEQ ID NO 11
<211> LENGTH: 357
<212> TYPE: PRT
<213> ORGANISM: Artificial sequence
<220> FEATURE:
<223> OTHER INFORMATION: Synthetic sequence: CTLA-4 Variant 1322 IgG1 Fc with TM and YTE (357aa)

<400> SEQUENCE: 11

Met His Val Ala Gln Pro Ala Val Val Leu Ala Ser Ser Arg Gly Ile
1               5                   10                  15

Ala Ser Phe Val Cys Glu Tyr Ala Asn Pro Ser Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Lys Gly Ser Glu Leu Ser Thr Gln Asp Tyr Pro
50                  55                  60

Asn Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Val Glu Pro Lys
        115                 120                 125

Ser Cys Asp Lys Thr His Thr Cys Pro Pro Cys Pro Ala Pro Glu Phe
130                 135                 140

Glu Gly Gly Pro Ser Val Phe Leu Phe Pro Pro Lys Pro Lys Asp Thr
145                 150                 155                 160

Leu Tyr Ile Thr Arg Glu Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Ser Ile Glu Lys Thr Ile Ser Lys Ala Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 12
<211> LENGTH: 357
<212> TYPE: PRT
<213> ORGANISM: Artificial sequence
<220> FEATURE:

<223> OTHER INFORMATION: Synthetic sequence: CTLA-4 Variant 1321 IgG1 Fc
      with TM and YTE (357aa)

<400> SEQUENCE: 12

Met His Val Ala Gln Pro Ala Val Val Leu Ala Ser Ser Arg Gly Ser
1               5                   10                  15

Ala Ser Phe Val Cys Glu Tyr Ala Asn Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Lys Gly Asn Glu Gly Thr Phe Leu Asp Asp Ser
    50                  55                  60

Ile Cys Thr Gly Thr Ala Ser Gly Asn Gln Val Asn Leu Thr Ile Arg
65                  70                  75                  80

Gly Leu Arg Ala Ser Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Val Glu Pro Lys
        115                 120                 125

Ser Cys Asp Lys Thr His Thr Cys Pro Pro Cys Pro Ala Pro Glu Phe
    130                 135                 140

Glu Gly Gly Pro Ser Val Phe Leu Phe Pro Pro Lys Pro Lys Asp Thr
145                 150                 155                 160

Leu Tyr Ile Thr Arg Glu Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Ser Ile Glu Lys Thr Ile Ser Lys Ala Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 13
<211> LENGTH: 357
<212> TYPE: PRT
<213> ORGANISM: Artificial sequence
<220> FEATURE:
<223> OTHER INFORMATION: Synthetic sequence: CTLA-4 Variant 1299 IgG1 Fc
      with TM and YTE (357aa)

<400> SEQUENCE: 13

```
Met His Val Ala Gln Pro Ala Val Val Leu Ala Ser Ser Arg Gly Arg
1               5                   10                  15

Ala Ser Phe Val Cys Glu Tyr Thr Asn Pro Ser Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Ala Thr Phe Leu Asp Asp Ser
50                  55                  60

Ile Cys Thr Gly Thr Ala Ser Gly Asn Gln Val Asn Leu Thr Ile Gln
65                  70                  75                  80

Gly Leu Arg Ala Gln Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Val Glu Pro Lys
        115                 120                 125

Ser Cys Asp Lys Thr His Thr Cys Pro Pro Cys Pro Ala Pro Glu Phe
130                 135                 140

Glu Gly Gly Pro Ser Val Phe Leu Phe Pro Pro Lys Pro Lys Asp Thr
145                 150                 155                 160

Leu Tyr Ile Thr Arg Glu Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Ser Ile Glu Lys Thr Ile Ser Lys Ala Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355
```

<210> SEQ ID NO 14
<211> LENGTH: 357
<212> TYPE: PRT

<213> ORGANISM: Artificial sequence
<220> FEATURE:
<223> OTHER INFORMATION: Synthetic sequence: CTLA-4 Variant 1315 IgG1 Fc
      with TM and YTE (357aa)

<400> SEQUENCE: 14

```
Met His Val Ala Gln Pro Ala Val Val Leu Ala Ser Ser Arg Gly Ser
1               5                   10                  15
Ala Ser Phe Val Cys Glu Tyr Ala Asn Pro Gly Lys Ala Thr Glu Val
            20                  25                  30
Arg Val Thr Val Leu Arg Gln Ala Asp Ser Gln Val Thr Glu Val Cys
        35                  40                  45
Ala Ala Thr Tyr Met Met Gly Asn Glu Gly Thr Phe Leu Asp Asp Ser
    50                  55                  60
Ile Cys Thr Gly Thr Ala Ser Gly Asn Gln Val Asn Leu Thr Ile Arg
65                  70                  75                  80
Gly Leu Arg Ala Ser Asp Thr Gly Leu Tyr Ile Cys Gln Val Glu Leu
                85                  90                  95
Met Tyr Pro Pro Pro Tyr Tyr Leu Gly Ile Gly Asn Gly Thr Gln Ile
            100                 105                 110
Tyr Val Ile Asp Pro Glu Pro Cys Pro Asp Ser Asp Val Glu Pro Lys
        115                 120                 125
Ser Cys Asp Lys Thr His Thr Cys Pro Pro Cys Pro Ala Pro Glu Phe
    130                 135                 140
Glu Gly Gly Pro Ser Val Phe Leu Phe Pro Pro Lys Pro Lys Asp Thr
145                 150                 155                 160
Leu Tyr Ile Thr Arg Glu Pro Glu Val Thr Cys Val Val Val Asp Val
                165                 170                 175
Ser His Glu Asp Pro Glu Val Lys Phe Asn Trp Tyr Val Asp Gly Val
            180                 185                 190
Glu Val His Asn Ala Lys Thr Lys Pro Arg Glu Glu Gln Tyr Asn Ser
        195                 200                 205
Thr Tyr Arg Val Val Ser Val Leu Thr Val Leu His Gln Asp Trp Leu
    210                 215                 220
Asn Gly Lys Glu Tyr Lys Cys Lys Val Ser Asn Lys Ala Leu Pro Ala
225                 230                 235                 240
Ser Ile Glu Lys Thr Ile Ser Lys Ala Lys Gly Gln Pro Arg Glu Pro
                245                 250                 255
Gln Val Tyr Thr Leu Pro Pro Ser Arg Glu Glu Met Thr Lys Asn Gln
            260                 265                 270
Val Ser Leu Thr Cys Leu Val Lys Gly Phe Tyr Pro Ser Asp Ile Ala
        275                 280                 285
Val Glu Trp Glu Ser Asn Gly Gln Pro Glu Asn Asn Tyr Lys Thr Thr
    290                 295                 300
Pro Pro Val Leu Asp Ser Asp Gly Ser Phe Phe Leu Tyr Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
            340                 345                 350
Leu Ser Pro Gly Lys
            355
```

<210> SEQ ID NO 15
<211> LENGTH: 357

<212> TYPE: PRT
<213> ORGANISM: Artificial sequence
<220> FEATURE:
<223> OTHER INFORMATION: Synthetic sequence: CTLA-4 Variant 1115 IgG1 Fc
      with TM and YTE (357aa)

<400> SEQUENCE: 15

Met His Val Ala Gln Pro Ala Val Val Leu Ala Ser Ser Arg Gly Val
1               5                   10                  15

Ala Ser Phe Val Cys Glu Tyr Ala Asn Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Gly Thr Phe Leu Asp Asp Ser
50                  55                  60

Ile Cys Thr Gly Thr Ala Ser Gly Asn Gln Val Asn Leu Thr Ile Gln
65                  70                  75                  80

Gly Leu Arg Ala Gln Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Val Glu Pro Lys
        115                 120                 125

Ser Cys Asp Lys Thr His Thr Cys Pro Pro Cys Pro Ala Pro Glu Phe
130                 135                 140

Glu Gly Gly Pro Ser Val Phe Leu Phe Pro Pro Lys Pro Lys Asp Thr
145                 150                 155                 160

Leu Tyr Ile Thr Arg Glu Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
210                 215                 220

Asn Gly Lys Glu Tyr Lys Cys Lys Val Ser Asn Lys Ala Leu Pro Ala
225                 230                 235                 240

Ser Ile Glu Lys Thr Ile Ser Lys Ala Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 16

<211> LENGTH: 357
<212> TYPE: PRT
<213> ORGANISM: Artificial sequence
<220> FEATURE:
<223> OTHER INFORMATION: Synthetic sequence: CTLA-4 Variant 1227 IgG1 Fc
      with TM and YTE (357aa)

<400> SEQUENCE: 16

Met His Val Ala Gln Pro Ala Val Val Leu Ala Ser Ser Arg Gly Ser
1               5                   10                  15

Ala Ser Phe Val Cys Glu Tyr Ala Asn Pro Ser Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Ala Thr Phe Leu Asp Asp Ser
    50                  55                  60

Ile Cys Thr Gly Thr Ala Ser Gly Asn Gln Val Asn Leu Thr Ile Gln
65                  70                  75                  80

Gly Leu Arg Ala Gln Asp Thr Gly Leu Tyr Ile Cys His Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Val Glu Pro Lys
        115                 120                 125

Ser Cys Asp Lys Thr His Thr Cys Pro Pro Cys Pro Ala Pro Glu Phe
    130                 135                 140

Glu Gly Gly Pro Ser Val Phe Leu Phe Pro Pro Lys Pro Lys Asp Thr
145                 150                 155                 160

Leu Tyr Ile Thr Arg Glu Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Ser Ile Glu Lys Thr Ile Ser Lys Ala Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 17
<211> LENGTH: 456
<212> TYPE: PRT
<213> ORGANISM: Artificial sequence
<220> FEATURE:
<223> OTHER INFORMATION: Synthetic sequence: NIP 74 heavy chain (for tetramer)

<400> SEQUENCE: 17

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Gly Tyr Asp Tyr Gly Ser Gly Ser Tyr Tyr Tyr Tyr
            100                 105                 110

Gly Met Asp Val Trp Gly Lys Gly Thr Met Val Thr Val Thr Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365
```

```
Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
    450                 455

<210> SEQ ID NO 18
<211> LENGTH: 217
<212> TYPE: PRT
<213> ORGANISM: Artificial sequence
<220> FEATURE:
<223> OTHER INFORMATION: Synthetic sequence: NIP 74 light chain (for
      tetramer)

<400> SEQUENCE: 18

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Asp Val Val Phe Gly Gly Gly Thr Lys Leu Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 19
<211> LENGTH: 608
<212> TYPE: PRT
<213> ORGANISM: Artificial sequence
<220> FEATURE:
<223> OTHER INFORMATION: Synthetic sequence: CTLA-4 tetramer heavy chain
```

<400> SEQUENCE: 19

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Gly Ser Gly
        115                 120                 125

Ser Ala Thr Gly Gly Ser Gly Ser Thr Ala Ser Ser Gly Ser Gly Ser
    130                 135                 140

Ala Thr Gly Gly Gly Gly Gly Gln Val Gln Leu Val Gln Ser Gly
145                 150                 155                 160

Ala Glu Val Lys Lys Pro Gly Ala Ser Val Lys Val Ser Cys Lys Ala
                165                 170                 175

Ser Gly Tyr Thr Phe Thr Gly Tyr Tyr Met His Trp Val Arg Gln Ala
            180                 185                 190

Pro Gly Gln Gly Leu Glu Trp Met Gly Trp Ile Asn Pro Asn Ser Gly
        195                 200                 205

Gly Thr Asn Tyr Ala Gln Lys Phe Gln Gly Arg Val Thr Met Thr Arg
    210                 215                 220

Asp Thr Ser Ile Ser Thr Ala Tyr Met Glu Leu Ser Arg Leu Arg Ser
225                 230                 235                 240

Asp Asp Thr Ala Val Tyr Tyr Cys Ala Arg Arg Gly Tyr Asp Tyr Gly
                245                 250                 255

Ser Gly Ser Tyr Tyr Tyr Tyr Gly Met Asp Val Trp Gly Lys Gly
            260                 265                 270

Thr Met Val Thr Val Thr Ala Ser Thr Lys Gly Pro Ser Val Phe Pro
        275                 280                 285

Leu Ala Pro Ser Ser Lys Ser Thr Ser Gly Gly Thr Ala Ala Leu Gly
    290                 295                 300

Cys Leu Val Lys Asp Tyr Phe Pro Glu Pro Val Thr Val Ser Trp Asn
305                 310                 315                 320

Ser Gly Ala Leu Thr Ser Gly Val His Thr Phe Pro Ala Val Leu Gln
                325                 330                 335

Ser Ser Gly Leu Tyr Ser Leu Ser Ser Val Val Thr Val Pro Ser Ser
            340                 345                 350

Ser Leu Gly Thr Gln Thr Tyr Ile Cys Asn Val Asn His Lys Pro Ser
        355                 360                 365

Asn Thr Lys Val Asp Lys Lys Val Glu Pro Lys Ser Cys Asp Lys Thr
    370                 375                 380

His Thr Cys Pro Pro Cys Pro Ala Pro Glu Leu Leu Gly Gly Pro Ser
385                 390                 395                 400

Val Phe Leu Phe Pro Pro Lys Pro Lys Asp Thr Leu Met Ile Ser Arg
                405                 410                 415
```

```
Thr Pro Glu Val Thr Cys Val Val Asp Val Ser His Glu Asp Pro
            420                 425                 430

Glu Val Lys Phe Asn Trp Tyr Val Asp Gly Val Glu Val His Asn Ala
        435                 440                 445

Lys Thr Lys Pro Arg Glu Glu Gln Tyr Asn Ser Thr Tyr Arg Val Val
    450                 455                 460

Ser Val Leu Thr Val Leu His Gln Asp Trp Leu Asn Gly Lys Glu Tyr
465                 470                 475                 480

Lys Cys Lys Val Ser Asn Lys Ala Leu Pro Ala Pro Ile Glu Lys Thr
                485                 490                 495

Ile Ser Lys Ala Lys Gly Gln Pro Arg Glu Pro Gln Val Tyr Thr Leu
            500                 505                 510

Pro Pro Ser Arg Glu Glu Met Thr Lys Asn Gln Val Ser Leu Thr Cys
        515                 520                 525

Leu Val Lys Gly Phe Tyr Pro Ser Asp Ile Ala Val Glu Trp Glu Ser
    530                 535                 540

Asn Gly Gln Pro Glu Asn Asn Tyr Lys Thr Thr Pro Pro Val Leu Asp
545                 550                 555                 560

Ser Asp Gly Ser Phe Phe Leu Tyr Ser Lys Leu Thr Val Asp Lys Ser
                565                 570                 575

Arg Trp Gln Gln Gly Asn Val Phe Ser Cys Ser Val Met His Glu Ala
            580                 585                 590

Leu His Asn His Tyr Thr Gln Lys Ser Leu Ser Leu Ser Pro Gly Lys
        595                 600                 605

<210> SEQ ID NO 20
<211> LENGTH: 369
<212> TYPE: PRT
<213> ORGANISM: Artificial sequence
<220> FEATURE:
<223> OTHER INFORMATION: Synthetic sequence: CTLA-4 tetramer light chain

<400> SEQUENCE: 20

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Gly Ser Gly
        115                 120                 125

Ser Thr Ala Gly Gly Ser Gly Ser Ala Thr Ser Ser Gly Ser Gly Ser
    130                 135                 140

Ala Thr Gly Gly Gly Gly Gly Gln Ser Val Val Thr Gln Pro Pro
145                 150                 155                 160

Ser Val Ser Gly Ala Pro Gly Gln Arg Val Thr Ile Ser Cys Thr Gly
                165                 170                 175
```

-continued

```
Ser Ser Ser Asn Ile Gly Ala Gly Tyr Asp Val His Trp Tyr Gln Gln
            180                 185                 190

Leu Pro Gly Thr Ala Pro Lys Leu Leu Ile Tyr Gly Asn Ser Asn Arg
        195                 200                 205

Pro Ser Gly Val Pro Asp Arg Phe Ser Gly Ser Lys Ser Gly Thr Ser
    210                 215                 220

Ala Ser Leu Ala Ile Thr Gly Leu Gln Ala Glu Asp Glu Ala Asp Tyr
225                 230                 235                 240

Tyr Cys Gln Ser Tyr Asp Ser Ser Leu Ser Asp Val Val Phe Gly Gly
                245                 250                 255

Gly Thr Lys Leu Thr Val Leu Gly Gln Pro Lys Ala Asn Pro Thr Val
            260                 265                 270

Thr Leu Phe Pro Pro Ser Ser Glu Glu Leu Gln Ala Asn Lys Ala Thr
        275                 280                 285

Leu Val Cys Leu Ile Ser Asp Phe Tyr Pro Gly Ala Val Thr Val Ala
    290                 295                 300

Trp Lys Ala Asp Gly Ser Pro Val Lys Ala Gly Val Glu Thr Thr Lys
305                 310                 315                 320

Pro Ser Lys Gln Ser Asn Asn Lys Tyr Ala Ala Ser Ser Tyr Leu Ser
                325                 330                 335

Leu Thr Pro Glu Gln Trp Lys Ser His Arg Ser Tyr Ser Cys Gln Val
            340                 345                 350

Thr His Glu Gly Ser Thr Val Glu Lys Thr Val Ala Pro Thr Glu Cys
        355                 360                 365

Ser
```

```
<210> SEQ ID NO 21
<211> LENGTH: 22
<212> TYPE: DNA
<213> ORGANISM: Artificial sequence
<220> FEATURE:
<223> OTHER INFORMATION: Synthetic sequence: 5prime oligonucleotide for
      amplification of CTLA4 for fusion to NIP74 VH

<400> SEQUENCE: 21
gcttgcgcgc actccgcaat gc                                              22

<210> SEQ ID NO 22
<211> LENGTH: 22
<212> TYPE: DNA
<213> ORGANISM: Artificial sequence
<220> FEATURE:
<223> OTHER INFORMATION: Synthetic sequence: 3prime oligonucleotide for
      amplification of CTLA4 for fusion to NIP74 VH

<400> SEQUENCE: 22
ccagaaccag aagaagcggt ag                                              22

<210> SEQ ID NO 23
<211> LENGTH: 23
<212> TYPE: DNA
<213> ORGANISM: Artificial sequence
<220> FEATURE:
<223> OTHER INFORMATION: Synthetic sequence: 5prime oligonucleotide for
      amplification of CTLA4 for fusion to NIP74 VL

<400> SEQUENCE: 23
gcttgtgcac tccgcaatgc acg                                             23
```

<210> SEQ ID NO 24
<211> LENGTH: 23
<212> TYPE: DNA
<213> ORGANISM: Artificial sequence
<220> FEATURE:
<223> OTHER INFORMATION: Synthetic sequence: 3prime oligonucleotide for
      amplification of CTLA4 for fusion to NIP74 VL

<400> SEQUENCE: 24
gagccagaag aggtagcaga acc                                             23

<210> SEQ ID NO 25
<211> LENGTH: 70
<212> TYPE: DNA
<213> ORGANISM: Artificial sequence
<220> FEATURE:
<223> OTHER INFORMATION: Synthetic sequence: 5prime oligonucleotide for
      amplification of NIP74 VH for CTLA4 fusion

<400> SEQUENCE: 25
ctaccgcttc ttctggttct ggttctgcta ccggtggtgg tggtggtggc caggtgcagc      60
tggtgcagtc                                                            70

<210> SEQ ID NO 26
<211> LENGTH: 18
<212> TYPE: DNA
<213> ORGANISM: Artificial sequence
<220> FEATURE:
<223> OTHER INFORMATION: Synthetic sequence: 3prime oligonucleotide for
      amplification of NIP74 VH for CTLA4 fusion

<400> SEQUENCE: 26 ccaggggggaa gaccgatg                                                  18

<210> SEQ ID NO 27
<211> LENGTH: 74
<212> TYPE: DNA
<213> ORGANISM: Artificial sequence
<220> FEATURE:
<223> OTHER INFORMATION: Synthetic sequence: 5prime oligonucleotide for
      amplification of NIP74 VL for CTLA4 fusion

<400> SEQUENCE: 27
ggttctgcta cctcttctgg ctctggttct gcgaccggtg gtggcggtgg tggccagtct      60
gtcgtgacgc agcc                                                       74

<210> SEQ ID NO 28
<211> LENGTH: 53
<212> TYPE: DNA
<213> ORGANISM: Artificial sequence
<220> FEATURE:
<223> OTHER INFORMATION: Synthetic sequence: 3prime oligonucleotide for
      amplification of NIP74 VL for CTLA4 fusion

<400> SEQUENCE: 28
gcacttaatt aagttagatc tattctgact cacctaggac ggtcagcttg gtc             53

<210> SEQ ID NO 29
<211> LENGTH: 22
<212> TYPE: DNA
<213> ORGANISM: Artificial sequence
<220> FEATURE:
<223> OTHER INFORMATION: Synthetic sequence: 5prime oligonucleotide for
      assembly of CTLA4 - NIP74 VH fusion

<400> SEQUENCE: 29
gcttgcgcgc actccgcaat gc                                           22

<210> SEQ ID NO 30
<211> LENGTH: 18
<212> TYPE: DNA
<213> ORGANISM: Artificial sequence
<220> FEATURE:
<223> OTHER INFORMATION: Synthetic sequence: 3prime oligonucleotide for
      assembly of CTLA4 - NIP74 VH fusion

<400> SEQUENCE: 30 ccaggggaa gaccgatg                                                 18

<210> SEQ ID NO 31
<211> LENGTH: 23
<212> TYPE: DNA
<213> ORGANISM: Artificial sequence
<220> FEATURE:
<223> OTHER INFORMATION: Synthetic sequence: 5prime oligonucleotide for
      assembly of CTLA4 - NIP74 VL fusion

<400> SEQUENCE: 31
gcttgtgcac tccgcaatgc acg                                          23

<210> SEQ ID NO 32
<211> LENGTH: 53
<212> TYPE: DNA
<213> ORGANISM: Artificial sequence
<220> FEATURE:
<223> OTHER INFORMATION: Synthetic sequence: 3prime oligonucleotide for
      assembly of CTLA4 - NIP74 VL fusion

<400> SEQUENCE: 32
gcacttaatt aagttagatc tattctgact cacctaggac ggtcagcttg gtc          53

<210> SEQ ID NO 33
<211> LENGTH: 64
<212> TYPE: DNA
<213> ORGANISM: Artificial sequence
<220> FEATURE:
<223> OTHER INFORMATION: Synthetic sequence: Randomisation
      oligonucleotide for construction of targeted "loop 4" ribosome
      display library
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

```
<400> SEQUENCE: 33
ccactggagg tgcccgtgca snnsnnsnns nnsnnsnnsn ncaactcatt ccccatcatg      60
tagg                                                                  64

<210> SEQ ID NO 34
<211> LENGTH: 25
<212> TYPE: DNA
<213> ORGANISM: Artificial sequence
<220> FEATURE:
<223> OTHER INFORMATION: Synthetic sequence: Overlap oligonucleotide for
      construction of targeted "loop 4" ribosome display library

<400> SEQUENCE: 34
tgcacgggca cctccagtgg aaatc                                           25

<210> SEQ ID NO 35
<211> LENGTH: 124
<212> TYPE: PRT
<213> ORGANISM: Homo sapiens

<400> SEQUENCE: 35
```

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

```
<210> SEQ ID NO 36
<211> LENGTH: 124
<212> TYPE: PRT
<213> ORGANISM: Artificial sequence
<220> FEATURE:
<223> OTHER INFORMATION: Synthetic sequence: CTLA-4 Variant 1315

<400> SEQUENCE: 36
```

Met His Val Ala Gln Pro Ala Val Val Leu Ala Ser Ser Arg Gly Ser
1               5                   10                  15

Ala Ser Phe Val Cys Glu Tyr Ala Asn Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Gly Thr Phe Leu Asp Asp Ser
    50                  55                  60

Ile Cys Thr Gly Thr Ala Ser Gly Asn Gln Val Asn Leu Thr Ile Arg
65                  70                  75                  80

Gly Leu Arg Ala Ser Asp Thr Gly Leu Tyr Ile Cys Gln Val Glu Leu
                85                  90                  95

```
Met Tyr Pro Pro Pro Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 37
<211> LENGTH: 124
<212> TYPE: PRT
<213> ORGANISM: Artificial sequence
<220> FEATURE:
<223> OTHER INFORMATION: Synthetic sequence: CTLA-4 Variant 1322

<400> SEQUENCE: 37

```
Met His Val Ala Gln Pro Ala Val Val Leu Ala Ser Ser Arg Gly Ile
1               5                   10                  15

Ala Ser Phe Val Cys Glu Tyr Ala Asn Pro Ser Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Lys Gly Ser Glu Leu Ser Thr Gln Asp Tyr Pro
    50                  55                  60

Asn Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 38
<211> LENGTH: 124
<212> TYPE: PRT
<213> ORGANISM: Artificial sequence
<220> FEATURE:
<223> OTHER INFORMATION: Synthetic sequence: CTLA-4 Variant 1321

<400> SEQUENCE: 38

```
Met His Val Ala Gln Pro Ala Val Val Leu Ala Ser Ser Arg Gly Ser
1               5                   10                  15

Ala Ser Phe Val Cys Glu Tyr Ala Asn Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Lys Gly Asn Glu Gly Thr Phe Leu Asp Asp Ser
    50                  55                  60

Ile Cys Thr Gly Thr Ala Ser Gly Asn Gln Val Asn Leu Thr Ile Arg
65                  70                  75                  80

Gly Leu Arg Ala Ser Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 39
<211> LENGTH: 124
<212> TYPE: PRT
<213> ORGANISM: Artificial sequence

```
<220> FEATURE:
<223> OTHER INFORMATION: Synthetic sequence: CTLA-4 Variant 0943

<400> SEQUENCE: 39

Met His Val Ala Gln Pro Ala Val Val Leu Ala Ser Ser Arg Gly Ile
1               5                   10                  15

Ala Ser Phe Val Cys Glu Tyr Ala Pro Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Ser Thr Phe Leu Asp Asp Ser
    50                  55                  60

Ile Cys Thr Gly Thr Ser Ser Gly Asn Gln Val Asn Leu Thr Ile Arg
65                  70                  75                  80

Gly Leu Arg Ala Leu Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 40
<211> LENGTH: 124
<212> TYPE: PRT
<213> ORGANISM: Artificial sequence
<220> FEATURE:
<223> OTHER INFORMATION: Synthetic sequence: CTLA-4 Variant 0898

<400> SEQUENCE: 40

Met His Val Ala Gln Pro Ala Val Val Leu Ala Ser Ser Arg Gly Val
1               5                   10                  15

Ala Ser Phe Val Cys Glu Tyr Ala Pro Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Pro Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Leu Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 41
<211> LENGTH: 124
<212> TYPE: PRT
<213> ORGANISM: Artificial sequence
<220> FEATURE:
<223> OTHER INFORMATION: Synthetic sequence: CTLA-4 Variant 1319

<400> SEQUENCE: 41

Met His Val Ala Gln Pro Ala Val Val Leu Ala Ser Ser Arg Gly Ile
1               5                   10                  15

Ala Ser Phe Val Cys Glu Tyr Ala Pro Pro Gly Lys Ala Thr Glu Val
            20                  25                  30
```

```
Arg Val Thr Val Leu Arg Gln Ala Asp Ser Gln Val Thr Glu Val Cys
         35                  40                  45

Ala Ala Thr Tyr Met Met Gly Ser Glu Leu Ser Thr Gln Asp Tyr Pro
 50                  55                  60

Asn Cys Thr Gly Thr Ala Ser Gly Asn Gln Val Asn Leu Thr Ile Gln
 65                  70                  75                  80

Gly Leu Arg Ala Met Asp Thr Gly Leu Tyr Ile Cys Gln Val Glu Leu
             85                  90                  95

Met Tyr Pro Pro Pro Tyr Tyr Leu Gly Ile Gly Asn Gly Thr Gln Ile
             100                 105                 110

Tyr Val Ile Asp Pro Glu Pro Cys Pro Asp Ser Asp
         115                 120
```

<210> SEQ ID NO 42
<211> LENGTH: 124
<212> TYPE: PRT
<213> ORGANISM: Artificial sequence
<220> FEATURE:
<223> OTHER INFORMATION: Synthetic sequence: CTLA-4 Variant 1115

<400> SEQUENCE: 42

```
Met His Val Ala Gln Pro Ala Val Val Leu Ala Ser Ser Arg Gly Val
 1               5                  10                  15

Ala Ser Phe Val Cys Glu Tyr Ala Asn Pro Gly Lys Ala Thr Glu Val
             20                  25                  30

Arg Val Thr Val Leu Arg Gln Ala Asp Ser Gln Val Thr Glu Val Cys
         35                  40                  45

Ala Ala Thr Tyr Met Met Gly Asn Glu Gly Thr Phe Leu Asp Asp Ser
 50                  55                  60

Ile Cys Thr Gly Thr Ala Ser Gly Asn Gln Val Asn Leu Thr Ile Gln
 65                  70                  75                  80

Gly Leu Arg Ala Gln Asp Thr Gly Leu Tyr Ile Cys Gln Val Glu Leu
             85                  90                  95

Met Tyr Pro Pro Pro Tyr Tyr Leu Gly Ile Gly Asn Gly Thr Gln Ile
             100                 105                 110

Tyr Val Ile Asp Pro Glu Pro Cys Pro Asp Ser Asp
         115                 120
```

<210> SEQ ID NO 43
<211> LENGTH: 124
<212> TYPE: PRT
<213> ORGANISM: Artificial sequence
<220> FEATURE:
<223> OTHER INFORMATION: Synthetic sequence: CTLA-4 Variant 1299

<400> SEQUENCE: 43

```
Met His Val Ala Gln Pro Ala Val Val Leu Ala Ser Ser Arg Gly Arg
 1               5                  10                  15

Ala Ser Phe Val Cys Glu Tyr Thr Asn Pro Ser Lys Ala Thr Glu Val
             20                  25                  30

Arg Val Thr Val Leu Arg Gln Ala Asp Ser Gln Val Thr Glu Val Cys
         35                  40                  45

Ala Ala Thr Tyr Met Met Gly Asn Glu Ala Thr Phe Leu Asp Asp Ser
 50                  55                  60

Ile Cys Thr Gly Thr Ala Ser Gly Asn Gln Val Asn Leu Thr Ile Gln
 65                  70                  75                  80

Gly Leu Arg Ala Gln Asp Thr Gly Leu Tyr Ile Cys Gln Val Glu Leu
             85                  90                  95
```

-continued

Met Tyr Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 44
<211> LENGTH: 124
<212> TYPE: PRT
<213> ORGANISM: Artificial sequence
<220> FEATURE:
<223> OTHER INFORMATION: Synthetic sequence: CTLA-4 Variant 1249

<400> SEQUENCE: 44

Met His Val Ala Gln Pro Ala Val Val Leu Ala Ser Ser Arg Gly Arg
1               5                   10                  15

Ala Ser Phe Val Cys Glu Tyr Ala Asn Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Pro Thr Phe Leu Asp Asp Ser
    50                  55                  60

Ile Cys Thr Gly Thr Met Ser Gly Asn Gln Val Asn Leu Thr Ile Gln
65                  70                  75                  80

Gly Leu Arg Ala Val Asp Thr Gly Leu Tyr Ile Cys Thr Val Glu Leu
                85                  90                  95

Met Tyr Pro Pro Tyr Tyr Leu Gly Ile Gly Asp Gly Thr Gln Ile
            100                 105                 110

Tyr Val Ile Asp Pro Glu Pro Cys Pro Asp Ser Asp
        115                 120

<210> SEQ ID NO 45
<211> LENGTH: 124
<212> TYPE: PRT
<213> ORGANISM: Artificial sequence
<220> FEATURE:
<223> OTHER INFORMATION: Synthetic sequence: CTLA-4 Variant 1303

<400> SEQUENCE: 45

Met His Val Ala Gln Pro Ala Val Val Leu Ala Ser Ser Arg Gly Thr
1               5                   10                  15

Ala Ser Phe Val Cys Glu Tyr Ala Pro Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Ala Thr Phe Leu Asp Asp Ser
    50                  55                  60

Ile Cys Thr Gly Thr His Ser Gly Asn Gln Val Asn Leu Thr Ile Gln
65                  70                  75                  80

Gly Leu Arg Ala Arg Asp Thr Gly Leu Tyr Ile Cys Gln Val Glu Leu
                85                  90                  95

Met Tyr Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 46
<211> LENGTH: 124
<212> TYPE: PRT

```
<213> ORGANISM: Artificial sequence
<220> FEATURE:
<223> OTHER INFORMATION: Synthetic sequence: CTLA-4 Variant 1114

<400> SEQUENCE: 46

Met His Val Ala Gln Pro Ala Val Val Leu Ala Ser Ser Arg Gly Arg
1               5                   10                  15

Ala Ser Phe Val Cys Glu Tyr Ala Asn Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Gly Thr Phe Leu Asp Asp Ser
    50                  55                  60

Ile Cys Thr Gly Thr Thr Ser Gly Asn Gln Val Asn Leu Thr Ile Gln
65                  70                  75                  80

Gly Leu Arg Ala Lys Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 47
<211> LENGTH: 124
<212> TYPE: PRT
<213> ORGANISM: Artificial sequence
<220> FEATURE:
<223> OTHER INFORMATION: Synthetic sequence: CTLA-4 Variant 1227

<400> SEQUENCE: 47

Met His Val Ala Gln Pro Ala Val Val Leu Ala Ser Ser Arg Gly Ser
1               5                   10                  15

Ala Ser Phe Val Cys Glu Tyr Ala Asn Pro Ser Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Ala Thr Phe Leu Asp Asp Ser
    50                  55                  60

Ile Cys Thr Gly Thr Ala Ser Gly Asn Gln Val Asn Leu Thr Ile Gln
65                  70                  75                  80

Gly Leu Arg Ala Gln Asp Thr Gly Leu Tyr Ile Cys His Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 48
<211> LENGTH: 124
<212> TYPE: PRT
<213> ORGANISM: Artificial sequence
<220> FEATURE:
<223> OTHER INFORMATION: Synthetic sequence: CTLA-4 Variant 0722

<400> SEQUENCE: 48

Met His Val Ala Gln Pro Ala Val Val Leu Ala Ser Ser Arg Gly Val
1               5                   10                  15

Ala Ser Phe Val Cys Glu Tyr Ala Pro Pro Gly Lys Ala Thr Glu Val
            20                  25                  30
```

```
Arg Val Thr Val Leu Arg Gln Ala Asp Gly Gln Val Thr Glu Val Cys
            35                  40                  45

Ala Ala Thr Tyr Met Met Gly Asn Glu Ser Thr Phe Leu Asp Asp Ser
 50                      55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Glu Val Glu Leu
                85                  90                  95

Met Tyr Pro Pro Pro Tyr Tyr Arg Gly Ile Gly Asn Gly Thr Gln Ile
            100                 105                 110

Tyr Val Ile Asp Pro Glu Pro Cys Pro Asp Ser Asp
            115                 120

<210> SEQ ID NO 49
<211> LENGTH: 124
<212> TYPE: PRT
<213> ORGANISM: Artificial sequence
<220> FEATURE:
<223> OTHER INFORMATION: Synthetic sequence: CTLA-4 Variant 0645

<400> SEQUENCE: 49

Met His Val Ala Gln Pro Ala Val Val Leu Ala Ser Ser Arg Gly Thr
 1               5                  10                  15

Ala Ser Phe Val Cys Glu Tyr Ala Pro Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Ala Phe Pro Asp Asp Ser
 50                      55                  60

Val Cys Thr Gly Thr Thr Ser Gly Asn Gln Val Asn Leu Thr Ile Gln
 65                  70                  75                  80

Gly Leu Arg Ala Met Asp Thr Gly Leu Tyr Ile Cys Glu Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120

<210> SEQ ID NO 50
<211> LENGTH: 124
<212> TYPE: PRT
<213> ORGANISM: Artificial sequence
<220> FEATURE:
<223> OTHER INFORMATION: Synthetic sequence: CTLA-4 Variant 0636

<400> SEQUENCE: 50

Met His Val Ala Gln Pro Ala Val Val Leu Ala Ser Ser Arg Gly Ile
 1               5                  10                  15

Ala Ser Phe Val Cys Glu Tyr Ala Pro Pro Gly Lys Ala Thr Glu Val
                20                  25                  30

Arg Val Thr Val Leu Arg Gln Ala Gly Ser Gln Val Thr Glu Val Cys
            35                  40                  45

Ala Ala Thr Tyr Met Lys Gly Asn Glu Ser Thr Phe Leu Asp Asp Ser
 50                      55                  60

Val Cys Thr Gly Thr Thr Ser Gly Asn Gln Val Asn Leu Thr Ile Gln
 65                  70                  75                  80

Gly Leu Arg Ala Met Asp Thr Gly Leu Tyr Ile Cys Gln Val Glu Leu
```

```
                85                  90                  95
Met Tyr Pro Pro Pro Tyr Tyr Leu Gly Ile Gly Asn Gly Thr Gln Ile
                    100                 105                 110

Tyr Val Val Asp Pro Glu Pro Cys Pro Asp Ser Asp
            115                 120

<210> SEQ ID NO 51
<211> LENGTH: 124
<212> TYPE: PRT
<213> ORGANISM: Artificial sequence
<220> FEATURE:
<223> OTHER INFORMATION: Synthetic sequence: CTLA-4 Variant 0745

<400> SEQUENCE: 51

Met His Val Ala Gln Pro Ala Val Val Leu Ala Ser Ser Arg Gly Thr
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Gly Glu Ser Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Glu Val Glu Leu
                85                  90                  95

Met Tyr Pro Pro Pro Tyr Arg Gly Val Gly Asn Gly Thr Gln Ile
                    100                 105                 110

Tyr Val Ile Asp Pro Glu Pro Cys Pro Asp Ser Asp
            115                 120

<210> SEQ ID NO 52
<211> LENGTH: 123
<212> TYPE: PRT
<213> ORGANISM: Artificial sequence
<220> FEATURE:
<223> OTHER INFORMATION: Synthetic sequence: CTLA-4 Variant 0673

<400> SEQUENCE: 52

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Tyr Met Met Gly Asn Glu Leu Thr Phe Leu Gly Asp Ser Thr
    50                  55                  60

Cys Thr Gly Thr Ser Ser Gly Asn Gln Val Asn Leu Thr Ile Gln Gly
65                  70                  75                  80

Leu Arg Ala Met Asp Ser Gly Leu Tyr Ile Cys Lys Val Glu Leu Met
                85                  90                  95

Tyr Pro Pro Pro Tyr Tyr Leu Gly Ile Gly Asn Gly Thr Gln Ile Tyr
                    100                 105                 110

Val Ile Asp Pro Glu Pro Cys Pro Asp Ser Asp
        115                 120

<210> SEQ ID NO 53
<211> LENGTH: 124
```

```
<212> TYPE: PRT
<213> ORGANISM: Artificial sequence
<220> FEATURE:
<223> OTHER INFORMATION: Synthetic sequence: CTLA-4 Variant 0788

<400> SEQUENCE: 53

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Ile
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Ser Thr Phe Leu Asp Asp Ser
    50                  55                  60

Ile Cys Thr Gly Thr Ser Ser Gly Asn Gln Val Asn Leu Thr Ile Arg
65                  70                  75                  80

Gly Leu Arg Ala Val Asp Thr Gly Leu Tyr Ile Cys Met Val Glu Leu
                85                  90                  95

Met Tyr Pro Pro Pro Tyr Tyr Gln Gly Ile Gly Ser Gly Thr Gln Ile
            100                 105                 110

Tyr Val Ile Asp Pro Glu Pro Cys Pro Asp Ser Asp
        115                 120

<210> SEQ ID NO 54
<211> LENGTH: 123
<212> TYPE: PRT
<213> ORGANISM: Artificial sequence
<220> FEATURE:
<223> OTHER INFORMATION: Synthetic sequence: CTLA-4 Variant 0701

<400> SEQUENCE: 54

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Glu Thr Glu Val Cys
        35                  40                  45

Ala Ala Tyr Met Val Gly Asn Glu Leu Thr Phe Leu Gly Asp Ser Ile
    50                  55                  60

Cys Thr Gly Thr Ser Ser Gly Asn Gln Val Asn Leu Thr Ile Gln Gly
65                  70                  75                  80

Leu Arg Ala Met Asp Thr Gly Leu Tyr Ile Cys Lys Val Glu Leu Met
                85                  90                  95

Tyr Pro Pro Pro Tyr Tyr Glu Gly Ile Gly Asn Gly Thr Gln Ile Tyr
            100                 105                 110

Val Phe Asp Pro Glu Pro Cys Pro Asp Ser Asp
        115                 120

<210> SEQ ID NO 55
<211> LENGTH: 124
<212> TYPE: PRT
<213> ORGANISM: Artificial sequence
<220> FEATURE:
<223> OTHER INFORMATION: Synthetic sequence: CTLA-4 Variant 0439

<400> SEQUENCE: 55

Met His Val Ala Gln Pro Ala Val Val Leu Ala Ser Ser Arg Gly Ile
1               5                   10                  15

Ala Ser Phe Val Cys Glu Tyr Ala Pro Pro Gly Lys Ala Thr Glu Val
```

```
                   20                  25                  30
Arg Val Thr Val Leu Arg Gln Ala Asp Ser Gln Val Thr Glu Val Cys
             35                  40                  45

Ala Ala Thr Tyr Met Met Gly Ser Glu Leu Ser Thr Gln Asp Tyr Pro
 50                  55                  60

Asn Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
             85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120

<210> SEQ ID NO 56
<211> LENGTH: 233
<212> TYPE: PRT
<213> ORGANISM: Homo sapiens

<400> SEQUENCE: 56

Val Glu Pro Lys Ser Cys Asp Lys Thr His Thr Cys Pro Pro Cys Pro
 1               5                  10                  15

Ala Pro Glu Leu Leu Gly Gly Pro Ser Val Phe Leu Phe Pro Pro Lys
             20                  25                  30

Pro Lys Asp Thr Leu Met Ile Ser Arg Thr Pro Glu Val Thr Cys Val
             35                  40                  45

Val Val Asp Val Ser His Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
             85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 57
<211> LENGTH: 233
<212> TYPE: PRT
<213> ORGANISM: Artificial sequence
<220> FEATURE:
```

<223> OTHER INFORMATION: Synthetic sequence: Fc Variant-1

<400> SEQUENCE: 57

```
Gln Glu Pro Lys Ser Ser Asp Lys Thr His Thr Ser Pro Pro Ser Pro
1               5                   10                  15

Ala Pro Glu Leu Leu Gly Gly Ser Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 58
<211> LENGTH: 233
<212> TYPE: PRT
<213> ORGANISM: Artificial sequence
<220> FEATURE:
<223> OTHER INFORMATION: Synthetic sequence: Fc Variant-2

<400> SEQUENCE: 58

```
Gln Glu Pro Lys Ser Ser Asp Lys Thr His Thr Ser Pro Pro Ser Pro
1               5                   10                  15

Ala Pro Glu Leu Leu Gly Gly Ser Ser Val Phe Leu Phe Pro Pro Lys
            20                  25                  30

Pro Lys Asp Thr Leu Tyr Ile Thr Arg Glu Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110
```

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 59
<211> LENGTH: 233
<212> TYPE: PRT
<213> ORGANISM: Artificial sequence
<220> FEATURE:
<223> OTHER INFORMATION: Synthetic sequence: Fc Variant-3

<400> SEQUENCE: 59

Val Glu Pro Lys Ser Cys Asp Lys Thr His Thr Cys Pro Pro Cys Pro
1               5                   10                  15

Ala Pro Glu Phe Glu Gly Gly Pro Ser Val Phe Leu Phe Pro Pro Lys
            20                  25                  30

Pro Lys Asp Thr Leu Tyr Ile Thr Arg Glu Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Ser Ile Glu Lys Thr Ile Ser Lys Ala Lys Gly Gln
        115                 120                 125

Pro Arg Glu Pro Gln Val Tyr Thr Leu Pro Pro Ser Arg Glu Glu Met
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 60
<211> LENGTH: 230
<212> TYPE: PRT
<213> ORGANISM: Artificial sequence
<220> FEATURE:
<223> OTHER INFORMATION: Synthetic sequence: Fc Variant-4

<400> SEQUENCE: 60

```
Val Glu Ser Lys Tyr Gly Pro Pro Cys Pro Cys Pro Ala Pro Glu
1               5                   10                  15

Phe Leu Gly Gly Pro Ser Val Phe Leu Phe Pro Pro Lys Pro Lys Asp
                20                  25                  30

Thr Leu Tyr Ile Thr Arg Glu Pro Glu Val Thr Cys Val Val Val Asp
            35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
                100                 105                 110

Ser Ser Ile Glu Lys Thr Ile Ser Lys Ala Lys Gly Gln Pro Arg Glu
            115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Lys
225                 230
```

<210> SEQ ID NO 61
<211> LENGTH: 61
<212> TYPE: DNA
<213> ORGANISM: Artificial sequence
<220> FEATURE:
<223> OTHER INFORMATION: Synthetic sequence: Overlap oligonucleotide for
      construction of hotspot mutagenesis ribosome display library

<400> SEQUENCE: 61
gagatatatc catggccgca atgcacgtgg cccagcctgc tgtggtactg gccagcagcc     60
g                                                                    61

<210> SEQ ID NO 62
<211> LENGTH: 80
<212> TYPE: DNA
<213> ORGANISM: Artificial sequence
<220> FEATURE:
<223> OTHER INFORMATION: Synthetic sequence: Overlap oligonucleotide for
      construction of hotspot mutagenesis ribosome display library

```
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 62
cggacctcag tggctttgcc tggsnntgca tactcacaca caaagctggc snngcctcgg    60
ctgctggcca gtaccacagc                                                80

<210> SEQ ID NO 63
<211> LENGTH: 70
<212> TYPE: DNA
<213> ORGANISM: Artificial sequence
<220> FEATURE:
<223> OTHER INFORMATION: Synthetic sequence: Overlap oligonucleotide for
      construction of hotspot mutagenesis ribosome display library

<400> SEQUENCE: 63
ggcaaagcca ctgaggtccg ggtgacagtg cttcggcagg ctgacagcca ggtgactgaa    60
gtctgtgcgg                                                            70

<210> SEQ ID NO 64
<211> LENGTH: 70
<212> TYPE: DNA
<213> ORGANISM: Artificial sequence
<220> FEATURE:
<223> OTHER INFORMATION: Synthetic sequence: Overlap oligonucleotide for
      construction of hotspot mutagenesis ribosome display library
<220> FEATURE:
<221> NAME/KEY: misc_feature
<222> LOCATION: (26)..(27)
<223> OTHER INFORMATION: n is a, c, g, or t

<400> SEQUENCE: 64
gcagatggaa tcatctagga aggtsnnctc attccccatc atgtaggttg ccgcacagac    60
ttcagtcacc                                                            70

<210> SEQ ID NO 65
<211> LENGTH: 72
<212> TYPE: DNA
<213> ORGANISM: Artificial sequence
<220> FEATURE:
<223> OTHER INFORMATION: Synthetic sequence: Overlap oligonucleotide for
      construction of hotspot mutagenesis ribosome display library
<220> FEATURE:
<221> NAME/KEY: misc_feature
<222> LOCATION: (29)..(30)
<223> OTHER INFORMATION: n is a, c, g, or t

<400> SEQUENCE: 65
cctagatgat tccatctgca cgggcaccnn sagtggaaat caagtgaacc tcactatcca    60
aggactgagg gc                                                         72

<210> SEQ ID NO 66
<211> LENGTH: 59
<212> TYPE: DNA
<213> ORGANISM: Artificial sequence
<220> FEATURE:
<223> OTHER INFORMATION: Synthetic sequence: Overlap oligonucleotide for
      construction of hotspot mutagenesis ribosome display library
<220> FEATURE:
<221> NAME/KEY: misc_feature
<222> LOCATION: (18)..(19)
```

```
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t

<400> SEQUENCE: 66
ggtacatgag ctccacsnng cagatgtaga gtcccgtgtc snntgccctc agtccttgg      59

<210> SEQ ID NO 67
<211> LENGTH: 31
<212> TYPE: DNA
<213> ORGANISM: Artificial sequence
<220> FEATURE:
<223> OTHER INFORMATION: Synthetic sequence: Overlap oligonucleotide for
      construction of hotspot mutagenesis ribosome display library

<400> SEQUENCE: 67
gtggagctca tgtacccacc gccatactac c                                   31

<210> SEQ ID NO 68
<211> LENGTH: 124
<212> TYPE: PRT
<213> ORGANISM: Artificial sequence
<220> FEATURE:
<223> OTHER INFORMATION: Synthetic sequence: CTLA-4 polypeptide
<220> FEATURE:
<221> NAME/KEY: VARIANT
<222> LOCATION: (16)..(16)
<223> OTHER INFORMATION: Xaa is Arg, Ile, Ser or Val
<220> FEATURE:
<221> NAME/KEY: VARIANT
<222> LOCATION: (24)..(24)
<223> OTHER INFORMATION: Xaa is Thr or Ala
<220> FEATURE:
<221> NAME/KEY: VARIANT
<222> LOCATION: (27)..(27)
<223> OTHER INFORMATION: Xaa is Ser or Gly
<220> FEATURE:
<221> NAME/KEY: VARIANT
<222> LOCATION: (54)..(54)
<223> OTHER INFORMATION: Xaa is Met or Lys
<220> FEATURE:
<221> NAME/KEY: VARIANT
<222> LOCATION: (56)..(56)
<223> OTHER INFORMATION: Xaa is Asn or Ser
<220> FEATURE:
<221> NAME/KEY: VARIANT
<222> LOCATION: (58)..(58)
<223> OTHER INFORMATION: Xaa is Ala, Leu or Gly
<220> FEATURE:
<221> NAME/KEY: VARIANT
<222> LOCATION: (59)..(59)
<223> OTHER INFORMATION: Xaa is Thr or Ser
<220> FEATURE:
<221> NAME/KEY: VARIANT
<222> LOCATION: (60)..(60)
<223> OTHER INFORMATION: Xaa is Phe or Thr
<220> FEATURE:
<221> NAME/KEY: VARIANT
<222> LOCATION: (61)..(61)
<223> OTHER INFORMATION: Xaa is Leu or Gln
<220> FEATURE:
<221> NAME/KEY: VARIANT
<222> LOCATION: (63)..(63)
<223> OTHER INFORMATION: Xaa is Asp or Tyr
<220> FEATURE:
<221> NAME/KEY: VARIANT
<222> LOCATION: (64)..(64)
<223> OTHER INFORMATION: Xaa is Ser or Pro
<220> FEATURE:
<221> NAME/KEY: VARIANT
<222> LOCATION: (65)..(65)
<223> OTHER INFORMATION: Xaa is Ile, Asn or Asp
<220> FEATURE:
```

<221> NAME/KEY: VARIANT
<222> LOCATION: (70)..(70)
<223> OTHER INFORMATION: Xaa is Ala or Ser
<220> FEATURE:
<221> NAME/KEY: VARIANT
<222> LOCATION: (80)..(80)
<223> OTHER INFORMATION: Xaa is Gln or Arg
<220> FEATURE:
<221> NAME/KEY: VARIANT
<222> LOCATION: (85)..(85)
<223> OTHER INFORMATION: Xaa is Gln, Met or Ser
<220> FEATURE:
<221> NAME/KEY: VARIANT
<222> LOCATION: (93)..(93)
<223> OTHER INFORMATION: Xaa is Gln or His

<400> SEQUENCE: 68

```
Met His Val Ala Gln Pro Ala Val Val Leu Ala Ser Ser Arg Gly Xaa
1               5                   10                  15

Ala Ser Phe Val Cys Glu Tyr Xaa Asn Pro Xaa Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Xaa Gly Xaa Glu Xaa Xaa Xaa Xaa Asp Xaa Xaa
    50                  55                  60

Xaa Cys Thr Gly Thr Xaa Ser Gly Asn Gln Val Asn Leu Thr Ile Xaa
65                  70                  75                  80

Gly Leu Arg Ala Xaa Asp Thr Gly Leu Tyr Ile Cys Xaa Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 69
<211> LENGTH: 7
<212> TYPE: PRT
<213> ORGANISM: Artificial sequence
<220> FEATURE:
<223> OTHER INFORMATION: Synthetic sequence: CTLA-4 loop 4 motif

<400> SEQUENCE: 69

```
Ser Thr Gln Asp Tyr Pro Asn
1               5
```

<210> SEQ ID NO 70
<211> LENGTH: 19
<212> TYPE: PRT
<213> ORGANISM: Homo sapiens

<400> SEQUENCE: 70

```
Val Glu Pro Lys Ser Cys Asp Lys Thr His Thr Cys Pro Pro Cys Pro
1               5                   10                  15

Ala Pro Glu
```

<210> SEQ ID NO 71
<211> LENGTH: 19
<212> TYPE: PRT
<213> ORGANISM: Artificial sequence
<220> FEATURE:
<223> OTHER INFORMATION: Synthetic sequence: modified human IgG1 Fc
      region comprising hinge

<400> SEQUENCE: 71

-continued

```
Gln Glu Pro Lys Ser Ser Asp Lys Thr His Thr Ser Pro Pro Ser Pro
1               5                   10                  15

Ala Pro Glu

<210> SEQ ID NO 72
<211> LENGTH: 20
<212> TYPE: PRT
<213> ORGANISM: Artificial sequence
<220> FEATURE:
<223> OTHER INFORMATION: Synthetic sequence: FLAG 10xhis tag

<400> SEQUENCE: 72

Asp Tyr Lys Asp Asp Asp Asp Lys Ala Ala His His His His His
1               5                   10                  15

His His His His
            20
```

CTLA-4 VARIANTS

CROSS-REFERENCE TO RELATED APPLICATIONS

This application is a U.S. National Stage application of International Application No. PCT/US2013/030179, filed on Mar. 11, 2013, said International Application No. PCT/US2013/030179 claims benefit under 35 U.S.C. §119(e) of the U.S. Provisional Application No. 61/645,686, filed May 11, 2012. Each of the above listed applications is incorporated by reference herein in its entirety for all purposes.

REFERENCE TO SEQUENCE LISTING SUBMITTED ELECTRONICALLY

The content of the electronically submitted sequence listing in ASCII text file (Name Sequencelisting.TXT; Size: 107,814 bytes; and Date of Creation: Mar. 11, 2013) filed with the application is incorporated herein by reference in its entirety.

FIELD OF THE INVENTION

This invention relates to compositions comprising variants of cytotoxic T-lymphocyte antigen 4 (CTLA-4), optionally fused to IgG Fc, and their therapeutic use to inhibit T cell activation, especially in the context of inflammatory conditions such as rheumatoid arthritis (RA).

BACKGROUND

Activation of naïve T cells is thought to proceed by a two-signal mechanism. Upon encountering an antigen presenting cell (APC), the T cell receptor (TCR) interacts with peptide in the context of major histocompatibility complex (MHC) molecules and thus delivers the first activation signal to the T cells. This initial signal is insufficient to lead to T cell activation and a second signal from co-stimulatory receptors is an absolute requirement. One of the most important and best described co-stimulatory receptor is CD28 which interacts with CD80 (B7.1) and CD86 (B7.2) on the surface of macrophages, dendritic cells as well as B and activated T lymphocytes.

The CD86 gene encodes a type I membrane protein (Swiss-Prot Acc-No P33681). Alternative splicing results in two transcript variants of the CD86 gene encoding different isoforms. Additional transcript variants have been described, but their full-length sequences have not been determined.

The related protein CD80 (Swiss-Prot Acc-No P42081) has a secondary structure similar to CD86. CD80 shares 26% and 46% of identical and similar amino acid residues with CD86, respectively. CD80 is expressed only at low levels in resting APCs but can be up-regulated following activation. CD80 recognizes the same receptors on T cells, CD28 and CD152 (CTLA-4), but binds the latter with approximately 2 to 4 fold higher affinity than CD86 does.

No shared linear peptide epitope had been identified that is responsible for binding to CD28 and/or CTLA-4 (Ellis et al., J Immunol., 156, 2700-2709) but conserved residues in the secondary structures (IgV sheets of CD80 and CD86) had been found in interaction with CTLA-4 (Swartz et al., Nature, 410, 604-608).

Signal transduction from CD28 leads to T cell activation and the upregulation of the CTLA-4 co-inhibitory receptor. CTLA-4 is a member of the immunoglobulin superfamily. It binds to CD80 and CD86 with increased affinity and avidity compared with CD28 and effectively downregulates activation signals.

Various theories have been postulated on the relative roles of CD80 and CD86 in binding CTLA-4. Slavik et al. (*Immunol. Res.* 19(1):1-24 1999) reviewed the signalling and function of the CD28/CTLA-4 and CD80/CD86 families. Sansom (*Immunology* 101:169-177 2000) summarised some studies where differences between CD80 and CD86 were investigated.

Odobasic et al. (*Immunology* 124:503-513 2008) investigated the roles of CD80 and CD86 in effector T cell responses. This study investigated the effects of anti-CD80 and anti-CD86 monoclonal antibodies in an antigen-induced mouse model of arthritis. It was reported that blockade of both CD80 and CD86 caused a trend towards reduced disease severity compared to control antibody-treated mice. Based on the results of treatment with the individual antibodies, the authors concluded that CD80 exacerbates arthritis by downregulating systemic IL-4 and increasing T cell accumulation in joints, while CD86 enhances disease severity by upregulating IL-17 and increasing the accumulation of effector T cells in joints without affecting Th1 or Th2 development. However, the study reports that no further additive reduction in arthritis severity was observed when both CD80 and CD86 were blocked, suggesting that inhibition of either costimulatory molecule was adequate to obtain maximal disease amelioration. This model was based on a recall response to antigen (BSA in this study) directly injected in the joint space.

Another study used a murine collagen-induced arthritis model, involving breaking tolerance to an endogenous antigen (collagen). In this study, blockade of both CD80 and CD86 was reported to be required for maximal benefit (Webb et al. *Eur J. Immunol* 26(10):2320-2328 1996).

A recombinant fusion protein comprising the extracellular domain of CTLA-4 linked to a modified IgG1 Fc domain ("CTLA-4-Ig") has been shown to bind CD80 and CD86 in vivo and effectively suppress CD28-mediated T cell activation (Kliwinski et al., J Autoimmun. 2005; 25(3):165-71).

CTLA-4 fusion proteins have been developed as therapeutic agents for rheumatoid arthritis (RA). RA is a progressive degenerative disease leading to cartilage and bone destruction. There is evidence that many arms of the immune system are involved in the inflammatory process leading to fibroblast-like synoviocytes and osteoclast-mediated joint damage and cartilage and bone destruction. Multiple studies have shown increased T cell activation in the synovium and up to 50% of the cells infiltrating the inflamed pannus are T lympho. Furthermore, T cells in the synovium of RA patients exhibit an activated effector phenotype displaying increased expression of activation associated markers such as CD44, CD69, CD45RO, VLA-1 and CD27.

Activated T cells have been shown to play a key role in establishing and maintaining the pathological inflammatory response found in the RA synovium. Activated T cells are an important source of proinflammatory cytokines, such IFNγ, IL-17 and TNFα. These factors are potent activators of fibroblast-like synoviocytes (FLS) and macrophage-like synoviocytes (MLS) leading to the secretion of matrix metalloproteinases (MMP) which are mediators of cartilage destruction as well as the secretion of inflammatory mediators such as IL-6, IL-1 and TNFα. Activated CD4+ cells may also provide cognate help to B lymphocytes leading to the production of antibodies, such as rheumatoid factor (RF), that further contribute to disease progression.

Abatacept (ORENCIA®) is a CTLA-4 Ig fusion protein containing the extracellular domain of CTLA-4 fused to the Fc of IgG1. The resulting soluble protein is a dimer with a molecular weight of approximately 92 kDa. It has been shown to have beneficial effects in treating RA patients in the clinic, demonstrating that inhibition of the co-stimulation pathway involving CD80 and CD86 is a viable therapeutic approach for RA. RA therapy with Abatacept is administered either as an intravenous monthly or a weekly subcutaneous injection.

Abatacept contains in its CDR3-like loop the amino acid hexapeptide motif MYPPPY, which is shared between CD28 and CTLA-4 and is reported to be necessary for binding to the B7 ligands. Mutation of the first tyrosine (Y) in this motif to alanine (A) abolishes binding to CD80, but also results in reduced binding to CD86, whereas a phenylalanine (F) substitution allows for retention of the full affinity for CD80 with a total loss of CD86 binding (Harris et al., J. Exp. Med. (1997) 185:177-182). Other residues in the CDR3-like and CDR1-like regions are also important for the interaction of Abatacept with its ligands. Thus, a mutant molecule with glutamic acid (E) instead of leucine (L) at position 104 and tyrosine (Y) instead of alanine (A) at position 29 exhibits approximately 2-fold greater binding avidity for CD80 (B7-1) and approximately 4-fold greater binding avidity for CD86 (B7-2) than abatacept. This compound LEA-29Y (Belatacept, NULOJIX®; a selective T-cell (lymphocyte) costimulation blocker, that binds to CD80 and CD86 on antigen-presenting cells thereby blocking CD28 mediated costimulation of T lymphocytes) is reported to have similar affinity for binding CD80 as for binding CD86 (3.66 nM and 3.21 nM respectively). Belatacept has been developed as an immunosuppressant for transplantation (Larsen et al., Am. J. Transplantation (2005) 5:443-453; Gupta & Womer Drug Des Develop Ther 4:375-382 2010) and was recently approved for prophylaxis of organ rejection in adult patients receiving a kidney transplant. Abatacept itself showed limited efficacy against transplant rejection, a finding that has been attributed to its lower inhibition of CD86-dependent as opposed to CD80-dependent costimulation (Gupta & Womer, supra).

Formulations of Abatacept and Belatacept for subcutaneous administration are described in WO2007/07654.

Selections for improved affinity and stability have previously been performed using ribosome display to isolate improved variants of CTLA-4. Both error-prone PCR mutagenesis, to mutate the entire gene sequence, and directed mutagenesis, to target mutations to key regions, have been successful for protein evolution. For example, WO2008/047150 reported protein variants of CTLA-4 showing increased activity and increased stability compared with wild type.

Maxygen, Inc. reported a CTLA-4-Ig therapeutic molecule, designated ASP2408, being developed by Perseid Therapeutics LLC in collaboration with Astellas Pharma Inc for the treatment of RA. The CTLA-4-Ig was reported to show improved potency compared with ORENCIA® (Abatacept) a CTLA-4 Ig fusion protein containing the extracellular domain of CTLA-4 fused to the Fc of IgG1 (WO2009/058564).

U.S. Pat. No. 6,750,334 (Repligen Corporation) described CTLA-4-Cγ4, a soluble fusion protein comprising CTLA-4 fused to a portion of an immunoglobulin. The immunoglobulin constant region, comprising a hinge region and CH2 and CH3 domains, is modified by substitution, addition or deletion of at least one amino acid residue, to reduce complement activation or Fc receptor interaction.

Xencor, Inc. recently described a CTLA4-Ig molecule comprising a variant CTLA-4 portion and an immunoglobulin Fc region (WO2011/103584). A number of amino acid substitutions in the amino acid sequence of the CTLA-4 portion were described, for generating CTLA4-Ig variants with greater T-cell inhibitory activity. WO2011/103584 also describes Fc modifications, for example for improving binding to FcγRs, enhancing Fc-mediated effector functions and/or extending in vivo half life of the CTLA4-Ig.

SUMMARY OF THE INVENTION

In a first aspect, the invention provides CTLA-4 polypeptides that are variants of wild type CTLA-4. CTLA-4 polypeptides of the invention may have one or more improved properties, such as higher potency, higher affinity for CD80 and/or CD86, enhanced selectivity for CD80 over CD86, good cross-reactivity, and/or higher stability than wild type.

Improvements in CTLA-4 may be achieved by mutation of the amino acid sequence of human wild type human CTLA-4 extracellular domain, also known as soluble CTLA-4. One or more amino acid mutation, which may be an amino acid substitution, insertion or deletion, can be introduced into a CTLA-4 amino acid sequence to produce an improved CTLA-4 polypeptide as described herein. The polypeptide may for example exhibit increased potency, affinity and/or stability relative to wild type CTLA-4.

The CTLA-4 extracellular domain comprises wild type amino acid sequence SEQ ID NO: 35. SEQ ID NO: 35 is not the entire extracellular domain, but is the region employed in Abatacept (ORENCIA® a CTLA-4 Ig fusion protein containing the extracellular domain of CTLA-4 fused to the Fc of IgG1).

CTLA-4 polypeptides of the present invention may or may not comprise further CTLA-4 residues or sequences beyond the region corresponding to SEQ ID NO: 35. Preferably a CTLA-4 polypeptide of the invention is soluble. Generally therefore it would not comprise the CTLA-4 transmembrane region.

Identified herein are a number of mutations within the CTLA-4 amino acid sequence, which are associated with improved potency, affinity and/or stability or which may be introduced for other purposes such as to influence dimerisation.

Examples of amino acid substitutions in wild type CTLA-4 are: R, S, V or T at I16; T at A24; N or P at S25; S at G27; I at V 32; G at D41; G at S42; E at V44; K or V at M54; S or G at N56; A, G, S or P at L58; S or A at T59; T at F 60; Q or P at L61; G at D 62; Y at D63; P at S 64; N, D, V or T at I65; A, T, M or H at S70; R at Q80; Q, S, V, R, K or L at M85; S at T87; Q, H, T, E or M at K93; R, Q or E at L104; V at I106; D or S at N108; V or F at I115 and S at C120. An example of an amino acid deletion is deletion of T51. The residue numbering is with reference to the CTLA-4 sequences shown in FIG. 1A and FIG. 2, numbered with the first residue as position 1 "sequence numbering". FIG. 1 also shows Swiss Prot numbering for comparison.

A CTLA-4 variant may have, for example, up to twelve or up to twenty amino acid mutations in human wild type soluble CTLA-4. The mutations may include any or all of the amino acid mutations listed above, and optionally one or more different mutations, e.g. different substitutions, at these or at other residue positions. A variant amino acid sequence may comprise human wild type CTLA-4 sequence SEQ ID NO: 35 with one or more, e.g. at least five, six or seven of the listed amino acid mutations.

A CTLA-4 polypeptide may comprise or consist of an amino acid sequence having at least 70%, at least 75%, at least 80%, at least 85%, at least 90% or at least 95%, 96%, 97%, 98% or 99% sequence identity with SEQ ID NO: 35.

Examples of CTLA-4 variant amino acid sequences according to the invention include those of SEQ ID NOS: 36-55 shown in FIG. 1A. A CTLA-4 variant may comprise the "1299" CTLA-4 amino acid sequence encoded by nucleic acid deposited under NCIMB accession no. 41948. NCIMB accession no. 41948 encodes the 1299 CTLA-4 polypeptide fused to an immunoglobulin Fc region. The encoded 1299 CTLA-4 polypeptide, the encoded Fc region, and the encoded polypeptide comprising the 1299 CTLA-4 polypeptide fused to the Fc region, all of which are encoded by nucleic acid deposited under NCIMB accession no. 41948, are all individual embodiments of the present invention.

Preferred mutations are amino acid substitutions selected from the following: R, S or V at I16; T at A24; N at S25; Sat G27; K at M54; S at N56; A or G at L58; Sat T59; T at F 60; Q at L61; Y at D63; P at S 64; N or D at I65; A at S70; R at Q80; Q or S at M85; Q or H at K93; and S at C120. Accordingly, a variant amino acid sequence may comprise human wild type CTLA-4 sequence SEQ ID NO: 35 with one or more, e.g. at least five or six, or all, of these amino acid residue positions substituted with a different residue as specified.

A CTLA-4 polypeptide sequence preferably comprises: R, I, S or V at position 16; T or A at position 24; N at position 25; S or G at position 27; M or K at position 54; N or S at position 56; A, L or G at position 58; T or S at position 59; F or T at position 60; L or Q at position 61; D or Y at position 63; S or P at position 64; I, N or D at position 65; A or S at position 70; Q or R at position 80; Q, M or S at position 85; Q or H at position 93; and/or C or S at position 120. Other residue positions may be human wild type, or may be subject to one or more further mutations.

A CTLA-4 polypeptide may comprise N at position 25, representing a substitution of wild type S at this position. The polypeptide may comprise Q or H at position 93, representing a substitution of wild type K at this position. As illustrated by the Examples described later, these substitutions at residues 25 and 93 are believed to be strongly linked to improvements in affinity, potency and/or stability of the CTLA-4.

A preferred amino acid motif, which was observed in multiple high potency variants, is STQDYPN (SEQ ID NO: 69). This motif, located at residues 59-65, is in a loop region which appears to be in close proximity to CD80 and CD86 in the bound structure. Accordingly, in certain embodiments, a CTLA-4 polypeptide comprises SEQ ID NO: 69 at residues 59-65. Residue numbering is as shown in FIG. 1A (top row of numbering, starting from 1) and FIG. 2. Where insertions or deletions are present, actual residue numbering of the polypeptide may differ from the reference sequence. FIG. 1A also shows Swiss Prot numbering for comparison.

It may also be desirable to mutate C at position 120, e.g. by substitution with S, in order to remove a disulphide bridge forming between CTLA-4 molecules at this location, and to inhibit CTLA-4 dimerisation. In other situations, it is desirable to retain or promote CTLA-4 dimerisation or higher multimerisation (e.g. tetramer formation). This may be achieved for example through retention of C120 and/or through addition of dimerising domains, such as by conjugating CTLA-4 to an IgG Fc region. The addition of such domains and the formation of macromolecules comprising CTLA-4 will be further discussed later on.

A CTLA-4 polypeptide may comprise amino acid sequence SEQ ID NO: 68, or may comprise SEQ ID NO: 68 with one or more mutations. For example a CTLA-4 polypeptide may comprise SEQ ID NO: 68 with up to twelve mutations, up to ten amino acid mutations, or up to five mutations, e.g. one, two or three amino acid mutations. SEQ ID NO: 68 is illustrated in FIG. 2, and is a consensus sequence of residues found in a group of six CTLA-4 polypeptides with exceptionally good functional activity, which were produced as described in the Examples. The six polypeptides have amino acid sequences shown in FIG. 1A, with SEQ ID NOS as follows: SEQ ID NO: 43 (variant 1299), SEQ ID NO: 37 (variant 1322), SEQ ID NO: 38 (variant 1321), SEQ ID NO: 36 (variant 1315), SEQ ID NO: 42 (variant 1115) and SEQ ID NO: 47 (variant 1227). These six sequences, and variants with one or more amino acid mutations, for example up to twelve, e.g. up to ten amino acid mutations, e.g. up to five mutations, e.g. one, two or three amino acid mutations in any of these six sequences, represent examples of the invention. A CTLA-4 polypeptide may comprise the "1299" CTLA-4 polypeptide sequence deposited under NCIMB accession no. 41948 with one or more amino acid mutations, for example up to twelve, e.g. up to ten amino acid mutations, e.g. up to five mutations, e.g. one, two or three amino acid mutations.

CTLA-4 polypeptides according to the invention may comprise or consist of an amino acid sequence having at least 70%, at least 75%, at least 80%, at least 85%, at least 90% or at least 95%, 96%, 97%, 98% or 99% sequence identity with SEQ ID NO: 68, with any of SEQ ID NOS: 36-55, or with the "1299" CTLA-4 polypeptide sequence deposited under NCIMB accession no. 41948.

The mutation or mutations may comprise or consist of amino acid substitutions, and may optionally be selected from the following:

T at residue 16; P at residue 25; I at residue 32; G at residue 41; G at residue 42; E at residue 44; V at residue 54; G at residue 56; S or P at residue 58; A at residue 59; P at residue 61; G at residue 62; V or T at residue 65; T, M or H at residue 70; V, R, K or L at residue 85; S at residue 87; T, E or M at residue 93; R, Q or E at residue 104; V at residue 106; D or S at residue 108; V or F at residue 115; Sat residue 120; deletion at residue 51.

Preferably, a polypeptide comprises N at position 25, and/or comprises Q or H at position 93. A polypeptide may optionally comprise S at position 120.

As noted above, a polypeptide preferably comprises R, I, S or V at position 16; T or A at position 24; N at position 25; S or G at position 27; M or K at position 54; N or S at position 56; A, L or G at position 58; T or S at position 59; F or T at position 60; L or Q at position 61; D or Y at position 63; S or P at position 64; I, N or D at position 65; A or S at position 70; Q or R at position 80; Q, M or S at position 85; Q or H at position 93; and/or C or S at position 120. Thus, the polypeptide comprises one or more, e.g. at least five or six, or all, of the following amino acid substitutions relative to wild type CTLA-4 SEQ ID NO: 35: R, S or V at I16; T at A24; N at S25; S at G27; K at M54; S at N56; A or G at L58; S at T59; T at F 60; Q at L61; Y at D63; P at S 64; N or D at I65; A at S70; Rat Q80; Q or Sat M85; Q or H at K93.

Mutations in SEQ ID NOS: 36-55 compared with wild type are illustrated in FIG. 1A. A polypeptide according to the invention may comprise wild type CTLA-4 SEQ ID NO: 35 with one or more mutations exemplified in these variants, for example with the combination of mutations present in any of SEQ ID NOS: 36-55. A polypeptide may optionally comprise further mutations as discussed above, e.g. optionally one or two further mutations.

For example, a polypeptide may comprise a combination of mutations selected from:
the 1315 mutations i.e. S at I16; N at S25; G at L58; A at S70; R at Q80; S at M85; and Q at K93;
the 1322 mutations i.e. N at S25; S at G27; K at M54; S at N56; S at T59; T at F 60; Q at L61; Y at D63; P at S64; N at I65; and Q at K93;
the 1321 mutations i.e. S at I16; N at S25; K at M54; G at L58; A at S70; R at Q80; S at M85; and Q at K93;
the 1115 mutations i.e. V at I16; N at S25; G at L58; A at S70; Q at M85; and Q at K93;
the 1299 mutations i.e. R at I16; T at A24; N at S25; S at G27; A at L58; A at S70; Q at M85; and Q at K93; and
the 1227 mutations i.e. S at I16; N at S25; S at G27; A at L58; A at S70; Q at M85; and H at K93.

Accordingly, a CTLA-4 polypeptide may be one that comprises the combination of substituted residues in any of SEQ ID NOS: 36-55 relative to wild type, for example it may comprise:
S at residue 16; N at residue 25; G at residue 58; A at residue 70; R at residue 80; S at residue 85; and Q at residue 93;
N at residue 25; S at residue 27; K at residue 54; S at residue 56; S at residue 59; T at residue 60; Q at residue 61; Y at residue 63; P at residue 64; N at residue 65; and Q at residue 93;
S at residue 16; N at residue 25; K at residue 54; G at residue 58; A at residue 70; R at residue 80; S at residue 85; and Q at residue 93;
V at residue 16; N at residue 25; G at residue 58; A at residue 70; Q at residue 85; and Q at residue 93;
R at residue 16; T at residue 24; N at residue 25; S at residue 27; A at residue 58; A at residue 70; Q at residue 85; and Q at residue 93; or
S at residue 16; N at residue 25; S at residue 27; A at residue 58; A at residue 70; Q at residue 85; and H at residue 93.

A mutation is preferably a substitution, and may be a conservative substitution. By "conservative substitution" is meant substitution of a first amino acid residue with a second, different amino acid residue, wherein the first and second amino acid residues have side chains which have similar biophysical characteristics. Similar biophysical characteristics include hydrophobicity, charge, polarity or capability of providing or accepting hydrogen bonds. Examples of conservative substitutions include changing serine to threonine or tryptophan, glutamine to asparagine, lysine to arginine, alanine to valine, aspartate to glutamate, valine to isoleucine, asparagine to serine.

Polypeptides according to the invention may include one or more amino acid sequence mutations (substitution, deletion, and/or insertion of an amino acid residue), and less than about 15 14, 13, 12, 11, 10, 9, 8, 7, 6, 5, 4, 3 or 2.

The mutations normally do not result in loss of function, so a polypeptide comprising a thus-altered amino acid sequence may retain an ability to bind human CD80 and/or CD86. It may retain the same binding affinity or function as a polypeptide in which the alteration is not made, e.g. as measured in an assay described herein.

Mutation may comprise replacing one or more amino acid residues with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. [Voet & Voet, *Biochemistry,* 2nd Edition, (Wiley) 1995]. Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in polypeptides of the invention may comprise non-natural or non-standard amino acids described above. Non-standard amino acids (e.g. D-amino acids) may be incorporated into an amino acid sequence during synthesis, or by modification or replacement of the "original" standard amino acids after synthesis of the amino acid sequence.

Use of non-standard and/or non-naturally occurring amino acids increases structural and functional diversity, and can thus increase the potential for achieving desired binding and neutralising properties. Additionally, D-amino acids and analogues have been shown to have different pharmacokinetic profiles compared with standard L-amino acids, owing to in vivo degradation of polypeptides having L-amino acids after administration to an animal e.g. a human, meaning that D-amino acids are advantageous for some in vivo applications.

Variants may be generated using random mutagenesis of one or more selected VH and/or VL genes to generate mutations within the entire variable domain. Such a technique is described by Gram et al. [Gram et al., 1992, *Proc. Natl. Acad. Sci., USA,* 89:3576-3580], who used error-prone PCR. Another method that may be used is to direct mutagenesis to particular regions or locations in the polypeptide. Such techniques are disclosed by Barbas et al. [Barbas et al., 1994, *Proc. Natl. Acad. Sci., USA,* 91:3809-3813] and Schier et al. [Schier et al., 1996, *J. Mol. Biol.* 263:551-567].

All the above-described techniques are known as such in the art and the skilled person will be able to use such techniques to provide polypeptides of the invention using routine methodology in the art.

Algorithms that can be used to calculate % identity of two amino acid sequences include e.g. BLAST [Altschul et al. (1990) J. Mol. Biol. 215: 405-410], FASTA [Pearson and Lipman (1988) PNAS USA 85: 2444-2448], or the Smith-Waterman algorithm [Smith and Waterman (1981) J. Mol Biol. 147: 195-197] e.g. employing default parameters.

In accordance with the invention, compositions may be provided containing CTLA-4 polypeptides having improved biological activity such as enhanced selectivity for CD80 over CD86, higher affinity and/or higher potency, and/or may display good cross-reactivity, improved stability and/or extended half life compared with wild-type CTLA-4. As discussed in detail herein, such properties may contribute to greater therapeutic efficacy and may allow therapeutic benefits to be achieved at reduced or less frequent dosage. Improved stability may facilitate manufacture and formulation into pharmaceutical compositions.

A CTLA-4 polypeptide according to the invention is optionally conjugated to an IgG Fc region, e.g. as a fusion protein. The Fc region can be engineered to increase the in vivo half life of the molecule and to contribute to overall stability of the composition while avoiding unwanted Fc effector functions. Improved stability facilitates formulation of the product at high concentrations, e.g. for subcutaneous administration.

BRIEF DESCRIPTION OF THE DRAWINGS

FIG. 1. (A) Alignment of CTLA-4 variant sequences (SEQ ID NOS: 36-55) with wild type human CTLA-4 (SEQ ID NO: 35). Mutations from wild type are shown in grey boxes. The top row of numbering, starting from 1, is the numbering referred to in this specification unless otherwise specified. Swiss Prot numbering is shown underneath for comparison. (B) Alignment of IgG1 Fc sequences SEQ ID NO: 56, SEQ ID NO: 57, SEQ ID NO: 58, SEQ ID NO: 59 and SEQ ID NO: 60. The top row of numbering, starting from 1, is the numbering referred to in this specification unless otherwise specified. Swiss Prot numbering is shown underneath for comparison.

FIG. 2. CTLA-4 polypeptide sequence SEQ ID NO: 68. With sequential numbering starting from Met as position 1, SEQ ID NO: 68 has 124 residues, with variability at residues 16, 24 27, 54, 56, 58, 59, 60, 61, 63, 64, 65, 70, 80, 85 and 93. The amino acid residue at each of these variable positions is selected from the group of residues indicated in each instance.

DETAILED DESCRIPTION

Figure 1:
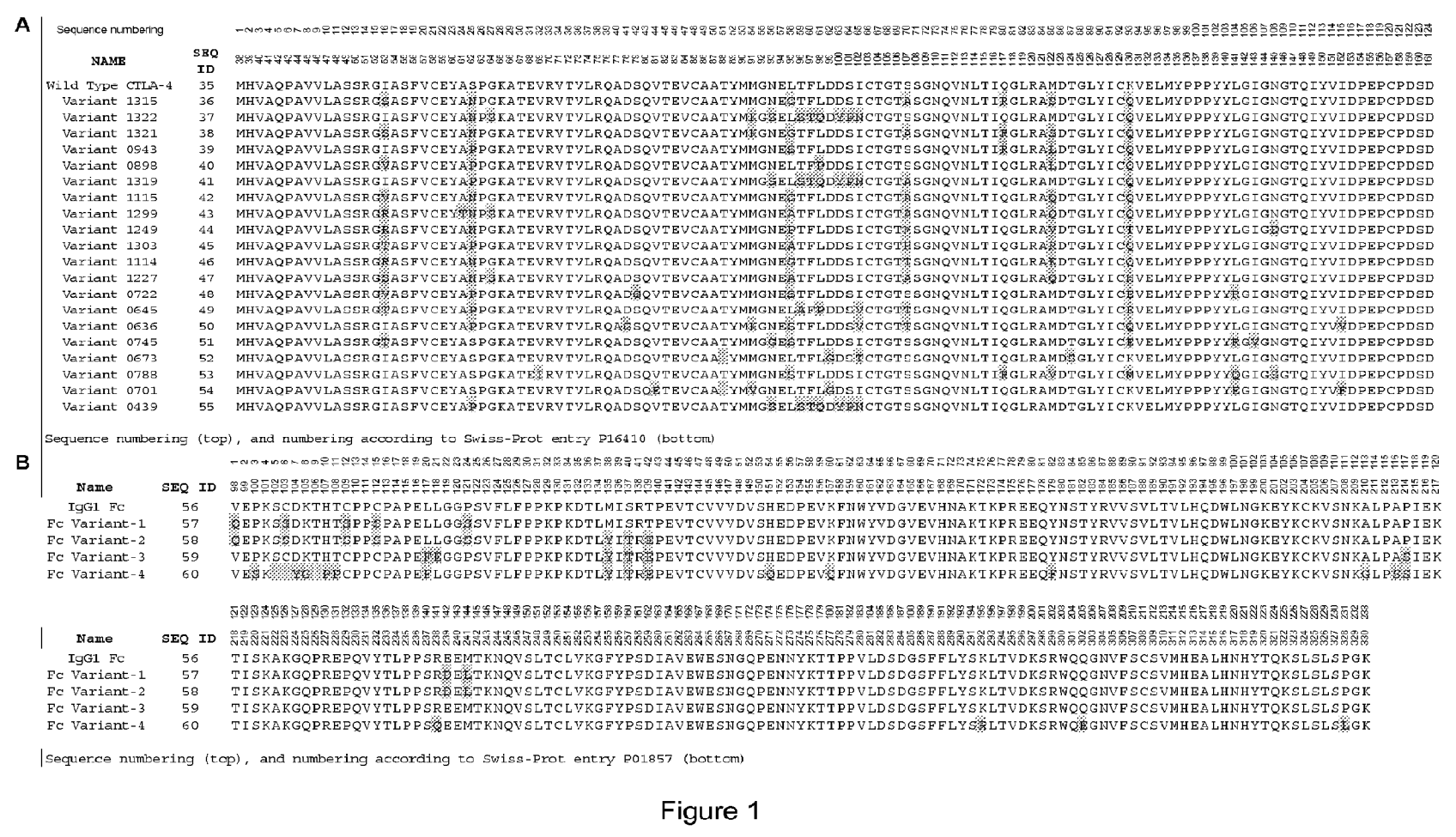
Figure 3:
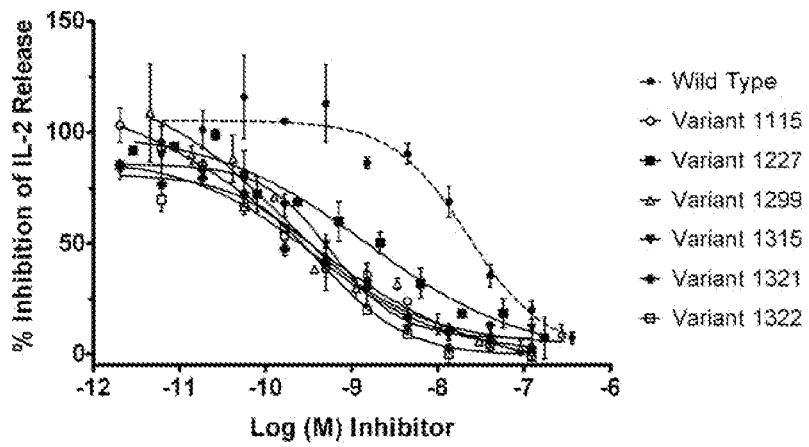
FIG. 3. IC$_{50}$ profiles of CTLA-4 variants and of wild type CTLA-4 in Fc fusion format in: (A) the Raji-Jurkat dual cell assay; (B) the primary human CD4+ T cell assay; (C) the cynomolgus monkey mixed lymphocyte reaction assay.
Figure 3:
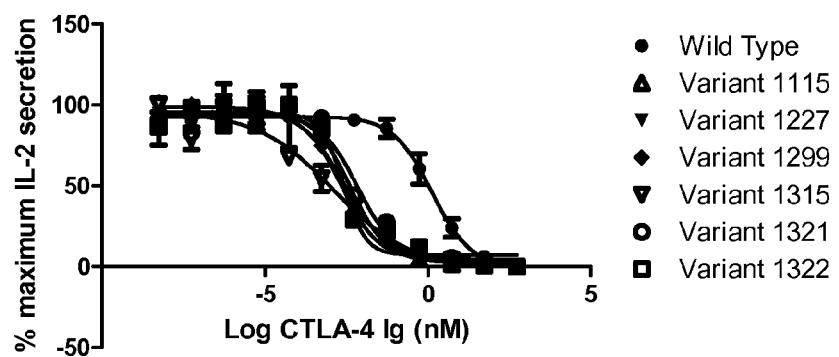
Figure 3:
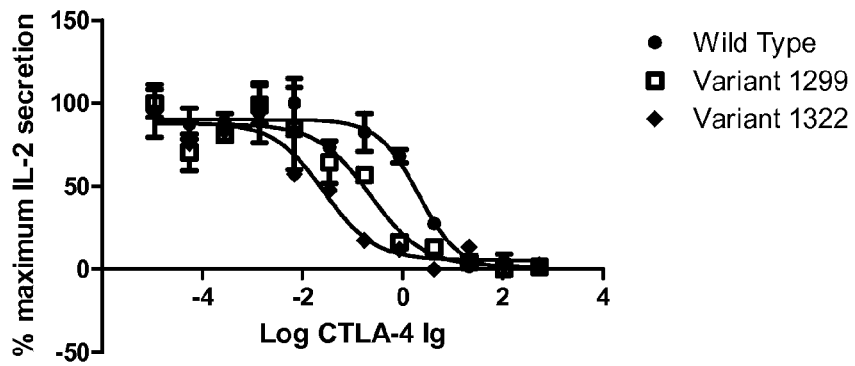

The numbering of the CTLA-4 residues which is used throughout this specification is as shown in FIG. 1A (top row, sequence numbering) and FIG. 2, unless otherwise stated. CTLA-4 has a leader sequence that is cleaved off, and at least two different numbering systems of the mature protein are possible. The CTLA-4 sequence can start with, inter alia, Ala at position 1 (U.S. Pat. No. 5,434,131) or with Met at position 1 (Larsen et al., Am. J. Transplantation (2005) 5:443-453). Unless context clearly dictates otherwise, the numbering system used herein is that wherein position 1 is Met. This also corresponds to the numbering which is generally used to refer to the residues of the product Abatacept.

The numbering of the Fc residues which is used throughout this specification is as shown in FIG. 1B (top row, starting from 1), unless otherwise stated.

The following numbered clauses represent aspects of the invention.

1. An isolated CTLA-4 polypeptide having greater affinity for binding human CD80, greater potency and/or greater stability compared with wild type CTLA-4 SEQ ID NO: 35, the polypeptide comprising an amino acid sequence that is a variant of SEQ ID NO: 35, wherein the variant comprises five or more of the following amino acid mutations in SEQ ID NO: 35:
R, S, V or T at I16;
T at A24;
N or P at S25;
S at G27;
I at V 32;
G at D41;
G at S42;
E at V44;
K at M54;
S or G at N56;
A, G, S or P at L58;
S or A at T59;
T at F 60;
Q or P at L61;
G at D 62;
Y at D63;
P at S 64;
N, D, V or T at I65;
A, T, M or H at S70;
R at Q80;
Q, S, V, R, K or L at M85;
S at T87;
Q, H, T, E or M at K93;
R, Q or E at L104;
V at I106;
D or S at N108;
V or F at I115;
S at C120;
deletion at T51.

2. A CTLA-4 polypeptide according to clause 1, wherein the polypeptide comprises an amino acid sequence at least 70% identical to SEQ ID NO: 35.

3. A CTLA-4 polypeptide according to clause 1 or clause 2, comprising five or more of the following amino acid mutations:
R, S or V at I16;
T at A24;
N at S25;
S at G27;
K at M54;
S at N56;
A or G at L58;
S at T59;
T at F60;
Q at L61;
Y at D63;
P at S64;
N or D at I65;
A at S70;
R at Q80;
Q or S at M85;
Q or H at K93;
S at C120.

4. A CTLA-4 polypeptide according to clause 1 or clause 2, comprising substitution S25N or S25P.

5. A CTLA-4 polypeptide according to any of clauses 1 to 3, comprising substitution S25N, K93Q or K93H.

6. A CTLA-4 polypeptide according to any of clauses 1 to 5, comprising an amino acid sequence at least 70%, 80%, 90%, 95% or 98% identical with any of SEQ ID NOS: 36-55, or an amino acid sequence at least 70%, 80%, 90%, 95%, 98 or 99% identical with the CTLA-4 amino acid sequence encoded by nucleic acid deposited under NCIMB accession no. 41948.

7. A CTLA-4 polypeptide according to any of clauses 1 to 6, comprising an amino acid motif SEQ ID NO: 69 at residues 59-65, the residue numbering being with reference to SEQ ID NO: 35.

8. A CTLA-4 polypeptide according to any of clauses 1 to 6, comprising a combination of mutations selected from:
the 1315 mutations i.e. S at I16; N at S25; G at L58; A at S70; R at Q80; S at M85; and Q at K93;
the 1322 mutations i.e. N at S25; S at G27; K at M54; S at N56; S at T59; T at F 60; Q at L61; Y at D63; P at S64; N at I65; and Q at K93;
the 1321 mutations i.e. S at I16; N at S25; K at M54; G at L58; A at S70; R at Q80; S at M85; and Q at K93;
the 1115 mutations i.e. V at I16; N at S25; G at L58; A at S70; Q at M85; and Q at K93;
the 1299 mutations i.e. R at I16; T at A24; N at S25; S at G27; A at L58; A at S70; Q at M85; and Q at K93; and
the 1227 mutations i.e. S at I16; N at S25; S at G27; A at L58; A at S70; Q at M85; and H at K93.

9. A CTLA-4 polypeptide according to any of the preceding clauses, comprising an amino acid sequence selected from SEQ ID NOS: 36-55 or comprising the CTLA-4 amino acid sequence encoded by nucleic acid deposited under NCIMB accession no. 41948, or comprising a variant of any of those sequences with up to ten amino acid mutations.

10. A CTLA-4 polypeptide according to any of the preceding clauses, comprising an amino acid sequence selected from SEQ ID NOS: 36-55 or comprising the CTLA-4 amino acid sequence encoded by nucleic acid deposited under NCIMB accession no. 41948, or comprising a variant of any of those sequences with up to five amino acid mutations.

11. A CTLA-4 polypeptide according to clause 10, comprising an amino acid sequence selected from SEQ ID NOS: 36-55 or comprising the CTLA-4 amino acid sequence encoded by nucleic acid deposited under NCIMB accession no. 41948, or comprising a variant of any of those sequences with up to three amino acid mutations.

12. A CTLA-4 polypeptide according to clause 1 or clause 2, comprising an amino acid sequence selected from SEQ ID NOS: 36-55 or comprising the CTLA-4 amino acid sequence encoded by nucleic acid deposited under NCIMB accession no. 41948.

13. A CTLA-4 polypeptide according to clause 12, comprising an amino acid sequence selected from SEQ ID NO: 43, SEQ ID NO: 37, SEQ ID NO: 38, SEQ ID NO: 36, SEQ ID NO: 42, SEQ ID NO: 47 or the CTLA-4 amino acid sequence encoded by nucleic acid deposited under NCIMB accession no. 41948.

14. An isolated CTLA-4 polypeptide having greater affinity for binding human CD80, greater potency and/or greater stability compared with wild type CTLA-4 SEQ ID NO: 35, wherein the polypeptide comprises:
(i) amino acid sequence SEQ ID NO: 68, SEQ ID NO: 43, SEQ ID NO: 37, SEQ ID NO: 38, SEQ ID NO: 36, SEQ ID NO: 42 or SEQ ID NO: 47;
(ii) an amino acid sequence that is a variant of (i) containing up to ten amino acid mutations, wherein residue 25 is not mutated and is N;
(iii) an amino acid sequence that is a variant of (i) comprising one or more amino acid mutations, wherein residue 25 is not mutated and is N, the variant having at least 70% sequence identity to (i); or
(iv) a CTLA-4 amino acid sequence encoded by nucleic acid deposited under NCIMB accession no. 41948.

15. A CTLA-4 polypeptide according to clause 14, comprising SEQ ID NO: 68, SEQ ID NO: 43, SEQ ID NO: 37, SEQ ID NO: 38, SEQ ID NO: 36, SEQ ID NO: 42 or SEQ ID NO: 47, or a variant of any of those sequences with up to five amino acid mutations.

16. A CTLA-4 polypeptide according to clause 15, comprising SEQ ID NO: 68, SEQ ID NO: 43, SEQ ID NO: 37, SEQ ID NO: 38, SEQ ID NO: 36, SEQ ID NO: 42 or SEQ ID NO: 47, or a variant of any of those sequences with up to three amino acid mutations.

17. A CTLA-4 polypeptide according to clause 14, wherein the polypeptide comprises an amino acid sequence having at least 80% sequence identity to SEQ ID NO: 68, SEQ ID NO: 43, SEQ ID NO: 37, SEQ ID NO: 38, SEQ ID NO: 36, SEQ ID NO: 42 or SEQ ID NO: 47.

18. A CTLA-4 polypeptide according to clause 17, wherein the polypeptide comprises an amino acid sequence having at least 90%, 95%, 98% or 99% sequence identity to SEQ ID NO: 68, SEQ ID NO: 43, SEQ ID NO: 37, SEQ ID NO: 38, SEQ ID NO: 36, SEQ ID NO: 42 or SEQ ID NO: 47.

19. A CTLA-4 polypeptide according to any of the preceding clauses, having an affinity of 50 nM or less for binding human CD80, wherein affinity is $K_D$ as determined by surface plasmon resonance.

20. A CTLA-4 polypeptide according to clause 19, having an affinity of 20 nM or less for binding human CD80, wherein the affinity is $K_D$ as determined by surface plasmon resonance.

21. A CTLA-4 polypeptide according to any of the preceding clauses, wherein the polypeptide has greater affinity than wild type CTLA-4 (SEQ ID NO: 35) for binding human CD86.

22. A CTLA-4 polypeptide according to any of clauses 14 to 21, comprising:
S at residue 16; N at residue 25; G at residue 58; A at residue 70; R at residue 80; S at residue 85; and Q at residue 93;
N at residue 25; S at residue 27; K at residue 54; S at residue 56; S at residue 59; T at residue 60; Q at residue 61; Y at residue 63; P at residue 64; N at residue 65; and Q at residue 93;
S at residue 16; N at residue 25; K at residue 54; G at residue 58; A at residue 70; R at residue 80; S at residue 85; and Q at residue 93;
V at residue 16; N at residue 25; G at residue 58; A at residue 70; Q at residue 85; and Q at residue 93;
R at residue 16; T at residue 24; N at residue 25; S at residue 27; A at residue 58; A at residue 70; Q at residue 85; and Q at residue 93; or
S at residue 16; N at residue 25; S at residue 27; A at residue 58; A at residue 70; Q at residue 85; and H at residue 93.

23. A CTLA-4 polypeptide according to any of clauses 14 to 22, comprising amino acid sequence SEQ ID NO: 43, SEQ ID NO: 37, SEQ ID NO: 38, SEQ ID NO: 36, SEQ ID NO: 42 or SEQ ID NO: 47, with up to three amino acid mutations.

24. A CTLA-4 polypeptide according to any of clauses 14 to 18, comprising: R, I, S or V at position 16; T or A at position 24; S or G at position 27; M or K at position 54; N or S at position 56; A, L or G at position 58; T or S at position 59;

F or T at position 60; L or Q at position 61; D or Y at position 63; S or P at position 64; I, N or D at position 65; A or S at position 70; Q or R at position 80; Q, M or S at position 85; Q or H at position 93; and C or S at position 120.

25. A CTLA-4 polypeptide according to any of clauses 14 to 18, wherein the amino acid mutations are selected from the following: substitution T at residue 16; substitution I at residue 32; substitution G at residue 41; substitution G at residue 42; substitution E at residue 44; substitution G at residue 56; substitution S or P at residue 58; substitution A at residue 59; substitution P at residue 61; substitution G at residue 62; substitution V or T at residue 65; substitution T, M or H at residue 70; substitution V, R, K or L at residue 85; substitution S at residue 87; substitution T, E or M at residue 93; substitution R, Q or E at residue 104; substitution V at residue 106; substitution D or S at residue 108; substitution V or F at residue 115; substitution S at residue 120; deletion at residue 51.

26. A CTLA-4 polypeptide according to clause 14, comprising amino acid sequence SEQ ID NO: 68, SEQ ID NO: 43, SEQ ID NO: 37, SEQ ID NO: 38, SEQ ID NO: 36, SEQ ID NO: 42 or SEQ ID NO: 47 or comprising a CTLA-4 amino acid sequence encoded by nucleic acid deposited under NCIMB accession no. 41948.

27. An isolated CTLA-4 polypeptide which has at least 10-fold greater affinity for binding CD80 than for binding CD86.

28. A CTLA-4 polypeptide according to clause 27, which has at least 50-fold greater affinity for binding CD80 than for binding CD86.

29. A CTLA-4 polypeptide according to clause 27 or clause 28, wherein the polypeptide is as defined in any of clauses 1 to 26.

30. A CTLA-4 polypeptide according to any of the preceding clauses, conjugated to an IgG Fc amino acid sequence.

31. A CTLA-4 polypeptide according to clause 30, wherein the IgG Fc is a human IgG1 Fc modified to reduce Fc effector function, and comprises a native human IgG1 Fc hinge region.

32. A CTLA-4 polypeptide according to clause 30 or clause 31, wherein the IgG Fc amino acid sequence comprises a human IgG1 Fc region in which one or both of the following groups of residues are substituted as follows:
 F at residue 20; E at residue 21; S at residue 117; and
 Y at residue 38, T at residue 40, E at residue 42,
 the residue numbering being defined with reference to SEQ ID NO: 56.

33. A CTLA-4 polypeptide according to any of clauses 30 to 32, wherein the IgG Fc amino acid sequence comprises SEQ ID NO: 59.

34. An isolated CTLA-4 polypeptide comprising the 1299 CTLA-4-Ig amino acid sequence encoded by nucleic acid deposited under NCIMB accession no. 41948.

35. A CTLA-4 polypeptide according to any of the preceding clauses, wherein the polypeptide is in a multimer.

36. A CTLA-4 polypeptide according to clause 35, wherein the CTLA-4 polypeptide is in a dimer.

37. A CTLA-4 polypeptide according to clause 35, wherein the CTLA-4 polypeptide is in a tetramer.

38. A CTLA-4 polypeptide according to clause 37, wherein the tetramer comprises two pairs of CTLA-4 polypeptides, each pair comprising a CTLA-4 polypeptide fused to an antibody light chain constant region and a CTLA-4 polypeptide fused to an antibody heavy chain constant region.

39. A host cell containing nucleic acid, wherein the nucleic acid comprises the 1299 CTLA-4-Ig nucleic acid sequence deposited under NCIMB accession no. 41948.

40. A composition comprising:
 a CTLA-4 polypeptide according to any of the preceding clauses; and
 one or more pharmaceutical excipients.

41. A composition comprising:
 a CTLA-4 polypeptide comprising amino acid sequence SEQ ID NO: 68, SEQ ID NO: 43, SEQ ID NO: 47, SEQ ID NO: 38, SEQ ID NO: 36, SEQ ID NO: 42 SEQ ID NO: 47 or the CTLA-4 amino acid sequence encoded by nucleic acid deposited under NCIMB accession no. 41948, conjugated to an IgG Fc amino acid sequence; and one or more pharmaceutical excipients.

42. A composition according to clause 40 or clause 41, wherein the CTLA-4 polypeptide is conjugated to an IgG Fc amino acid sequence comprising SEQ ID NO: 59.

43. A composition according to clause 42, wherein the CTLA-4 polypeptide conjugated to an IgG Fc comprises amino acid sequence SEQ ID NO: 13, SEQ ID NO: 11, SEQ ID NO: 12, SEQ ID NO: 14, SEQ ID NO: 15 or SEQ ID NO: 16.

44. A composition comprising the 1299 CTLA-4-Ig polypeptide encoded by nucleic acid deposited under NCIMB accession no. 41948 and one or more pharmaceutical excipients.

45. A composition according to any of clauses 40 to 44, comprising the CTLA-4 polypeptide at a concentration of at least 70 mg/ml.

46. A composition according to clause 45, comprising the CTLA-4 polypeptide at a concentration of at least 100 mg/ml.

47. A CTLA-4 polypeptide according to any of clauses 1 to 38, or a composition according to any of clauses 40 to 46, for use in a method of treatment of a patient by subcutaneous or intravenous administration.

48. A CTLA-4 polypeptide according to any of clauses 1 to 38, or a composition according to any of clauses 40 to 46, for use in a method of treatment of rheumatoid arthritis, multiple sclerosis, asthma, Crohn's disease, ulcerative colitis, systemic lupus erythematosus or transplant rejection.

49. A CTLA-4 polypeptide according to any of clauses 1 to 38, or a composition according to any of clauses 40 to 46, for use in a method of treatment comprising administering said CTLA-4 polypeptide or said composition to a patient at 28 day intervals.

50. A method of producing a further CTLA-4 polypeptide by mutation of a CTLA-4 polypeptide amino acid sequence selected from SEQ ID NOS 36-55 or the CTLA-4 amino acid sequence encoded by nucleic acid deposited under NCIMB accession no. 41948, the method comprising:
 providing a CTLA-4 polypeptide comprising or consisting of amino acid sequence SEQ ID NOS 36-55 or the CTLA-4 amino acid sequence encoded by nucleic acid deposited under NCIMB accession no. 41948;
 introducing one or more mutations in the amino acid sequence to provide a further CTLA-4 polypeptide;
 testing stability, affinity and/or potency of the further CTLA-4 polypeptide; and
 formulating the further CTLA-4 polypeptide into a composition comprising one or more pharmaceutical excipients.

51. A method according to clause 50, wherein the further CTLA-4 polypeptide is conjugated to an Fc region.

Biological Potency

Soluble CTLA-4 competes with CD28 expressed on the surface of T lymphocytes, inhibiting binding of the ligands CD80 (B7.1) and CD86 (B7.2) to the CD28 which would otherwise result in co-stimulation and activation of the T lymphocyte. Thus, soluble CTLA-4 inhibits activation of T lymphocytes. The potency of this inhibition by exogenous soluble CTLA-4 may be determined in in vitro assays. The CTLA-4 may optionally be conjugated to another molecule, e.g. as a fusion protein. For example, an IgG Fc may be present, as described elsewhere herein. The assay can be used to determine qualitatively whether a CTLA-4 polypeptide is more or less potent than wild type, using wild type CTLA-4 (optionally conjugated to the Fc, as the case may be) as a control, and can also provide quantitative information regarding the magnitude of difference in potency. Methods of performing such assays and of analysing the statistical significance of the data to reliably produce qualitative or quantitative information are known in the art.

Binding of a CTLA-4 polypeptide may be measured via the production of IL-2, since the binding of CTLA-4 to CD80 and CD86 attenuates IL-2 production. Suitable assays may comprise detecting the amount of IL-2 produced, for example by ELISA.

A reduction in the amount of IL-2 production may be partial or total. A CTLA-4 polypeptide may reduce IL-2 production by at least 50%, 75% or 80%, more preferably at least 85%, 90% or 95%, at the concentrations tested.

A dual cell assay can be used to identify CTLA-4 polypeptides with higher potency than wild-type. CTLA-4 polypeptides are assayed to measure inhibition of signalling. Co-culture of T-cells expressing CD28 (e.g. Jurkat cells) and B-cells expressing CD80 and CD86 (e.g. Raji cells) results in the production of IL-2, due to the interaction between CD28 and the ligands CD80 and CD86 in the presence of phytohemaglutinin (PHA). The IL-2 is then detected via ELISA. See Example 3 for a detailed worked example of this assay.

Primary human T cell activation assays can be used to further assess the potency of the selected polypeptides. CTLA-4 polypeptides may be ranked on their ability to inhibit CD80/86-mediated IL-2 secretion from primary human CD4+ T lymphocytes. CTLA-4 polypeptides can also be ranked on their ability to inhibit anti-CD3-stimulated proliferation of human CD4+ lymphocytes in the presence of Raji cells expressing CD80 and CD86. Proliferation may be assayed using a homogenous luminescence assay (ATP lite). An advantage of this assay is that it measures the potency of the CTLA-4 polypeptides to block activation of primary human CD4+ lymphocytes. See Example 4 for a detailed worked example of this assay.

Certain CTLA-4 polypeptides according to the invention have been shown to bind to CD80 and CD86 with high potency in an assay measuring T cell activation. CTLA-4 polypeptides block the ligands CD80 and CD86 thereby preventing the additional activation signals from these molecules and leading to reduced IL-2 production.

Potency of the CTLA-4 polypeptides may be determined or measured using one or more assays known to the skilled person and/or as described or referred to herein. Potency is a measure of activity expressed in terms of the amount required to produce an effect. Typically a titration of a polypeptide is compared in a cell assay and the $IC_{50}$ values reported. In functional assays, $IC_{50}$ is the concentration of a product that reduces a biological response by 50% of its maximum. $IC_{50}$ may be calculated by plotting % of maximal biological response as a function of the log of the product concentration, and using a software program such as Prism (GraphPad) to fit a sigmoidal function to the data to generate $IC_{50}$ values. The lower the $IC_{50}$ value, the more potent the product.

CTLA-4 polypeptides can be described as having increased potency as less is needed compared with a reference (e.g. wild type) CTLA-4 polypeptide, to produce inhibition of the IL-2 production. This is also reflected in the reported $IC_{50}$ values. Preferred CTLA-4 polypeptides have increased potency compared with human wild type CTLA-4 (SEQ ID NO: 35).

A CTLA-4 polypeptide according to the invention may have greater potency than wild type CTLA-4 comprising SEQ ID NO: 35, wherein potency is a reduction in $IC_{50}$ in an assay of IL-2 production using T-cells activated by B-cells. Potency may be at least 10-fold, at least 15-fold, at least 20-fold, at least 30-fold, at least 40-fold or at least 50-fold greater than wild type. As described in the Examples herein, one polypeptide SEQ ID NO: 36 (variant 1315) was shown to have approximately 120-fold greater potency than wild type CTLA-4. Potency may, for example, be up to 150-fold, up to 130-fold, up to 120-fold, up to 100-fold, up to 80-fold, up to 70-fold, or up to 60-fold greater than wild type. The potency improvement may, for example, be in the range of 10-fold to 100-fold greater than wild type.

Potency of a CTLA-4 polypeptide can be determined with reference to CTLA-4 polypeptide sequences exemplified herein, rather than (or as well as) with reference to wild type e.g. potency can be compared with any of SEQ ID NO: 37 (variant 1322), SEQ ID NO: 38 (variant 1321), SEQ ID NO: 43 (variant 1299), SEQ ID NO: 36 (variant 1315), SEQ ID NO: 42 (variant 1115), SEQ ID NO: 47 (variant 1227) or variant 1299 as encoded by nucleic acid deposited under NCIMB accession no. 41948. Thus, one of these CTLA-4 variants may be used as a control in the assay. A CTLA-4 polypeptide may be at least as potent as one or more of these variants, e.g. at least as potent as SEQ ID NO: 43 (variant 1299) or SEQ ID NO: 47 (variant 1227). A CTLA-4 polypeptide may have a potency which is about the same or less than the potency of SEQ ID NO: 36 (variant 1315).

Affinity

Affinity of a CTLA-4 polypeptide for binding CD80 or CD86 can be determined as monovalent affinity, using surface plasmon resonance to determine $K_D$. See Example 8 for a worked example of the use of surface plasmon resonance to measure binding affinity and determine $K_D$. The resulting $K_D$ may be compared with that of wild type CTLA-4 SEQ ID NO: 35 or compared with that of one of the CTLA-4 polypeptides SEQ ID NO: 37 (variant 1322), SEQ ID NO: 38 (variant 1321), SEQ ID NO: 43 (variant 1299), SEQ ID NO: 36 (variant 1315), SEQ ID NO: 42 (variant 1115), r SEQ ID NO: 47 (variant 1227) or variant 1299 as encoded by nucleic acid deposited under NCIMB accession no. 41948 to determine relative affinity. A CTLA-4 polypeptide may have greater affinity for binding human CD86 and/or human CD80, compared with the affinity of wild type CTLA-4.

A CTLA-4 polypeptide may have an affinity for binding human CD80 that is greater than that of wild type CTLA-4, e.g. at least 10-fold, at least 15-fold, at least 20-fold, at least 30-fold, at least 40-fold, at least 50-fold, at least 100-fold or at least 140-fold greater than wild type. The CTLA-4 polypeptide may have at least the affinity for binding human CD80 of one or more of SEQ ID NO: 43, SEQ ID NO: 37, SEQ ID NO: 38, SEQ ID NO: 36, SEQ ID NO: 42 and SEQ ID NO: 47 or at least the affinity of CTLA-4 variant 1299 as encoded by nucleic acid deposited under NCIMB accession no. 41948. A CTLA-4 polypeptide may have an affinity for binding human CD80 which is about the same or less than the affinity of SEQ ID NO: 37. The $K_D$ for binding human CD80 may be 50 nM or less, e.g. 25 nM or less, 20 nM or less, or 10 nM or less. For example, the $K_D$ may be in the range 5 to 50 nM.

A CTLA-4 polypeptide may have an affinity for binding human CD86 that is greater than that of wild type CTLA-4, e.g. at least 2-fold, at least 3-fold, at least 4-fold, at least 5-fold or at least 10-fold greater than wild type. The CTLA-4 polypeptide may have at least the affinity for binding human CD86 of one or more of SEQ ID NO: 43, SEQ ID NO: 37, SEQ ID NO: 38, SEQ ID NO: 36, SEQ ID NO: 42 and SEQ ID NO: 47 or at least the affinity of CTLA-4 variant 1299 as encoded by nucleic acid deposited under NCIMB accession no. 41948. A CTLA-4 polypeptide may have an affinity for binding human CD86 which is about the same or less than the affinity of SEQ ID NO: 37. The $K_D$ for binding human CD86 may be 2 μM or less, e.g. 1.5 μM or less or 1 μM or less. For example, the $K_D$ may be in the range 0.5 to 2 μM.

Selectivity for CD80 Over CD86

CTLA-4 polypeptides described herein may bind both CD80 and CD86, but may selectively bind CD80 in preference to CD86. Wild type CTLA-4 is known to have higher affinity for binding CD80 compared with CD86, and a CTLA-4 polypeptide according to the invention may also have greater affinity for binding CD80 than for binding CD86. However, a CTLA-4 polypeptide may have a greater selectivity for binding CD80 in preference to CD86, compared with wild type CTLA-4. For example, in surface plasmon resonance assays, as described herein, wild type CTLA-4 exhibited approximately 4-fold greater affinity for binding CD80 than for binding CD86. In contrast, CTLA-4 polypeptides may exhibit over 10-fold, over 20-fold, over 30-fold, over 40-fold or over 50-fold greater affinity for binding CD80 than for binding CD86. For example, a CTLA-4 polypeptide may exhibit up to 120-fold or 130-fold greater affinity for binding CD80 than for binding CD86. Thus, when compared with the affinity of wild type CTLA-4, a CTLA-4 polypeptide may exhibit a greater increase in binding affinity for CD80 than for CD86. The selective preference for CD80 over CD86 may be seen with human CD80 and human CD86.

Furthermore, the same selective preference may be retained with CD80 and CD86 from cynomolgus monkey. The fold difference in affinity for binding CD80 over CD86 may be approximately the same for human and cynomolgus CD80 and CD86.

Improvements in affinity for binding CD80 should confer a better biological profile for medical use. By binding to CD80, which is upregulated on antigen presenting cells in the context of an active immune response, CTLA-4 inhibits binding of CD80 to CD28 on T cells, thereby blocking the activation signal to the T cell. Thus, a CTLA-4 polypeptide may be used to attenuate the T cell response in vivo and to treat conditions in which this is beneficial, as described elsewhere herein.

By engineering a CTLA-4 polypeptide which selectively targets CD80 over CD86, very large affinity gains for binding CD80 can be obtained. Although the literature is inconclusive regarding the relative roles of CD80 and CD86, the polypeptides of the present invention selectively bind CD80 over CD86 and exhibit excellent biological profiles suitable for therapeutic use, as shown in the various assays. Without being bound by theory, the attributes of the present CTLA-4 polypeptides may attributable at least in part to the high affinity for binding CD80 and/or to the preferential binding of CD80 over CD86.

Various data point towards a role for CD80 delivering an increased activation signal to T lymphocytes. For example:

CD80-transduced CHO cells induce increased IL-2 production from primary human T cells compared with CD86-transduced CHO cells (Slavik et al. *JBC* 274(5):3116-3124 1999);

CD80 induces increased NFκB and AP-1 transcription factor activity compared with CD86 in Jurkat T cells (factors important for cytokine production such as IL-2) (Olsson et al. *Int. Immunol.* 10(4):499-506 1998);

CD80 induces increased CD25 expression in CD8+ T cells interacting with virus-infected dendritic cells compared with CD86 (important for T cell survival and proliferation) (Pejawar-Gaddy & Alexander-Miller *J. Immunol.* 177:4495-4502 2006); and in a murine model of allergic asthma, using a mutated CTLA-4 Ig molecule, CD80 but not CD86 was found to be a major driver of lung eosinophilia (Harris et al. *J. Exp. Med.* 185(1) 1997).

Preferentially increasing the affinity of CTLA-4 to CD80 may thus lead to improved inhibition of T cell activation by targeting the more efficient CD80 T cell activation pathway.

Further, there is some evidence that CD86 signalling can have a beneficial anti-inflammatory effect in some disease models. For example, in a mouse sepsis model, severity and mortality were observed to be associated with upregulation of CD80 and concomitant downregulation of CD86 (Nolan et al. *PLoS ONE* 4(8):6600 2009). Thus, a selective binding of CD80 over CD86 may provide an advantage since it can inhibit CD80 binding to CD28, while reducing the interaction of CD28 to a lesser extent.

Both CD80 and CD86 positive cells can be found in the joints of rheumatoid arthritis patients, and binding of both these B7 molecules may contribute to therapeutic efficacy, while selectivity for CD80 over CD86 may further contribute to desirable quantitative and qualitative effects in inhibiting T cell activation. Accordingly, CTLA-4 polypeptides of the invention may bind both CD80 and CD86, and may have higher affinity for CD80 than that of wild type CTLA-4, and may also have higher affinity for CD86 than that of wild type CTLA-4.

Cross-Reactivity

Preferably, CTLA-4 polypeptides according to the invention retain the cross-reactivity profile of wild type CTLA-4.

A CTLA-4 polypeptide may show cross-reactivity for binding cynomolgus and/or mouse CD80 and CD86, as well as human CD80 and CD86. The difference in affinity for cynomolgus CD80 compared with human CD80 may be within 10-fold, within 5-fold, within 2-fold, within 1.5-fold or within 1.2-fold. The difference in affinity for cynomolgus CD86 compared with human CD86 may be within 10-fold, within 5-fold, within 2-fold, within 1.5-fold or within 1.2-fold. The difference in affinity for mouse CD80 compared with human CD80 may be within 10-fold, within 5-fold, within 2-fold, within 1.5-fold or within 1.2-fold. The difference in affinity for mouse CD86 compared with human CD86 may be within 10-fold, within 5-fold, within 2-fold, within 1.5-fold or within 1.2-fold.

A CTLA-4 polypeptide may inhibit activation of cynomolgus T lymphocytes, e.g. measured as inhibition of IL-2 production in a mixed lymphocyte reaction using peripheral blood mononuclear cells from cynomolgus monkeys. The polypeptide may show greater potency than wild type CTLA-4 in an assay for inhibition of activation of cynomolgus T lymphocytes.

Data on species cross-reactivity for example CTLA-4 polypeptides of the invention are shown in Example 8.

A CTLA-4 polypeptide may show specific binding for CD80 and CD86 in preference to other related proteins in the B7 family. Thus, there may be a lack of cross-reactivity with PD-L2, B7-H1, B7-H2, B7-H3 and B7-H3B.

Assays for determining specificity are known in the art. For example, an enzyme immunoassay may be used. See Example 6 for a worked example of a suitable assay.

Stability

A CTLA-4 polypeptide preferably retains at least the stability of wild type CTLA-4, and is preferably more stable than wild type, e.g. as measured for CTLA-4 alone or CTLA-4 conjugated (e.g. fused) to an Fc region as described below.

It is believed that more stable CTLA-4 Fc conjugates ("CTLA-4 Ig") will be better able to tolerate formulation at the high (e.g. ≥100 mg/ml) concentrations required for subcutaneous delivery.

Stability may be tested in a degradation assay. Typically, this comprises incubating the product at a fixed temperature (e.g. 5° C. or 25° C.) for a period of time, e.g. for a month, and determining the extent of loss of purity (extent of degradation) over that month. Aggregation and/or fragmentation may contribute to loss of purity, and each may be measured separately to determine a percentage, to two values adding up to % loss of purity. Worked examples of degradation assays are set out in Example 9 and Example 10.

A CTLA-4 polypeptide with improved stability may be more amenable to routes of administration such as subcutaneous administration, because of reduced aggregation, which not only increases efficacy but also reduces the risk of neutralising or binding antibodies being elicited.

Conjugation to Fc

In one embodiment the invention provides an affinity optimised CTLA-4 Ig molecule, optionally with extended half-life (e.g. including a YTE mutation, further described herein), for subcutaneous or intravenous formulation, and for monthly, 28-day interval or less frequent dosing for the treatment of moderate to severe RA or other conditions as described.

The invention provides a polypeptide that consists of a CTLA-4 polypeptide sequence or that comprises or is conjugated to a peptide or polypeptide sequence, e.g. to an antibody molecule or part of an antibody molecule. For example, a CTLA-4 polypeptide may be conjugated to an antibody Fc amino acid sequence, e.g. IgG Fc. An Fc region comprises a hinge, a CH2 and a CH3 region. Preferably, the IgG is human IgG e.g. IgG1, IgG2 or IgG4.

Allotype variants of IgG1 are known. Preferably, an IgG1 Fc region comprises E at residue 142 and M at residue 144 (numbering corresponding to SEQ ID NO: 56, starting from 1 as shown in FIG. 1). This allotype is well represented in the general population. An alternative IgG1 Fc region, representing a different allotype, comprises D at residue 142 and L at residue 144. This allotype is employed in Abatacept.

The IgG Fc amino acid sequence may comprise the amino acid sequence of human IgG (e.g. IgG1 or IgG4) Fc with certain mutations. For example, where the human IgG is IgG1, the amino acid sequence may be mutated to reduce or abolish Fc effector functions, e.g. complement dependent cytotoxicity (CDC) and antibody dependent cell cytotoxicity (ADCC). The removal of Fc effector functions may be confirmed in known routine assays. See Example 7 for exemplary assays to determine ADCC and CDC.

It is known that IgG1 effector function can be reduced by mutation of the IgG1 Fc hinge region. An example of this is in the Abatacept CTLA-4-IgG1 Fc construct, which incorporates a mutated hinge sequence in the IgG1 Fc region, in which wild type C is mutated to S. The IgG1 region of Abatacept includes an amino acid sequence SEQ ID NO: 71, which corresponds to wild type human IgG1 Fc amino acid sequence SEQ ID NO: 70 with wild type C substituted by S. The substitutions are at residues 6, 12 and 15 of the Fc region.

SEQID NO: 70
VEPKSCDKTHTCPPCPAPE

SEQID NO: 71
QEPKS<u>S</u>DKTHT<u>S</u>PP<u>S</u>PAPE

In the context of the present invention it has been surprisingly discovered that this mutation reduces the stability of the Fc domain, so that the Abatacept CTLA4-IgG1 Fc fusion has overall lower stability than a CTLA-4-IgG1 Fc fusion in which the wild type IgG1 Fc sequence is used. This loss of stability is undesirable, but it is nevertheless important to reduce or avoid IgG1 Fc effector function.

An Fc region conjugated to a CTLA-4 polypeptide of the invention preferably does not comprise SEQ ID NO: 71. Preferably, the cysteines at residue 6, 12 and/or 15 of the Fc are retained. Preferably, a CTLA-4-Fc conjugate according to the invention comprises a wild type human IgG1 Fc hinge region. Preferably the Fc region comprises SEQ ID NO: 70. The Fc region may be the Fc region of the 1299 CTLA4-Ig polypeptide as encoded by nucleic acid deposited under NCIMB accession no. 41948.

Whilst the reversion of the Abatacept Fc to wild type removes the instability caused by the Fc mutation, this also restores the effector functions of the IgG1 Fc, which is undesirable in many therapeutic applications. Accordingly, this mutation improves stability of the Abatacept Fc domain but only at the expense of re-introducing undesirable effector function.

Other IgG Fc regions with lower or no effector function may be used, e.g. IgG2.

The present invention provides a way to use IgG1 Fc lacking effector functions, while overcoming the problem of reduced stability inherent in the Abatacept mutation. An Fc region according to the invention may be an IgG1 Fc comprising a triple mutation (TM) L20F, L21E, P117S (Oganesyan et al 2008 Acta Crystallogr D Biol Crystallogr. 64:700-4). This mutation reduces Fc effector function, without reducing stability. Accordingly, such an Fc domain facilitates the formulation of CTLA-4-Fc constructs at high concentrations, which are suitable for production of compositions for subcutaneous administration.

Still further benefits can be achieved through incorporation of a "YTE" mutation in the Fc region (Dall'Acqua et al 2006 J Biol Chem. 281:23514-24). The YTE mutation provides an extended in vivo half life, which may improve therapeutic efficacy and/or may allow therapeutic benefits to be achieved at reduced or less frequent dosage, such as monthly dosage. An Fc domain used in the products of the invention may comprise Y at residue 38, T at residue 40, and E at residue 42. This represents a mutation M38Y, S40T, T42E from human IgG1 Fc.

Other than the YTE and/or triple mutation noted above, it is preferable that other residues of the Fc domain are wild type human IgG residues. Some variation in human IgG1 Fc is known, and the Fc region may comprise any human IgG1 with the YTE and/or triple mutation.

Preferably, a CTLA-4 polypeptide is conjugated to an IgG Fc amino acid sequence SEQ ID NO: 59. This includes a human IgG1 Fc hinge region, lacks the Abatacept mutation of C to S, incorporates the triple mutation to reduce effector function and includes the YTE half life extension.

The improved Fc regions described herein may be used in conjunction with wild type CTLA-4, but provide yet further benefits when conjugated to a CTLA-4 polypeptide according to the invention. A CTLA-4 polypeptide may be conjugated at its C terminus to the N terminus of an Fc region, optionally via one or more linking amino acids or a linker peptide. Preferably, the conjugate is a CTLA-4-Fc fusion protein.

For example, a CTLA-4 polypeptide comprising amino acid sequence SEQ ID NO: 43, SEQ ID NO: 37, SEQ ID NO: 38, SEQ ID NO: 36, SEQ ID NO: 42 or SEQ ID NO: 47 may be conjugated to IgG Fc amino acid sequence SEQ ID NO: 59 or to IgG Fc amino acid sequence SEQ ID NO: 60.

A CTLA-4-IgG Fc fusion protein according to the invention may comprise SEQ ID NO: 13, SEQ ID NO: 11, SEQ ID NO: 12, SEQ ID NO: 14, SEQ ID NO: 15 or SEQ ID NO: 16.

The 1299 CTLA-4-IgG Fc polypeptide encoded by nucleic acid deposited under NCIMB accession no. 41948 is an embodiment of the invention. The 1299 CTLA-4 polypeptide encoded by the nucleic acid deposited under NCIMB accession no. 41948 may alternatively be conjugated to a different Fc region if desired.

CTLA-4 Polypeptide Products

CTLA-4 polypeptides, including CTLA-4-Fc, may be monomeric or multimeric, e.g. dimeric, trimeric, tetrameric or pentameric. As discussed elsewhere herein, CTLA-4 may form dimers. This natural dimerisation may be promoted by conjugating the CTLA-4 to an Fc domain or other dimerising domain.

Polypeptide multimers comprising a plurality of CTLA-4 polypeptides are an aspect of the invention. The plurality of CTLA-4 polypeptides within the multimer may be identical or different from one another. A multimer may comprise some identical polypeptides and/or some different polypeptides. A multimer may comprise one or more CTLA-4 polypeptides according to the invention, and one or more other polypeptides. The one or more other polypeptides may include, for example, a wild type CTLA-4 and/or a polypeptide that is not a CTLA-4 polypeptide.

The multimer may be a dimer comprising two CTLA-4 polypeptides according to the invention, which may be identical (a homodimer) or different (a heterodimer).

The multimer may be a tetramer comprising four CTLA-4 polypeptides according to the invention, which may all be identical (a homotetramer), or may include one or more different CTLA-4 polypeptides according to the invention (a heterotetramer). The multimer may be a tetramer comprising two CTLA-4 polypeptides according to the invention (identical or different from one another) and two other CTLA-4 polypeptides, such as wild type CTLA-4.

Where CTLA4 is in multimeric form, the CTLA-4 polypeptide is optionally conjugated with an immunoglobulin Fc region and/or an antibody molecule. The conjugate may or may not include an antibody antigen binding site, VH domain or VL domain.

One aspect of the invention is a conjugate comprising one or more, e.g. two, three, four or five CTLA-4 polypeptides and an antibody molecule or antibody domain, preferably human. Dimerised CTLA-4 domains may be conjugated to antibody heavy-light chain pairs. An antibody molecule may comprise two heavy-light chain pairs, each heavy chain comprising a VH domain and one or more constant heavy chain domains (e.g. CH1, CH2 and CH3), and each light chain comprising a VL domain and a light chain constant region, wherein the two heavy-light chain pairs are linked through dimerisation of the heavy chain constant domains, and wherein four CTLA-4 polypeptides are conjugated to the antibody molecule, one CTLA-4 being attached to each of the four variable domains. A light chain constant region may be a lambda or kappa light chain. A pair of CTLA-4 molecules may be attached to each VH-VL domain pair, wherein the CTLA-4 polypeptide attached to the VH domain forms a dimer with the CTLA-4 polypeptide attached to the VL domain. Preferably, the C terminus of CTLA-4 is fused to the N terminus of the VH or VL domain. Preferably the VH and VL pairing would not confer any binding to known human antigens.

Optionally, some or all of the antibody VH and/or VL domain is deleted, so that a CTLA-4 polypeptide is included in place of, or in place of part of, the VH and/or VL domain. A dimer may accordingly comprise a pair of CTLA-4 polypeptides, one fused to an antibody light chain constant region and one fused to an antibody heavy chain constant region. A tetramer may accordingly comprise two pairs of CTLA-4 polypeptides, each pair comprising a CTLA-4 polypeptide fused to an antibody light chain constant region and a CTLA-4 polypeptide fused to an antibody heavy chain constant region. As noted above, a heavy chain constant region comprises one or more heavy chain constant domains, e.g. CH1, CH2 and CH3, and a light chain constant region may be lambda or kappa.

The invention also includes CTLA4 pentamers. Five CTLA4 polypeptides may be assembled to form a pentamer, optionally through pentamerisation of attached antibody Fc regions. Pentamer formation is facilitated using the Fc region of IgM, which is naturally pentameric. Thus, five CTLA4-Fc polypeptides including the Fc region of IgM, preferably human IgM, may be arranged as a pentamer. Pentameric CTLA4 has been described (Yamada et al. *Microbiol. Immunol.* 40(7):513-518 1996).

Polypeptides within a multimer may be linked covalently, e.g. by disulphide bonds. Covalent links may be present between the CTLA4 polypeptide and/or between any Fc region linked to the CTLA-4 polypeptide. Where Fc regions and/or other antibody domains are employed, the polypeptides may be linked in the same manner as occurs naturally for such Fc domains and/or other antibody domains. Formation of disulphide bonds between cysteine residues of CTLA-4 polypeptides is described elsewhere herein.

Figure 7:
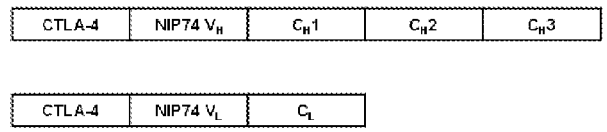
FIG. 7. (A) Construct design for the tetrameric CTLA-4 protein. (B) Potency comparison in the Raji Jurkat assay for Wild Type CTLA-4 in Fc fusion format versus tetrameric CTLA-4.
Figure 7:
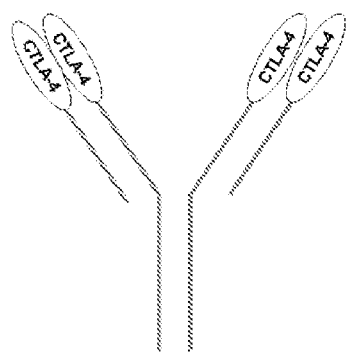
Figure 7:
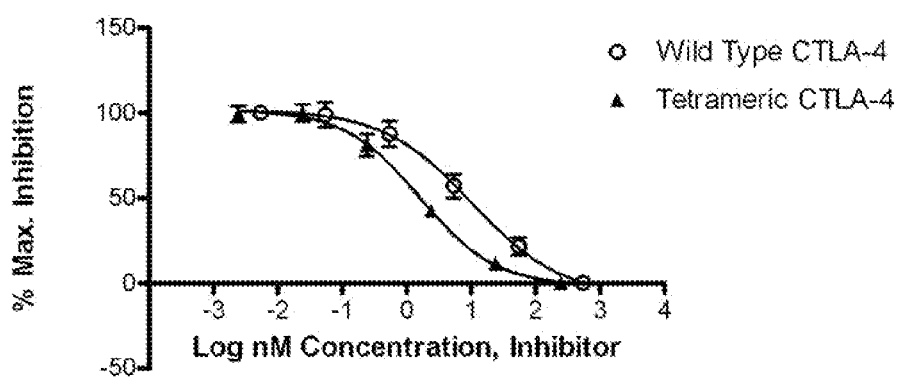

Such multimers and conjugates may be used in any method or for any use as described herein for CTLA-4 polypeptides. The multimeric structure may promote the biological activity of CTLA-4, e.g. inhibition of T cell activation. Inhibition of wild type CTLA-4 is shown to be enhanced in tetrameric form (Example 11, FIG. 7).

A CTLA-4 polypeptide may be labelled or unlabelled. A label may be added to the CTLA-4 sequence or to an Fc region conjugated to it.

The CTLA-4 and/or the Fc region may be glycosylated or unglycosylated. Preferably, the CTLA-4 and/or the Fc bear their normal human glycosylation.

CTLA-4 polypeptides as described herein may be further modified and developed to provide improved or altered additional variants. For example, the amino acid sequence of a CTLA-4 polypeptide according to the invention described herein may be modified by introducing one or more mutations, e.g. substitutions, to provide a further CTLA-4 polypeptide, which may then be tested for potency, affinity (for CD80 and/or CD86) and/or stability, e.g. as described elsewhere herein.

CTLA-4 polypeptides preferably retain one or more desired functional properties as described herein. Such properties include ability to bind CD80 and/or CD86, ability to bind CD80 and/or CD86 with an affinity greater than wild type CTLA-4, and/or a potency, affinity and/or stability as described herein for CTLA-4 polypeptides of the invention, e.g. a $K_D$ for binding human CD80 of 50 nM or less as determined by surface plasmon resonance. As described herein, a CTLA-4 polypeptide according to the invention typically has a greater affinity for binding human CD80, greater potency and/or greater stability, compared with wild type CTLA-4 SEQ ID NO: 35.

A CTLA-4 polypeptide may comprise or consist of an amino acid sequence having at least 70%, at least 80%, at least 90%, at least 95%, at least 98% or at least 99% with any of SEQ ID NOS: 36-55, for example with SEQ ID NO: 43, SEQ ID NO: 37, SEQ ID NO: 38, SEQ ID NO: 36, SEQ ID NO: 42 or SEQ ID NO: 47. A CTLA-4 polypeptide may comprise or consist of an amino acid sequence having at least 70%, at least 80%, at least 90%, at least 95%, at least 98% or at least 99% with SEQ ID NO: 68. A CTLA-4 polypeptide may comprise or consist of an amino acid sequence having at least 70%, at least 80%, at least 90%, at least 95%, at least 98% or at least 99% with the CTLA-4 amino acid sequence encoded by nucleic acid deposited under NCIMB accession no. 41948.

A CTLA-4 polypeptide may comprise or consist of any of SEQ ID NOS: 36-55, SEQ ID NO: 68 or the CTLA-4 amino acid sequence encoded by nucleic acid deposited under NCIMB accession no. 41948 with one or more amino acid mutations. For example it may comprise up to twelve, e.g. up to ten amino acid mutations, e.g. up to five mutations, e.g. one, two or three amino acid mutations. Examples of mutations are described elsewhere herein.

Following introduction of one or more mutations, a CTLA-4 polypeptide may be tested for desired functional properties such as ability to bind CD80 and/or CD86, ability to bind CD80 and/or CD86 with an affinity greater than wild type CTLA-4, and/or a potency, affinity and/or stability as described herein for CTLA-4 polypeptides of the invention, e.g. a $K_D$ for binding human CD80 of 50 nM or less as determined by surface plasmon resonance.

One aspect of the invention is a method comprising
providing a CTLA-4 polypeptide comprising or consisting of a CTLA-4 polypeptide amino acid sequence as described herein;
introducing one or more mutations in the amino acid sequence to provide a further CTLA-4 polypeptide; and
testing stability, affinity and/or potency of the further CTLA-4 polypeptide.

The CTLA-4 polypeptide amino acid sequence may comprise or consist of, for example, any of SEQ ID NOS 36-55 or SEQ ID NO: 68 or the CTLA-4 amino acid sequence encoded by nucleic acid deposited under NCIMB accession no. 41948. For example, the amino acid sequence may be SEQ ID NO: 43, 37, 36, 38, 42 or 47.

Between one and twenty mutations inclusive may optionally be introduced, and may comprise substitutions, deletions, insertions or a mixture of any of these. For example, one or more substitutions, e.g. between one and twenty substitutions inclusive may be introduced.

Examples of assays for testing stability, affinity and/or potency of the further CTLA-4 polypeptide are described herein. The further polypeptide may have a stability, affinity and/or potency which is not significantly lower, or which is greater, than the CTLA-4 polypeptide from which it was derived.

The method may comprise determining that the further CTLA-4 polypeptide has a potency, affinity and/or stability as described herein for CTLA-4 polypeptides of the invention, e.g. that it has a $K_D$ for binding human CD80 of 50 nM or less as determined by surface plasmon resonance.

A further CTLA-4 polypeptide identified as having a potency, affinity and/or stability as described herein for CTLA-4 polypeptides of the invention may then formulated into a pharmaceutical composition or used in methods including therapeutic methods as described herein.

The method may comprise formulating the further CTLA-4 polypeptide into a composition comprising one or more pharmaceutically acceptable excipients. Such compositions, their use and formulation are described in more detail elsewhere herein. The CTLA-4 polypeptide may be provided in any format described herein, e.g. it may be conjugated to an Fc region as described.

A nucleic acid molecule encoding a CTLA-4 polypeptide, e.g. a CTLA-4-Fc construct, may be produced. For example, a nucleic acid molecule may encode any CTLA-4 polypeptide amino acid sequence or CTLA-4-Fc amino acid sequence according to the invention. The nucleic acid may comprise the nucleic acid sequence deposited under NCIMB accession no. 41948 encoding the 1299 CTLA-4-Ig polypeptide, or encoding at least the CTLA-4 polypeptide region thereof. The nucleic acid molecule may be isolated, and may be comprised in a vector, e.g. a recombinant vector for expression of the nucleic acid in a cell. A cell in vitro may comprise the vector, and may be used for expression of the CTLA-4 polypeptide or CTLA-4 Fc product. The polypeptide may be expressed by the *E. coli* cell line of NCIMB deposit accession number 41948.

A CTLA-4 polypeptide as described herein may be produced by a method including expressing the polypeptide from encoding nucleic acid. This may conveniently be achieved by growing a host cell in culture, containing such a vector, under appropriate conditions which cause or allow expression of the CTLA-4 polypeptide. CTLA-4 polypeptides may also be expressed in in vitro systems, such as reticulocyte lysate. Following production of a CTLA-4 polypeptide by expression, its activity, for example its ability to bind to CD86 or CD80 can be tested routinely.

Systems for cloning and expression of a polypeptide in a variety of different host cells are well known, and may be employed for expression of the CTLA-4 polypeptides described herein, including CTLA-4-Fc polypeptides. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. bacteriophage, or phagemid, as appropriate. Many techniques and protocols for manipulation of nucleic acid, for example in preparation of nucleic acid constructs, mutagenesis, sequencing, introduction of DNA into cells and gene expression, and analysis of proteins, are known.

Generally, nucleic acid encoding a CTLA-4 polypeptide according to the present invention is provided as an isolate, in isolated and/or purified form, or free or substantially free of contaminants. Nucleic acid may be wholly or partially synthetic and may include genomic DNA, cDNA or RNA.

Nucleic acid may be provided as part of a replicable vector, and also provided by the present invention are a vector including nucleic acid encoding a CTLA-4 polypeptide of the invention, particularly any expression vector from which the encoded polypeptide can be expressed under appropriate conditions, and a host cell containing any such vector or nucleic acid. An expression vector in this context is a nucleic acid molecule including nucleic acid encoding a polypeptide of interest and appropriate regulatory sequences for expression of the polypeptide, in an in vitro expression system, e.g. reticulocyte lysate, or in vivo, e.g. in eukaryotic cells such as COS or CHO cells or in prokaryotic cells such as E. coli.

A host cell may contain nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

The nucleic acid may be introduced into a host cell. The introduction, which may (particularly for in vitro introduction) be generally referred to without limitation as "transformation" or "transfection", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

A CTLA-4 polypeptide according to the present invention may be isolated and/or purified (e.g. using an antibody) for instance after production by expression from encoding nucleic acid. Thus, a CTLA-4 polypeptide may be provided free or substantially free from contaminants. A CTLA-4 polypeptide may be provided free or substantially free of other polypeptides. The isolated and/or purified CTLA-4 polypeptide may be used in formulation of a composition, which may include at least one additional component, for example a pharmaceutical composition including a pharmaceutically acceptable excipient, vehicle or carrier. A composition including a CTLA-4 polypeptide according to the invention may be used in prophylactic and/or therapeutic treatment as discussed elsewhere herein.

Accordingly, one aspect of the invention is a composition comprising or consisting of a CTLA-4 polypeptide of the invention, optionally a CTLA-4 polypeptide conjugated to IgG Fc, and one or more pharmaceutical excipients. Numerous examples of CTLA-4 polypeptides according to the invention are described elsewhere herein, and any may be conjugated to an Fc region.

For example, the composition may comprise or consist of: a CTLA-4 polypeptide comprising amino acid sequence SEQ ID NO: 43 (variant 1299), SEQ ID NO: 37 (variant 1322), SEQ ID NO: 38 (variant 1321), SEQ ID NO: 36 (variant 1315), SEQ ID NO: 42 (variant 1115) or SEQ ID NO: 47 (variant 1227), conjugated to IgG Fc amino acid sequence SEQ ID NO: 59; and
one or more pharmaceutical excipients.

The composition may comprise or consist of the 1299 CTLA-4 Ig polypeptide encoded by nucleic acid deposited under NCIMB accession no. 41948, and one or more pharmaceutical excipients.

For example, the CTLA-4 polypeptide may comprise amino acid sequence SEQ ID NO: 13, SEQ ID NO: 11, SEQ ID NO: 12, SEQ ID NO: 14, SEQ ID NO: 15 or SEQ ID NO: 16.

A composition according to the invention may comprise a CTLA-4 polypeptide at a concentration of at least 70 mg/ml, e.g. at least 80 mg/ml, at least 90 mg/ml or at least 100 mg/ml. The concentration is calculated as the mass of the polypeptide including glycosylation, and includes the Fc region where present. Polypeptide concentration can be determined by standard methods of spectrophotometric measurement using an extinction coefficient based on the calculated mass of the polypeptide including glycosylation (if present). Where glycosylation is present it may be assumed to be complete. Suitable methods are illustrated in the Examples. For example, an extinction coefficient of 1.09 may be used for determining concentration, as exemplified for 1299 CTLA-4-Fc.

Formulation and Medical Use

CTLA-4 polypeptides of the present invention may be administered by monthly, or less frequent, administration. Low frequency of administration is generally desirable to reduce the burden on patients and on clinicians, but can be associated with risk of lower therapeutic efficacy and/or a need for increased product dose. Improvements in potency, affinity and/or half-life in accordance with the present invention reduce such risks and offer the possibility of lower or less frequent dosing compared with previous administration regimens.

For many patients, treatment will be required over extended periods of time, e.g. for many years, and possibly for the lifetime of the patient. Therefore it is envisaged that multiple dosages will be administered. Intervals between dosages may be in the order of days, a week, or a month. Preferably, administration is at intervals of at least or approximately 14, 21 or 28 days. Preferably, administration to a patient is by subcutaneous delivery with a 28 day or greater interval of dosing, e.g. monthly dosing.

Administration may be intravenous or by any other suitable route of administration. For example, the CTLA-4 polypeptide may be administered by subcutaneous injection, facilitating self-administration by patients at home and offering the potential advantage of reducing patient visits to the clinic compared with intravenous administration regimens.

Formulation of CTLA-4 into reduced volumes suitable for subcutaneous administration typically requires greater concentration of the CTLA-4 product compared with formulation for intravenous administration. Concentrations of at least 70 mg/ml are typically preferred for subcutaneous administration, more preferably at least 100 mg/ml. Improved stability of CTLA-4 compositions according to the present invention facilitates formulation at high concentration e.g. for subcutaneous administration.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be any suitable route, but most likely injection (with or without a needle), especially subcutaneous injection. Other preferred routes of administration include administration by inhalation or intranasal administration.

For intravenous, subcutaneous or intramuscular injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants and/or other additives may be included, as required.

A CTLA-4 polypeptide in accordance with the present invention may be used in a method of diagnosis or treatment of the human or animal body, preferably human.

Methods of treatment may comprise administration of a CTLA-4 polypeptide according to the invention e.g. administration of a pharmaceutical composition comprising the CTLA-4 polypeptide. A CTLA-4 polypeptide or composition comprising a CTLA-4 polypeptide as described herein can be for use in a method of treatment of a patient by subcutaneous or intravenous administration.

A CTLA-4 polypeptide may be given to an individual, preferably by administration in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

CTLA-4 polypeptides are useful for attenuating the T cell response, and thus can be used for treating conditions in which attenuation of the T cell response is beneficial. Clinical indications in which a CTLA-4 polypeptide may be used to provide therapeutic benefit include autoimmune diseases and/or inflammatory diseases. Examples of therapeutic indications are rheumatoid arthritis (RA), juvenile arthritis, psoriatic arthritis, psoriasis, multiple sclerosis, asthma, Crohn's disease, lupus nephritis, systemic lupus erythematosus, ankylosing spondylitis, transplant rejection, type I diabetes, sjogren syndrome and ulcerative colitis as well as other autoimmune conditions such as allopecia. CTLA-4 polypeptides according to the invention are considered to be particularly suitable for patients with moderate to severe RA.

Patients treated with CTLA-4 polypeptides or pharmaceutical compositions according to the invention may be those who have moderate to severely active RA despite previous or ongoing treatment with synthetic disease modifying anti-rheumatic drugs (DMARDs) or with biologics other than CTLA-4, e.g. other than Abatacept. A CTLA-4 polypeptide according to the invention may be used to treat patients by monotherapy, in combination with conventional DMARDs in patients with inadequate responses to conventional DMARDs, or in biologic failure patients.

Efficacy of treatment may be monitored, and data may be obtained on progression of joint damage and/or patient function.

EXAMPLES

The following CTLA4-Ig sequence has been deposited with NCIMB:
*Escherichia coli* DH5a Variant 1299=NCIMB 41948
Date of deposit=13 Mar. 2012

The strategy used to optimise the biological potency of the CTLA-4 Fc fusion molecule consisted of two major activities. One activity was the use of ribosome display to perform directed evolution of the CTLA-4 domain to select for improved affinity towards the ligands CD80 and CD86, as well as improved stability of that domain. Outputs from ribosome display selections, consisting of diverse populations of CTLA-4 variants, were sequenced and those encoding unique sequences were expressed with an Fc fusion partner for testing directly in in vitro T-cell stimulation assays. The advantage of this approach was to rank many different CTLA-4 variants (>1,000 were tested) in a drug-like format, i.e. in the context of an Fc domain which promotes dimerisation, in a biologically relevant assay. An additional feature of this strategy was to perform recombinations of those CTLA-4 mutations which were associated with improved biological function, in order to achieve further gains in potency, through synergy.

This approach was able to simultaneously select for higher affinity CTLA-4 variants and for protein stability. The affinity selections employ decreasing concentrations of target ligand, in this case CD80/86, to selectively enrich higher affinity CTLA-4 variants. Selections for improved stability use either a destabilising agent such as DTT, or hydrophobic interaction chromatography (HIC) beads to remove from the selection pool those variants which are less stable or more prone to unfolding. Thus, stability and affinity pressure could be applied within a single selection, rather than pursuing parallel approaches.

The second activity was the rational engineering of the Fc domain to introduce mutations known to remove Fc-mediated effector functions and to enhance the circulating half-life of the molecule in vivo. Different variant Fc regions were prepared as fusions to CTLA-4 and tested in accelerated in vitro stability studies to select the Fc region with the optimal stability profile.

Following these two parallel activities and subsequent screening, the most potent CTLA-4 domains, as measured by inhibition in multiple in vitro T-cell stimulation assays, were combined with the most stable engineered Fc domain, as measured by accelerated in vitro stability studies. Further in vitro testing for biological potency and protein stability allowed the relative ranking of the molecules in the final drug format.

Example 1. Construction of a Library of CTLA-4 Variants and Ribosome Display Selection for Improved Potency and Stability Ribosome display was performed on a monomeric human CTLA-4 domain, corresponding to Swiss-Prot entry P16410, residues 38-161 of the extracellular domain, with no Fc region appended. This sequence (SEQ ID NO: 35) is also referred to as wild type CTLA-4. The CTLA-4 ribosome display construct was obtained by cloning the required portion of the human CTLA-4 cDNA into a vector containing the 5' and 3' regulatory elements that are required for ribosome display (Hanes et al, Meth. Enzymol. (2000) 328:404). This construct comprises a T7 RNA polymerase promoter Sequence followed by a prokaryotic ribosome binding site (Shine-Dalgarno sequence) upstream of the CTLA-4 coding sequence. The cysteine at amino acid 120 (or position 157 according to the numbering in Swiss-Prot entry P16410) in the dimerisation interface of human CTLA-4 was mutated to a serine to prevent dimerisation of CTLA-4 molecules in ribosome display format that might otherwise interfere with selection of improved CTLA-4 sequences. Downstream of the CTLA-4 sequence, a portion of the gene III protein from filamentous phage was included to act as a spacer to allow CTLA4 variants to be displayed out of the ribosome tunnel. The CTLA-4 ribosome display construct also contained 5' and 3' stem-loop sequences at the mRNA level to help stabilise the mRNA libraries against nuclease degradation.

Error-Prone Libraries

The human CTLA-4 ribosome display construct described above was used as a template on which to generate a library of random variants using error prone PCR. Error prone PCR was applied to the CTLA-4 gene using the Diversify PCR Random Mutagenesis Kit (Clontech) according to manufacturers instructions. Reactions were tailored to give an average of four amino acid mutations per molecule and a library of approximately $2.5 \times 10^{10}$ variant molecules. This random mutagenesis procedure was further incorporated into the selection process where it was applied to the output of the third round of selection in order to introduce more diversity onto the enriched population of binders, prior to further selection.

'Loop4' Directed Library

The human CTLA-4 ribosome display construct was also used as a template on which to generate a library of variants with mutagenesis targeted to a region of the CTLA-4 molecule with the potential to contribute to the interaction with CD80 and CD86. The co-crystal structure of the human CTLA-4:human CD80 complex (Protein Data Bank (PDB): 1I8L) and the human CTLA-4:human CD86 complex (PDB: 1I85) were examined to visualise the binding interaction between the molecules, in particular the amino acid side chains of CTLA-4 in close proximity to the ligands. A region of the human CTLA-4 protein (SEQ ID 35) comprising the amino acid positions 59 to 65 (or positions 96 to 102 according to the SwissProt numbering of CTLA-4 entry P16410) was seen to form a loop extending in the direction of CD80 and CD86. Each of the residues in this region was fully randomised using saturation (NNS) mutagenesis to create a library of approximately $3.4 \times 10^{10}$ variant molecules. This 'Loop 4' library was constructed by standard techniques using overlapping oligonucleotides (SEQ ID NO: 33 and SEQ ID NO: 34).

Selection for Improved Affinity and Stability

Selection for improved binding of human CTLA-4 variants to human CD80 and CD86 was carried out using ribosome display affinity based selections as described in Hanes et al (Meth. Enzymol. (2000) 328:404). Briefly, the CTLA-4 variant DNA libraries were transcribed and then translated in a cell-free, prokaryotic translation system, and translation reactions were stalled to generate ternary ribosome display selection complexes (mRNA-ribosome-protein) that were then incubated with either human CD80 or human CD86 Fc fusion proteins (R&D Systems). CD80 or CD86 bound complexes were captured by incubation with protein G coated magnetic beads (Dynal) and bound tertiary complexes were recovered by magnetic separation whilst unbound complexes were washed away. mRNA encoding the bound CTLA-4 variants was recovered by reverse transcription and PCR. To drive the selection for CTLA-4 variants with improved binding, the selection process was repeated using decreasing concentrations of CD80 or CD86 over several rounds.

In conjunction with the selection for improved affinity towards CD80 and CD86, the CTLA-4 variant pools were simultaneously selected by ribosome display for improved stability. In the early rounds of selection (Rounds 1 and 3) DTT was used to apply a selection pressure that favoured the recovery of more stable CTLA-4 variants (Jermutus et al., Proc Natl Acad Sci USA. 2001 Jan. 2; 98(1):75-80). A final concentration of 0.5 mM DTT was included in the translation reaction, after which the reaction was incubated with a slurry of hydrophobic interaction chromatography (HIC) sepharose beads (GE Healthcare), also in the presence of 0.5 mM DTT. The HIC step was used to capture poorly-folded variants and remove them from the reaction by centrifugation, prior to incubation with CD80 and affinity selection as described above.

Hotspot Mutagenesis Library, and Rational Recombination of Key Mutations

Following the initial screening of CTLA-4 variants from the error-prone PCR and Loop4 directed libraries, mutations associated with improved activity were identified and used to design further CTLA-4 variants. In one strategy, a hotspot mutagenesis library was constructed in which positions 16, 25, 58, 70, 85 and 93 of SEQ ID NO: 35 (or positions 53, 62, 95, 107, 122 and 130 according to the SwissProt numbering of CTLA-4 entry P16410) were fully randomised in a single library using saturation (NNS) mutagenesis. The library was created using overlapping and mutagenic oligonucleotides (SEQ ID NO: 61 to SEQ ID NO: 67 inclusive). This library was then selected for improved affinity as described above.

In an alternative approach, a smaller number of mutations identified from the error-prone, Loop4 and hotspot mutagenesis libraries, which were associated with improved activity, were combined by oligonucleotide directed mutagenesis to create rational recombinants which were then directly tested for biological activity. The mutations chosen for this strategy were: I16S, S25N, S25P, G27S, M54K, N56S, L58G, T59S, F60T, L61Q, L61P, D62G, D63Y, S64P, 165N, 165V, 570A, Q80R, M85S and K93Q (or, numbered according to the CTLA-4 SwissProt entry P16410: I53S, S62N, S62P, G64S, M91K, N93S, L95G, T96S, F97T, L98Q, L98P, D99G, D100Y, S101P, I102N, I102V, S107A, Q117R, M122S and K130Q).

Example 2. Expression of CTLA-4 Wild Type and Variants as Fc Fusion Proteins

Variant CTLA-4 genes from the ribosome display selections were cloned into the vector pEU7.1. This vector allows for the expression of the CTLA-4 gene as an in-frame fusion with an IgG1 Fc region (SEQ ID NO: 56). The ribosome display outputs were PCR amplified and cloned into pEU7.1 before transformation into *E. coli* DH5-alpha cells. The oligonucleotides used for the PCR cloning were also designed to revert the serine at position 120 (residue 157 according to the numbering in Swiss-Prot entry P16410) back to the wild type amino acid cysteine. Following sequencing of individual transformants, a total of over 1,000 variants with unique CTLA-4 amino acid sequences were selected for protein expression. In batches of 88 variants, the encoding plasmid DNA was purified following the supplier protocols (Qiagen) and quantified by spectrophotometry at 260 nm so that the DNA concentration could be used to calculate the correct amount of DNA for transfection.

Expression, Purification and Quantification of CTLA-4 Proteins from 24-Well Plates 3 ml of Chinese Hamster Ovary (CHO) cells (ECACC) were seeded at 1 million cells per ml in separate wells of a 24-well plate (Whatman 734-2558) in CD-CHO medium (Invitrogen 10743-029) containing 25 μM L-Methionine Sulphoximine (Sigma M5379). 24-well plates containing cells were sealed with a breathable sandwich lid (Applikon biotechnology, Z365001224) and placed in a clamp for deep-well plates (Applikon biotechnology, Z365001700). Cells were shaken at 250 rpm, humidity 80%, 5% CO2 and 37° C. For the transfection, 50 μl NaCl 150 mM containing 3 μg of plasmid DNA was mixed with 50 μl containing 21 μg of of Linear 25 kDa PEI (Polysciences, 23966). The formed DNA-PEI complex was added to cells, allowing for no more than 15 mins between the start of complex formation and addition to cells. 16 to 24 hrs post transfection, cells were fed by addition of 300 μl/well of CD-CHO Efficient Feed B (Invitrogen A10240). Plates were shaken at 250 rpm, humidity 80%, 5% CO2 and 37° C. for an additional 5 to 6 days to allow for expression of protein into the growth medium. Following expression, spent culture medium containing protein was clarified by centrifugation at 3000 rpm for 10 mins Clarified supernatants (1.2 ml) were redistributed to a 96-well Filter Plate (3M Empore, 12146036) using the FREEDOM EVO® liquid handling robot (Tecan). Residual cell debris were removed by filtration using a vacuum pump and a QIAvac 6S Vacuum Manifold (Qiagen). 1.8 ml of clarified, filtered supernatant were processed for purification performed on a Minitrack® liquid handling robot (Perkin Elmer) using PhyTip® Protein A affinity columns (Phynexus, PTP-92-20-01), 20 μl resin bed volume). PhyTip® columns were conditioned by 500 μl NaP 20 mM pH 7.0. PhyTip® columns were then loaded by passing over the crude supernatants in 6×300 μl batches, washed with 200 μl D-PBS, 200 μl NaP 20 mM pH 7.0, eluted with 120 μl 100 mM HEPES 140 mM NaCl pH3 and neutralised with 20 μl 1M HEPES pH 8.0.

Purified proteins were transferred to a 96 well black polypropylene plate (Greiner, 655209) followed by addition of 145 μl PBS, 0.02% Tween20, 1 mg/ml BSA, 0.05% sodium azide buffer (Octet buffer). A standard curve was generated using a previously purified CTLA-4 wild type Fc fusion protein in identical buffer. A set of standard concentrations were prepared in the black polypropylene plate in a 150 μl volume with a starting concentration of 500 μg/ml and 3 fold dilutions. Using an Octet RED with Protein A coated biosensors (ForteBio Inc, 18-0004) quantification was performed using a 120 second read time with a flow rate of 200 rpm. One column of 8 biosensors was used for each 96 well plate of samples. Biosensors were regenerated by adding to 200 μl 10 mM Glycine pH1.7 (Sigma, G-7403) in the 96 well plate. Biosensors were neutralised before processing next samples by adding to 200 μl Octet buffer. 3 regeneration/neutralisation cycles were performed with a time of 30s and a flow rate of 200 rpm. Concentrations of unknown samples were determined by comparison of binding rates between unknowns and standard curve using the Octet RED data analysis software package.

Expression, Purification and Quantification of CTLA-4 Proteins at Larger Scale

For larger scale preparation of individual CTLA-4 proteins as Fc fusions, the same general steps, as used for the 24-well plate method, were applied. Plasmids containing the variant CTLA-4 gene as an in-frame fusion to IgG1 Fc were prepared from E. coli cells. For the preparation of proteins at a >100 mg scale, the entire construct containing the CTLA-4 gene directly in frame with the IgG1 Fc gene was prepared by gene synthesis. In all cases, plasmid DNA encoding the protein of interest was prepared and transfected into CHO cells for expression. In place of the 24-well plates, larger volumes of cells were grown in tissue culture flasks or wave-bags prior to purification from culture supernatants. Harvests were pooled and filtered prior to purification by protein A chromatography. Culture supernatants were loaded on a column of the appropriate size of Ceramic Protein A (BioSepra) and washed with 50 mM Tris-Hcl pH 8.0, 250 mM NaCl. Bound IgG was eluted from the column using 0.1 M Sodium Citrate (pH 3.0) and neutralised by the addition of Tris-Hcl (pH 9.0). The eluted material was buffer exchanged into PBS using Nap10 columns (GE, 17-0854-02) and the concentration of IgG was determined spectrophotometrically using an extinction coefficient based on the amino acid Sequence of the protein. Purified proteins were analysed for aggregation or degradation using SEC-HPLC and SDS-PAGE.

Example 3. Biological Activity of CTLA-4 Variants in a Raji (B-Cell) and Jurkat (T-Cell) Dual Cell Assay The screening strategy described here included measurement of the biological activity of over 1,000 CTLA-4 variants, expressed with an Fc fusion partner, in an in vitro T-cell stimulation assay. CTLA-4 variants from all the different mutagenesis strategies (including error-prone PCR, targeted mutagenesis, hotspot recombination and rational recombination) were tested for biological activity and ranked according to their biological activity relative to the wild type CTLA-4 (SEQ ID NO: 35), also expressed in Fc fusion format.

To determine the biological activity of CTLA-4 variants, samples were added to a dual cell assay consisting of Raji (B-cell) and Jurkat (T-cell) cells. The interaction of CD28, expressed by Jurkat cells, with CD80 (B7-1) and CD86 (B7-2) ligands expressed on Raji cells, combined with a co-activation signal for the T-cell receptor (such as PHA (Phytohemagglutinin)) results in Interleukin-2 (IL-2) release from Jurkat cells. Soluble CTLA-4 can bind to CD80 and CD86 ligands, blocking their interaction with CD28 and attenuating this response. Thus, potency of CTLA-4 Ig clones is determined by inhibition of IL-2 release from T-cells as measured in an IL-2 HTRF assay (CisBio 64IL2PEC).

384-well low protein binding plates (Greiner #781280) were used to perform eleven 1 in 3 serial dilutions of test samples which were made in full growth medium (RPMI 1640 Glutamax, Invitrogen #61870, 10% FBS, 1% Penicillin/Streptomycin, Invitrogen #15140). All sample dilutions were made in duplicate starting from 5-30 μg/ml top sample concentration on the cells.

Raji and Jurkat suspension cells were transferred from flasks to centrifuge vials and spun at 240 g for 5 minutes. Both cell lines were resuspended at a concentration of 750,000 cells/ml in growth media and each plated out at 0.02 ml/well (=15,000 cells/cell line/well) into a 384-well Maxisorp plate (Nunc 464718). 0.02 ml was transferred from sample dilution plates to the cell plates and 0.02 ml of 40 µg/ml PHA (Sigma # L-1668) (or 0.02 ml media for negative control wells) was added to all other wells to give a final concentration of 10 µg/ml and incubated at 37° C. with 5% $CO_2$.

After 20-24 hours, cell supernatants were harvested and IL-2 secretion was measured using a commercial IL-2 HTRF kit (CisBio 64IL2PEC). Briefly; a 'master mix' of anti-hIL-2 cryptate (donor fluorophore) and anti-hIL-2 d2 (acceptor fluorophore) was made up by diluting 1/200 in freshly made up conjugate buffer (0.2% BSA/0.8M KF/PBS). An eight-point standard curve was generated using IL-2 (NIBSC #96/504) diluted 1 in 2 in media with a top concentration of 2 ng/ml. Equal volumes of reagent master mix and samples were mixed in a 384-well low volume assay plate (Costar 3676) and incubated 3-168 hours at room temperature. Plates were read on an Envision (Perkin Elmer) using excitation wavelength of 320 nm and emission wavelengths of 620 nm & 665 nm.

% Delta F and specific binding values were calculated for each well as follows:

$$\% \text{ Delta } F = \frac{\left(\begin{array}{c}\text{Sample } A665/A620 \text{ ratio} - \\ NSB\ A665/A620 \text{ ratio}\end{array}\right)}{(NSB\ A665/A620 \text{ ratio})} \times 100$$

-continued $$\% \text{ specific binding} = \frac{\left(\begin{array}{c}\% \text{ Sample Delta } F - \\ \% \ NSB \text{ Delta } F\end{array}\right)}{\left(\begin{array}{c}\% \text{ Total Delta } F - \\ \% \ NSB \text{ Delta } F\end{array}\right)} \times 100$$

Media only wells (Min/non-specific binding (NSB)) were used as background and PHA only wells (Max/Total) wells were used to determine the maximum signal for the assays. The results were analysed using Graphpad Prism (v5.01) software and IC50 concentrations determined using a non-linear regression curve fit model (Log [inhibitor] vs response with variable slope) using the least squares fit method.

The following table summarises the number of CTLA-4 variant molecules categorised as having significant improvement in biological potency relative to the wild type CTLA-4 (SEQ ID NO: 35) also expressed in Fc fusion format:

| Mutagenesis strategy | Number of CTLA-4 variants with significant improved biological activity versus wild type CTLA-4 (SEQ ID NO: 35) in Fc fusion format |
|---|---|
| Error-prone PCR Library | 50 |
| Loop4 Targeted Library | 1 |
| Hotspot Library | 21 |
| Rational Recombinant | 35 |
| TOTAL | 107 |

Following repeat testing of these 107 CTLA-4 variants, accurate $IC_{50}$ measurements were determined and the fold improvement over wild type CTLA-4 (SEQ ID NO: 35) in Fc fusion format was calculated. The table below summarises this data for some of the most potent CTLA-4 variants from each of the mutagenesis strategies.

| CTLA-4 Variant Name | SEQ ID NO | Optimisation Strategy | Raji/Jurkat Dual Cell Assay $IC_{50}$ (nM) | Fold Improvement over Wild Type (SEQ ID NO: 35) |
|---|---|---|---|---|
| Wild Type | 35 | NA | 29.80 | 1 |
| Variant 1315 | 36 | Rational Recombinant | 0.24 | 123 |
| Variant 1322 | 37 | Rational Recombinant | 0.33 | 91 |
| Variant 1321 | 38 | Rational Recombinant | 0.44 | 68 |
| Variant 0943 | 39 | Rational Recombinant | 0.54 | 56 |
| Variant 0898 | 40 | Rational Recombinant | 0.60 | 50 |
| Variant 1319 | 41 | Rational Recombinant | 0.78 | 38 |
| Variant 1115 | 42 | Hotspot Library | 0.44 | 67 |
| Variant 1299 | 43 | Hotspot Library | 0.53 | 56 |
| Variant 1249 | 44 | Hotspot Library | 0.69 | 43 |
| Variant 1303 | 45 | Hotspot Library | 0.93 | 32 |
| Variant 1114 | 46 | Hotspot Library | 1.40 | 21 |
| Variant 1227 | 47 | Hotspot Library | 1.60 | 19 |
| Variant 0722 | 48 | Error-prone Library | 1.07 | 28 |
| Variant 0645 | 49 | Error-prone Library | 1.24 | 24 |
| Variant 0636 | 50 | Error-prone Library | 1.26 | 24 |
| Variant 0745 | 51 | Error-prone Library | 1.36 | 22 |
| Variant 0673 | 52 | Error-prone Library | 1.38 | 22 |
| Variant 0788 | 53 | Error-prone Library | 1.60 | 19 |
| Variant 0701 | 54 | Error-prone Library | 1.61 | 19 |
| Variant 0439 | 55 | Loop4 Targeted Library | 1.20 | 25 |

The sequences of these CTLA-4 variants are shown in FIG. 1A.

The $IC_{50}$ profiles of 6 of the most potent CTLA-4 variants and wild type CTLA-4 (SEQ ID NO: 35) in Fc fusion format in the Raji-Jurkat dual cell assay are shown in FIG. 3A.

Example 4. Biological Activity of CTLA-4 Variants in a Raji (B-Cell) and Primary Human CD4+ T-Cell Dual Cell Assay Human blood was collected in CPT Vacutainer collection tube (BD Biosciences) and 400 µl of CD4+ RosetteSep purification reagent (Stem Cell Technologies) was added. Following 20 minute incubation, the tubes were spun at 1700 g for 25 minutes. Cells were collected and transferred to a 50 ml conical tube and spun down at 350 g for 10 minutes. Red blood cells were lysed by resuspending in 20 ml of Vitalize reagent and incubating from 30 minutes to 1 hour. Cells were then spun down at 350 g for 10 minutes and washed once with T cell media (Xvivo-15 media (Lonza) supplemented with 1% Anti/Anti (Invitrogen)). One million cells per ml suspension of Raji and primary human CD4+ T cells was prepared in complete T cell media and kept separate until ready to add to the 96-well assay plate. In a separate 96-well plate (low protein binding), dilutions of CTLA-4 variant molecules were made in complete T cell media starting with an initial concentration of 100 µg/ml and doing twelve 1:5 serial dilutions. 100 µl of each of the CTLA-4 variant concentrations was dispensed to the tissue culture treated 96-well assay plate. The Raji and human CD4+ T cells cell suspension were mixed at a 1:1 ratio and anti-CD3 antibody (clone UCHT1 (BD Bioscience)) was added to a final concentration of 10 µg/ml. 100 µl of the cell suspension was dispensed to each well containing the CTLA-4 variants and incubated for 18 to 24 hours. The plates were then harvested by centrifugation at 350 g for 5 minutes and transferring the supernatants to a new 96-well plate. IL-2 secretion was measured using human IL-2 Duoset kit according to manufacturer's protocol (R&D Systems).

A potency comparison to wild type CTLA-4 (SEQ ID NO: 35) in Fc fusion format in the primary human CD4+ T Cell assay for 6 of the most potent CTLA-4 variants is shown in FIG. 3B.

Example 5. Biological Activity of CTLA-4 Variants in a Mixed Lymphocyte Reaction Using Peripheral Blood Mononuclear Cells from Cynomolgus Monkey Cynomolgus monkey blood from two separate animals was collected in CPT Vacutainer collection tube (BD Biosciences) and spun down at 1700 g for 25 minutes. Cells were collected and transferred to a 50 ml conical tube and spun down at 350 g for 10 minutes. Red blood cells were lysed by resuspending in 20 ml of Vitalize reagent and incubating from 30 minutes to 1 hour. Cells were then spun down at 350 g for 10 minutes and washed once with T cell media (Xvivo-15 media (Lonza) supplemented with 1% Anti/Anti (Invitrogen)). In a separate 96-well plate (low protein binding), dilutions of CTLA-4 variant molecules were made in complete T cell media starting with an initial concentration of 100 µg/ml and doing twelve 1:5 serial dilutions. 100 µl of the CTLA-4 Ig dilutions were dispensed to the tissue culture treated 96-well assay plate. PBMC cell suspension from each animals were mixed at a 1:1 ratio and 100 µl of the cell suspension was dispensed to all the wells containing the CTLA-4 Ig dilutions and incubated for 24 hours. The plates were then harvested by spinning at 350 g for 5 minutes and transferring the supernatants to a new 96-well plate. IL-2 secretion was measured using cynomolgus IL-2 ELISA kit according to manufacturer's protocol (MABTech).

A potency comparison to wild type CTLA-4 (SEQ ID NO: 35) in Fc fusion format in the cynomolgus monkey mixed lymphocyte reaction assay for two of the most potent CTLA-4 variants is shown in FIG. 3C.

Example 6. Specificity of Variant Binding to CD80 and CD86

CTLA-4 variants were labelled with horseradish peroxidase using activated HRP labelling kit (Pierce). Fc fusion protein of extracellular domains of B7 family members (R&D Systems) were coated overnight at a concentration of 5 µg/ml in PBS on Maxisorp plate (Nunc). The plates were blocked with 1% BSA and the HRP-labelled CTLA-4 variants were added at various concentrations and the amount of bound protein determined using a colorimetric substrate (BD OptEIA substrate, BD Biosciences).

Figure 4:
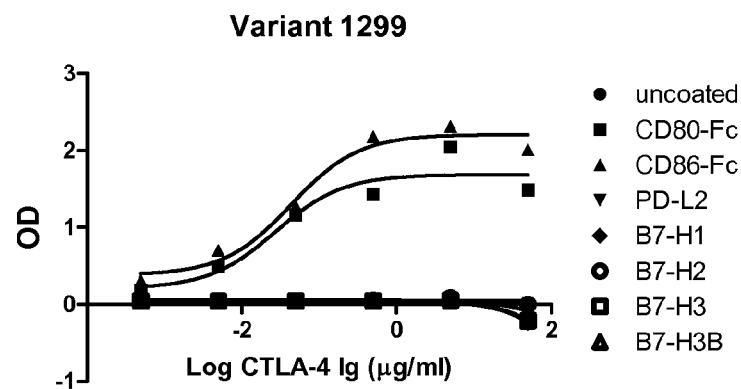
FIG. 4. Specificity of CTLA-4 variants for CD80 and CD86 compared to other related protein ligands. (A) variant 1299. (B) variant 1322.
Figure 4:
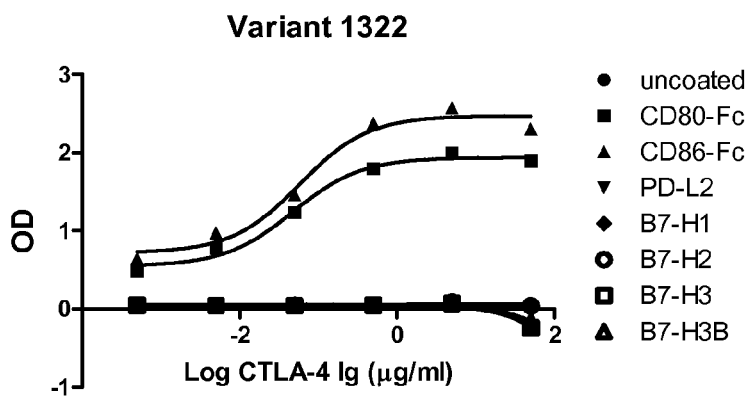

The specificity of two of the most potent CTLA-4 variants for CD80 and CD86 compared to other related protein ligands is shown in FIG. 4.

Example 7. Analysis of Fc-Mediated Effector Functions

Antibody-Dependent Cell-Mediated Cytotoxicity (ADCC) Assay

Human blood was collected in CPT Vacutainer collection tube (BD Biosciences) and spun down at 1700 g for 25 minutes. Cells were collected and transferred to a 50 ml conical tube and spun down at 350 g for 10 minutes. Red blood cells were lyzed by resuspending in 20 ml of Vitalize reagent and incubating from 30 minutes to 1 hour. Cells were then spun down at 350 g for 10 minutes and washed once with T cell media (Xvivo-15 media (Lonza) supplemented with 1% Anti/Anti (Invitrogen)). 500,000 PBMC were plated in 200 ul Xvivo-15 media in the presence of various antibodies and Fc fusion proteins. After 24 hours of incubation, B lymphocyte viability was determined using flow cytometry by staining with anti-CD19 antibodies (BD Biosciences) and 7-AAD (Molecular Probes). Number of viable B cells was calculated for each sample by multiplying 500,000 to the percentage of cells in the viable gate by front/side scatter properties that were also CD19$^+$ and 7-AAD$^-$.

Complement-Dependent Cytotoxicity (CDC) Assay

Figure 5:
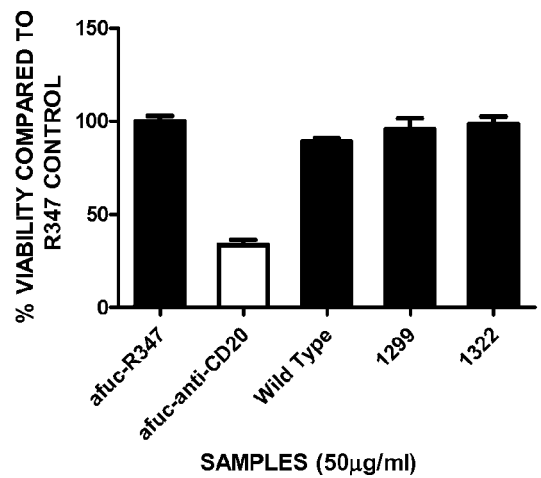
FIG. 5. Demonstration of null effector function (ADCC and CDC) for CTLA-4 variants with TM and YTE modification. (A) ADCC. (B) CDC.
Figure 5:
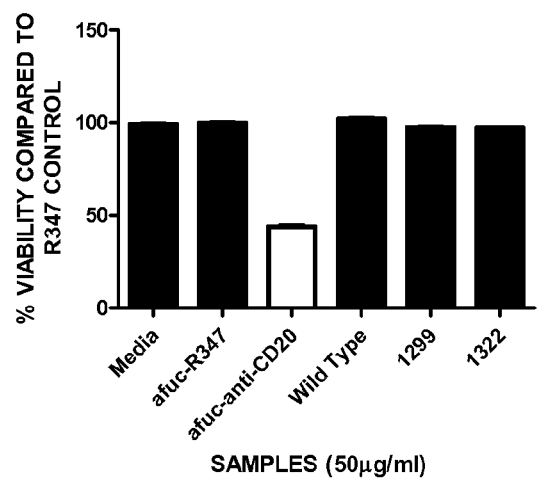

Human serum was collected in serum separator tubes and added to Xvivo-15 medium to a final concentration of 10% w/v. 100,000 Raji B cells were incubated for 18 hours in media containing various antibodies and Fc fusion proteins. Raji cell viability was determined using flow cytometry by staining with 7-AAD (Molecular Probes). Number of viable cells was calculated for each sample by multiplying 100,000 to the percentage of cells in the viable gate by front/side scatter properties that were also 7-AAD$^-$. Media containing human serum that had previously been heat inactivated for 30 minutes at 56° C. was used as a control to confirm the complement-mediated cell cytotoxicity. A demonstration of null effector function (ADCC and CDC) for two of the most potent CTLA-4 variants with TM modification is shown in FIG. 5.

Example 8. Kinetic Analysis of CTLA-4 Variants Binding to Human, Cynomolgus Monkey and Mouse CD80 and CD86

Cloning and Expression of CD80 and CD86 Reagents cDNA molecules encoding the extracellular domains (ECDs) of CD80 and CD86 from human and mouse were synthesised by primer extension PCR cloning and cloned into pDONR221 (Invitrogen Cat. No. 12536-017). Database Sequences for human and mouse CD80 and CD86 were used (see table 1). No Cynomologus monkey Sequences were available so based on the predicted high homology between Cynomolgus monkey and Rhesus Monkey, the Sequences of Rhesus monkey CD80 (ensemble accession number ENSMMUG00000016367) and CD86 (ensemble accession number ENSMMUG00000000912) were used to design primers capable of amplifying the coding Sequence of the gene in Cynomolgus monkey.

The cDNA fragments coding for the extracellular domains were then transferred to mammalian expression vector pDEST12.2 (Invitrogen) using LR Gateway Clonase II enzyme according to the manufacturer's instructions (Invitrogen Cat. No. 12538-120). The pDEST12.2 vector had been modified to contain a FLAG 10×his tag (DYKDDDD-KAAHHHHHHHHHH (SEQ ID NO: 72)) in-frame with the inserted gene of interest, and also by insertion of the oriP origin of replication from the pCEP4 vector (Invitrogen cat. no. V044-50) allowing episomal plasmid replication upon transfection into cell lines expressing the EBNA-1 gene product (such as HEK293-EBNA cells). Expressed protein in HEK293-EBNA supernatant was purified using Ni-NTA affinity chromatography (Histrap HP column (GE Healthcare Cat. No. 17-5248-02)) followed by Size Exclusion chromatography (Superdex 200 column (GE Healthcare Cat. No. 17-1069-01)).

| CD80 extracellular domains | | | |
|---|---|---|---|
| Species | Amino acids in ECD | Accession number (Swiss-Prot) | SEQ ID NO |
| Human | 1-242 | P33681 | 1 |
| Mouse | 1-245 | Q00609 | 2 |
| Cynomolgus | 1-242 | NA | 3 |

| CD86 extracellular domains | | | |
|---|---|---|---|
| Species | Amino acids in ECD | Accession number (Swiss-Prot) | SEQ ID |
| Human | 7-246 | P42081 | 4 |
| Mouse | 1-245 | P42082 | 5 |
| Cynomolgus | 1-242 | NA | 6 |

Surface Plasmon Resonance (SPR) Analysis of Binding Affinity

SPR analysis of the CTLA-4:CD80 and CD86 interactions were performed on a Biacore 2000 SPR machine. Approximately 200 RU of CTLA4 variants were covalently coupled via primary amine groups to a CM5 Biacore chip (GE healthcare cat. no. BR-1000-14) using an amine coupling kit (GE healthcare cat. no. BR-1000-50). Titrations of CD80 and CD86 in HBS-EP buffer (GE healthcare cat. no. BR-1001-88) were flowed over immobilised CTLA-4 variants. All traces were double reference subtracted. Analysis was performed using Biacore evaluation software using a 1:1 Langmuir model to fit association and dissociation constants. Where variants had very rapid kinetics equilibrium analysis was performed.

The monovalent affinity ($K_d$ in nM) of selected CTLA-4 variants and wild type CTLA-4 (SEQ ID NO: 35) in Fc fusion format for human, cynomolgus monkey and mouse ligands is shown below.

| | Human CD80 | Human CD86 | Cyno. CD80 | Cyno. CD86 | Mouse CD80 | Mouse CD86 |
|---|---|---|---|---|---|---|
| Wild type CTLA-4 | 1540 | 6420 | 1550 | 6530 | 2950 | 5550 |
| Variant 1322 | 8 | 526 | 6 | 330 | ND | ND |
| Variant 1321 | 23 | 1085 | 19 | 960 | ND | ND |
| Variant 1299 | 12 | 1388 | 10 | 1020 | ND | ND |
| Variant 1315 | 20 | 1129 | 17 | 750 | ND | ND |
| Variant 1227 | 11 | 1154 | 9 | 1020 | ND | ND |
| Variant 1115 | 20 | 1542 | 18 | 1070 | ND | ND |
| Variant 1114 | 42 | 1340 | 39 | 1280 | 2170 | 4860 |

Improvements in affinity (fold-improvement over wild type CTLA-4 in Fc fusion format) of selected CTLA-4 variants for human, cynomolgus monkey and mouse ligands is shown below.

| | Human CD80 | Human CD86 | Cyno. CD80 | Cyno. CD86 | Mouse CD80 | Mouse CD86 |
|---|---|---|---|---|---|---|
| Wild type CTLA-4 | 1 | 1 | 1 | 1 | 1 | 1 |
| Variant 1322 | 193 | 12 | 258 | 20 | ND | ND |
| Variant 1321 | 67 | 6 | 82 | 7 | ND | ND |
| Variant 1299 | 128 | 5 | 155 | 6 | ND | ND |
| Variant 1315 | 77 | 6 | 91 | 9 | ND | ND |
| Variant 1227 | 140 | 6 | 172 | 6 | ND | ND |
| Variant 1115 | 77 | 4 | 86 | 6 | ND | ND |
| Variant 1114 | 37 | 5 | 40 | 5 | 1 | 1 |

Figure 6:
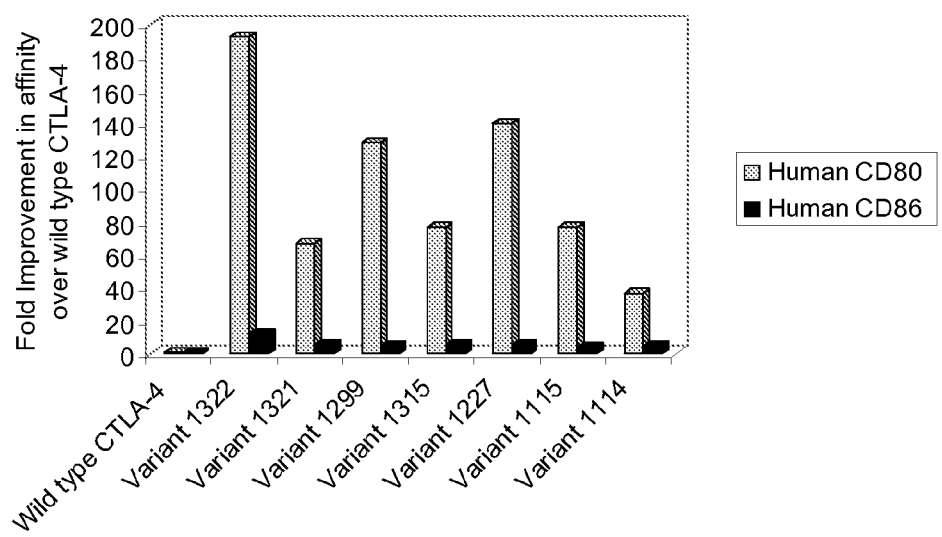
FIG. 6. Improvements in monovalent affinity towards CD80 and CD86 of CTLA-4 variants, compared with wild type CTLA-4 in Fc fusion format.

It was noted that these variants, which were the most potent variants tested in the biological activity assays, demonstrated greater affinity gains to the human CD80 ligand than the human CD86 ligand (as summarised in FIG. 6). A similar pattern of greater affinity gain against CD80 than CD86 was observed using the cynomolgus ligands.

Example 9. Accelerated Stability Studies of Wild Type CTLA-4 with Fc Mutations

Expression, purification and quantification of CTLA-4 proteins cDNAs encoding native CTLA4 extracellular domain fused with Fc variants 1 through 4 were cloned into pEE 12.4 (Lonza) and expressed in CHO cells. Briefly, 1×10⁶ CHOK1SV cells (Lonza) were transfected by nucleofection (Lonza) using program U-024 and Solution V with 5 mcg of linearized plasmid DNA. After transfection the cells were cultured in CD-CHO (Invitrogen), 1×GS supplement, and 50 μM MSX. The cells began to grow approximately 2 weeks after transfection, at which time they were expanded into shake flasks for production of the proteins. For purification, a series of steps were used starting with a Mabselect Capture step, followed by a SuperQ anion exchange polishing step, followed by SEC to removed aggregates. The proteins were stored in phosphate buffered saline (PBS) pH 7.2.

Stability Studies

Stability studies were performed on CTLA-4 molecules fused to different Fc variants to compare their stability and to determine the most stable Fc configuration. The molecules that were tested included: CTLA-4 Fc variant-1 (SEQ ID NO: 7); CTLA-4 Fc variant-2 (SEQ ID NO: 8); CTLA-4 Fc variant-3 (SEQ ID NO: 9); and CTLA4 Fc variant-4 (SEQ ID NO: 10). The amino acid differences in the Fc region are highlighted in FIG. 1B for Fc variant-1 (SEQ ID NO: 57), Fc variant-2 (SEQ ID NO: 58), Fc variant-3 (SEQ ID NO: 59) and Fc variant-4 (SEQ ID NO: 60).

CTLA-4 Fc variant-1 (SEQ ID NO: 7) is the Abatacept molecule, comprising wild type CTLA-4 (SEQ ID NO: 35) fused to an IgG1 Fc region with a modified hinge (SEQ ID NO: 57).

CTLA-4 Fc variant-2 (SEQ ID NO: 8) is Abatacept modified to incorporate a YTE mutation in the Fc region, and comprises wild type CTLA-4 (SEQ ID NO: 35) fused to IgG1 Fc with a modified hinge and a YTE mutation (SEQ ID NO: 58).

CTLA-4 Fc variant-3 (SEQ ID NO: 9) comprises wild type CTLA-4 (SEQ ID NO: 35) fused to IgG1 Fc in which the C>S mutations seen in Abatacept are reverted, comprising a wild type hinge, and further including a triple mutation (TM) and YTE mutation (SEQ ID NO: 59).

CTLA-4 Fc variant-4 (SEQ ID NO: 10) comprises a wild type CTLA-4 (SEQ ID NO: 35) fused to IgG4 Fc comprising a YTE mutation and a hinge region mutation comprising proline at position 111 (SEQ ID NO: 60).

Position 111 in Swiss Prot numbering corresponds to residue 14 of the corresponding IgG1 sequence SEQ ID NO: 56 as shown in FIG. 1, or residue 228 in the full length constant region of IgG4. Introduction of a serine to proline mutation at this position is known to stabilise the inter-chain disulphide interaction and therefore minimise the formation of half IgG$_4$ molecules (Aalberse and Schuurman, *Immunology* 105(1):9-19 2002; Van der Neut Kolfschoten et al, *Science* 307(5844):1554-7 2007; Angal et al, *Mol Immunol* 30(1):105-8 1993; Schuurman et al *Mol Immunol* 38(1):1-8 2001) thus minimising challenges associated with candidate drug development. In addition, as this proline residue is found in the corresponding position of IgG$_1$ it is not anticipated to raise any immunogenicity concerns.

The molecules were received in liquid form at ~10 mg/mL in PBS buffer. The 4 molecules were concentrated using Amicon μltra Centrifugal filters, 30,000 MW cutoff. The molecules were centrifuged at 4200 g until target volume was achieved (30-60 minutes). Concentrations were measured spectrophotometrically using a standard antibody extinction coefficient of 1.4. Final concentrations were calculated to be between 71-85 mg/ml. Although in this example an antibody extinction coefficient of 1.4 was used, the actual extinction coefficient of the polypeptide was subsequently determined to be closer to 1.1. These calculated concentrations therefore actually represent a concentration range of 91-108 mg/ml. Higher concentration may be achieved if desired by continuing ultrafiltration, subject to volume restrictions.

Samples of each Fc variant were incubated at 5° C. and 25° C. for 1 month. Size exclusion high performance liquid chromatography (SE-HPLC) was the stability indicating assay used to determine and compare degradation rates for the 4 molecules. SE-HPLC was run according to SOP DV-9525 with a 1 ml/min flow rate. Any peak that elutes before the monomer peak (with an elution time less than that of the monomer) in the HPLC chromatogram is designated as an aggregate peak. Any peak that elutes after the monomer peak (with an elution time greater than that of the monomer) is designated as a fragment peak. The total percentage of aggregate and fragment is determined by the area of the aggregate peak(s) and fragment peak(s) as a fraction of the total area of all protein peaks in the chromatogram. Prior to incubation, SE-HPLC was run on all samples for the time 0 data point. Thereafter, SE-HPLC data was collected each week for the 25° C. stability study and every 2 weeks for the 5° C. stability study. Total duration for both studies was 1 month. Shown below are the aggregation, fragmentation and degradation rates calculated using a linear fit to the 1 month data.

| Rates after 1 month at 5° C. | | | |
|---|---|---|---|
| Molecule | % Aggregate/ Month | % Fragment/ Month | % Purity Loss/ Month |
| Fc variant-1 (SEQ ID 57) | 2.6 | 0.4 | 3.0 |
| Fc variant-2 (SEQ ID 58) | 3.2 | 0 | 3.2 |
| Fc variant-3 (SEQ ID 59) | 1.0 | 0 | 1.0 |
| Fc variant-4 (SEQ ID 60) | 0.8 | 0.9 | 1.7 |

| Rates after 1 month at 25° C. | | | |
|---|---|---|---|
| Molecule | % Aggregate/ Month | % Fragment/ Month | % Purity Loss/ Month |
| Fc variant-1 (SEQ ID 57) | 12.8 | 0.7 | 13.4 |
| Fc variant-2 (SEQ ID 58) | 14.3 | 0.9 | 15.2 |
| Fc variant-3 (SEQ ID 59) | 7.8 | 0 | 7.8 |
| Fc variant-4 (SEQ ID 60) | 9.2 | 3.6 | 12.8 |

Based on this data, Fc variant-3 (SEQ ID NO: 59) was selected as the optimal fusion partner based on the lowest rates of purity loss at both 5° C. and 25° C.

Example 10. Accelerated Stability Studies of CTLA-4 Variants Fused to Fc Variant-3

Stability studies were performed on 6 of the most potent CTLA-4 variant molecules fused to Fc variant-3 (SEQ ID NO: 59) to determine the most stable CTLA-4 variant. The molecules that were tested in this format were: variant 1115 (SEQ ID NO: 15), variant 1227 (SEQ ID NO: 16), variant 1299 (SEQ ID NO: 13), variant 1315 (SEQ ID NO: 14), variant 1321 (SEQ ID NO: 12), variant 1322 (SEQ ID NO: 11).

The molecules were received in liquid form at ~10 mg/mL in PBS buffer. The 6 molecules were concentrated using Amicon μltra Centrifugal filters, 30,000 MW cutoff. The molecules were centrifuged at 4200 g until target volume was achieved (30-60 minutes). Extinction coefficients were calculated using the amino acid sequences. The calculated extinction coefficients were 1.10 for 1315 and 1321; and 1.09 for 1115, 1227, 1299 and 1322. Concentrations were measured using the appropriate extinction coefficient. Final concentrations were between 94.6-101.6 mg/ml.

Stability studies were performed at 5° C. and 25° C. following the same guidelines described in the previous section, with the exception of collecting only 0 and 1 month timepoints for the 5° C. stability study. Total duration for both studies was 1 month. Shown below are the aggregation, fragmentation and degradation rates calculated using a linear fit to the 1 month data.

Rates after 1 month at 25° C.

| Molecule | % Aggregate/Month | % Fragment/Month | % Purity Loss/Month |
|---|---|---|---|
| 1115 | 6.0 | 0 | 6.0 |
| 1227 | 4.0 | 0 | 4.0 |
| 1315 | 24.0 | 0 | 24.0 |
| 1299 | 1.5 | 0 | 1.5 |
| 1321 | 8.8 | 0 | 8.8 |
| 1322 | 1.4 | 0 | 1.4 |

Rates after 1 month at 5° C.

| Molecule | % Aggregate/Month | % Fragment/Month | % Purity Loss/Month |
|---|---|---|---|
| 1115 | 0.4 | 0 | 0.4 |
| 1227 | 0.8 | 0 | 0.8 |
| 1315 | 2.6 | 0 | 2.6 |
| 1299 | 0.2 | 0 | 0.2 |
| 1321 | 0.6 | 0 | 0.6 |
| 1322 | 0.1 | 0 | 0.1 |

The variants 1299 and 1322 were found to have the lowest levels of purity loss in both the 5° C. and 25° C. studies over 1 month. Therefore, the stability studies were extended to 6 months at 5° C. for the variants 1299 and 1322. Shown below are the results obtained from the monthly timepoints.

1299 5° C. Stability Data

| Timepoint (months) | % Aggregate | % Fragment | % Purity |
|---|---|---|---|
| 0 | 1.1 | 0.0 | 98.9 |
| 1 | 1.4 | 0.0 | 98.6 |
| 2 | 2.0 | 0.0 | 98.0 |
| 3 | 1.9 | 0.0 | 98.1 |
| 4 | 2.4 | 0.0 | 97.6 |
| 5 | | | |
| 6 | | | |

% Purity Loss/Year Calculated from Linear Fit of Data = 3.6%

1322 5° C. Stability Data

| Timepoint (months) | % Aggregate | % Fragment | % Purity |
|---|---|---|---|
| 0 | 1.2 | 0.0 | 98.8 |
| 1 | 1.4 | 0.0 | 79.5 |
| 2 | 1.8 | 0.0 | 98.2 |
| 3 | 1.7 | 0.0 | 98.3 |
| 4 | 2.1 | 0.0 | 97.9 |
| 5 | | | |
| 6 | | | |

% Purity Loss/Year Calculated from Linear Fit of Data = 2.6%

Example 11. Construction of a Tetravalent CTLA-4 Molecule

Design and Construction of Tetravalent CTLA-4 Expression Vectors

Using the nitrophenol-binding IgG NIP 74 (Heavy chain SEQ ID NO: 17; light chain SEQ ID NO: 18) as a scaffold, tetravalent CTLA-4 was produced by fusing CTLA-4 to the amino-terminus of both the antibody $V_H$ and $V_L$ chains (FIG. 7A). The expression constructs were produced by fusing CTLA-4 to the $V_H$ and $V_L$ using a 2-step PCR strategy and then sub-cloning the PCR products into IgG expression vectors containing antibody constant domains. The primary PCR amplified CTLA-4 and the IgG $V_H$ and $V_L$ with gene-specific primers (SEQ ID NOS 21-28) that added a flexible linker at the 3' end of CTLA-4 and to the 5' end of the $V_H$ and $V_L$. The secondary 'pull-through' PCR attached CTLA-4 to the 5' end of the $V_H$ and the $V_L$ by annealing the complementary linker Sequences. The final CTLA-4-$V_H$ construct was amplified using primers that introduced a BssHII at the 5'end and a BstEII site at the 3'end (SEQ ID NOS 29-30). The final CTLA-4-VL construct was amplified using primers that introduced an ApaLI at the 5'end and a PacI site at the 3'end (SEQ ID NOS 31-32). The PCR products were then digested with the respective restriction enzymes before they were ligated directly into pre-digested IgG expression vectors, pEU1.4 for the CTLA-4-$V_H$ cassette and pEU3.4 for the CTLA-4-$V_L$ cassette, and used to transform chemically competent E. coli DH5-alpha cells. Correct clones, corresponding to SEQ ID NOS 19 and 20, were identified by sequence analysis for expression studies.

Expression and Purification of Tetrameric CTLA-4

For both plasmids required for transfection, one coding for the CTLA-4-heavy chain fusion and one coding for the CTLA-4 light chain fusion, a single colony was used to inoculate 100 ml 2×TY broth containing 100 μg/mL ampicillin. Cultures were incubated overnight (16 hours) at 37° C. and 300 rpm. Plasmid DNA was isolated from the bacterial pellet using the EndoFree Plasmid Maxi Kit (QIAGEN; 12362) following the manufacturer's instructions. On the morning of transfection, CHO cells were seeded at one million cells per ml in CD-CHO media (Invitrogen; 10743-029) containing 25 μM L-methionine sulphoximine (Sigma; M5379). Cells were cultured in a volume of 500 ml and incubated at 37° C., 140 rpm, 80% humidity and 5% $CO_2$. In order to form DNA-PEI complexes for transfection, 250 μg of each vector was mixed and diluted in 150 mM NaCl to give 500 μg DNA in a final volume of 1 ml. The DNA was then mixed with 1 ml 5 mg/ml PEI (Polysciences; 23966), diluted in 150 mM NaCl, and incubated at room temperature for 1 minute. The DNA-PEI mix was then carefully added to the CEP6 culture which was then incubated for 24 hours prior to the addition of 150 ml CD-CHO Efficient Feed B (Invitrogen; A10240). The culture was then incubated for a further six days.

The culture was centrifuged at 2000 g for 30 minutes; the clarified culture supernatant was then filtered through a 500 ml Stericup (Millipore; SCGVU05RE). Purification of tetravalent CTLA-4, from the clarified culture supernatant was performed using an ÄKTApurifier 10 system (GE Healthcare; 28-4062-64) and affinity chromatography followed by gel filtration chromatography. A 5 ml MabSelect Sure column (GE Healthcare; 11-0034-94) was equilibrated with ten column-volumes D-PBS (Invitrogen; 14040-174). The clarified culture supernatant was passed over the column before the column was washed with a further ten column-volumes D-PBS. The bound protein was eluted with 0.1 M glycine, pH 2.7 and 1 ml fractions were collected. Each fraction was neutralized with 100 μl 1M Tris, pH 10 and the fractions containing the eluted protein were pooled and concentrated to 2 ml using a Vivaspin, 10,000 MWCO filtration unit (Sartorius Stedim; VS2002) following the manufacturer's instructions. The 2 ml concentrated sample was loaded onto a HiLoad Superdex 200, 16/60 gel filtration column (GE Healthcare; 17-1069-01), which had been equilibrated in D-PBS. Throughout the process, 1.2 ml fractions were collected. Those fractions containing the target protein of the correct molecular weight (retention volume of 56 ml) were pooled, concentrated to 1 ml using a Vivaspin, 10,000 MWCO filtration units and stored at −80° C.

The purified tetrameric CTLA-4 was profiled alongside wild type CTLA-4 (SEQ ID NO: 35) in Fc fusion format in the Raji-Jurkat dual cell assay and data are shown in FIG. 8.

The $IC_{50}$ values in this assay for tetrameric CTLA-4 and wild type CTLA-4 (SEQ ID NO: 35) in Fc fusion format were 1.93 nM and 11.39 nM, respectively. This indicates a gain in potency of 5.9-fold upon conversion from a dimeric, Fc fusion format to a tetrameric, IgG-like format.

What is claimed is:

1. An isolated CTLA-4 polypeptide having greater affinity for binding human CD80, greater potency and/or greater stability compared with wild type CTLA-4 SEQ ID NO: 35, wherein the polypeptide comprises:
   amino acid sequence SEQ ID NO: 68, SEQ ID NO: 43, SEQ ID NO: 37, SEQ ID NO: 38, SEQ ID NO: 36, SEQ ID NO: 42 or SEQ ID NO: 47.

2. A CTLA-4 polypeptide according to claim 1, wherein the polypeptide has greater affinity than wild type CTLA-4 (SEQ ID NO: 35) for binding human CD86.

3. A CTLA-4 polypeptide according to claim 1, conjugated to an IgG Fc amino acid sequence.

4. A CTLA-4 polypeptide according to claim 3, wherein the IgG Fc is a human IgG1 Fc modified to reduce Fc effector function, and comprises a native human IgG1 Fc hinge region.

5. A CTLA-4 polypeptide according to claim 3, wherein the IgG Fc amino acid sequence comprises SEQ ID NO: 59.

6. A CTLA-4 polypeptide according to claim 3, wherein the IgG Fc amino acid sequence comprises a human lgG1 Fc region in which one or both of the following groups of residues are substituted as follows:

F at residue 20, E at residue 21, S at residue 117; and
Y at residue 38, T at residue 40, E at residue 42,
the residue numbering being defined with reference to SEQ ID NO: 56.

7. A CTLA-4 polypeptide according to claim 1, wherein the polypeptide comprises amino acid SEQ ID NO: 68.

8. A CTLA-4 polypeptide according to claim 1, wherein the polypeptide comprises amino acid SEQ ID NO: 43.

9. A CTLA-4 polypeptide according to claim 1, wherein the polypeptide comprises amino acid SEQ ID NO: 37.

10. A CTLA-4 polypeptide according to claim 1, wherein the polypeptide comprises amino acid SEQ ID NO: 38.

11. A CTLA-4 polypeptide according to claim 1, wherein the polypeptide comprises amino acid SEQ ID NO: 36.

12. A CTLA-4 polypeptide according to claim 1, wherein the polypeptide comprises amino acid SEQ ID NO: 42.

13. A CTLA-4 polypeptide according to claim 1, wherein the polypeptide comprises amino acid SEQ ID NO: 47.

14. A CTLA-4 polypeptide according to claim 1, wherein the polypeptide comprises the sequence of SEQ ID NO: 13.

15. A composition comprising a CTLA-4 polypeptide according to claim 1, and one or more pharmaceutical excipients.

* * * * *